US012274784B2

(12) United States Patent
Chang et al.

(10) Patent No.: US 12,274,784 B2
(45) Date of Patent: Apr. 15, 2025

(54) METHODS FOR REDUCING SIDE EFFECTS OF IMMUNOTHERAPY

(71) Applicants: SYNERGENE THERAPEUTICS, INC., Potomac, MD (US); GEORGETOWN UNIVERSITY, Washington, DC (US)

(72) Inventors: Esther H. Chang, Potomac, MD (US); Joe B. Harford, Potomac, MD (US); Sang Soo Kim, Rockville, MD (US)

(73) Assignees: SYNERGENE THERAPEUTICS, INC., Potomac, MD (US); GEORGETOWN UNIVERSITY, Washington, DC (US)

( * ) Notice: Subject to any disclaimer, the term of this patent is extended or adjusted under 35 U.S.C. 154(b) by 922 days.

(21) Appl. No.: 16/597,861

(22) Filed: Oct. 10, 2019

(65) Prior Publication Data
US 2020/0113829 A1    Apr. 16, 2020

Related U.S. Application Data

(60) Provisional application No. 62/745,217, filed on Oct. 12, 2018.

(51) Int. Cl.
| | | |
|---|---|---|
| *A61K 9/127* | (2006.01) | |
| *A61K 31/282* | (2006.01) | |
| *A61K 38/17* | (2006.01) | |
| *A61K 39/395* | (2006.01) | |
| *A61P 35/00* | (2006.01) | |
| *A61P 35/04* | (2006.01) | |
| *C07K 16/28* | (2006.01) | |

(52) U.S. Cl.
CPC ............ *A61K 9/127* (2013.01); *A61K 31/282* (2013.01); *A61K 38/1709* (2013.01); *A61K 38/1758* (2013.01); *A61K 39/3955* (2013.01); *A61P 35/00* (2018.01); *A61P 35/04* (2018.01); *C07K 16/2818* (2013.01); *C07K 16/2827* (2013.01); *C07K 16/2881* (2013.01); *C07K 2317/21* (2013.01); *C07K 2317/24* (2013.01); *C07K 2317/56* (2013.01)

(58) Field of Classification Search
CPC .. A61K 9/127; A61K 31/282; A61K 38/1709; A61K 38/1758; A61K 39/3955; A61K 47/6849; A61K 9/1272; A61K 39/39541; A61K 47/6913; A61P 35/00; A61P 35/04; C07K 16/2818; C07K 16/2827; C07K 16/2881; C07K 2317/21; C07K 2317/24; C07K 2317/56; C07K 2317/622
See application file for complete search history.

(56) References Cited

U.S. PATENT DOCUMENTS

| | | |
|---|---|---|
| 7,479,276 B1 | 1/2009 | Xu et al. |
| 7,780,882 B2 | 8/2010 | Chang et al. |
| 8,617,514 B2 | 12/2013 | Chang et al. |
| 8,859,274 B2 | 10/2014 | Xu et al. |
| 8,865,127 B2 | 10/2014 | Chang et al. |
| 2005/0002998 A1 | 1/2005 | Chang et al. |
| 2007/0065432 A1 | 3/2007 | Xu et al. |
| 2007/0065499 A1 | 3/2007 | Chang et al. |
| 2007/0224195 A1 | 9/2007 | Ellenhorn et al. |
| 2007/0231378 A1* | 10/2007 | Chang ............... A61K 39/39558 424/182.1 |
| 2009/0191261 A1 | 6/2009 | Xu et al. |
| 2010/0329981 A1 | 12/2010 | Chang et al. |
| 2014/0099254 A1 | 4/2014 | Chang et al. |
| 2014/0356285 A1 | 12/2014 | Arap et al. |
| 2019/0038713 A1* | 2/2019 | Sobol ..................... A61K 45/06 |

FOREIGN PATENT DOCUMENTS

| | | | | |
|---|---|---|---|---|
| EP | 1811036 A2 * | 7/2007 | ......... A61K 31/4025 |
| WO | 99/25320 A1 | 5/1999 | |
| WO | 2017/079746 A3 | 5/2017 | |

OTHER PUBLICATIONS

Braun et al., "Regulation of Cytotoxic T-cell Responses by p53 in Cancer," Translational Cancer Research, 5(6): 692-697 (2016).
Buerki et al., "Immunotherapy of Primary Brain Tumors: Facts and Hopes," Clinical Cancer Research: An Official Journal for the American Association for Cancer Research, 24(21): 5198-5205 (2018).
Camp et al., "Transferrin Receptor Targeting Nanomedicine Delivering Wild-Type p53 Gene Sensitizes Pancreatic Cancer to Gemcitabine Therapy," Cancer Gene Therapy 20: 222-228 (2013).
Chen et al., "Elements of Cancer Immunity and the Cancer-Immune Set Point," Nature, 541(7637): 321-330 (2007).
Cui et al., "Immunomodulatory Function of the Tumor Suppressor p53 in Host Immune Response and the Tumor Microenvironment," International Journal of Molecular Sciences, 17(11) PMID: 27869779 (2016).
Daud et al., "Programmed Death-ligand 1 Expression and Response to the Anti-programmed Death 1 Antibody Pembrolizumab in Melanoma," Journal of Clinical Oncology: Official Journal of the American Society of Clinical Oncology, 34(34): 4102-4109 (2016).

(Continued)

*Primary Examiner* — Robert S Cabral
(74) *Attorney, Agent, or Firm* — MEDLER FERRO WOODHOUSE & MILLS PLLC

(57) ABSTRACT

This invention provides methods to overcome the current limitations of immune checkpoint immunotherapy to provide more effective methods of treating cancer. In embodiments this invention provides a means of using of p53 gene therapy to augment immune checkpoint inhibition by combining antibodies targeting immune checkpoint molecules with SGT-53, a nanomedicine carrying a plasmid encoding human wild-type p53. This invention provides means of increasing tumor immunogenicity, enhancing both innate and adaptive immune responses, and reducing tumor-induced immunosuppression, sensitizing otherwise refractory tumors to anti-immune checkpoint antibodies. In other embodiments this invention also unexpectedly reduces immune-related toxicities that are seen with immunotherapies.

10 Claims, 30 Drawing Sheets

(56) References Cited

OTHER PUBLICATIONS

Dempke et al., "Programmed Cell Death Ligand-1 (PD-L1) as a Biomarker for Non-Small Cell Lung Cancer (NSCLC) Treatment—Are We Barking up the Wrong Tree?" Translational Lung Cancer Research 7(Suppl 3): S275-S9 (2018).
Descotes et al., "Immunotoxicity of Monoclonal Antibodies," mAbs, 1(2): 104-111 (2009).
El-Deiry et al., "Insights into Cancer Therapeutic Design Based on p53 and TRIAL Receptor Signaling," Cell Death and Differentiation, 8(11): 1066-1075 (2001).
El-Deiry et al., "The Role of p53 in Chemosensitivity and Radiosensitivity," Oncogene, 22(47): 7486-7495 (2003).
Fridman et al., "The Immune Contexture in Human Tumours: Impact on Clinical Outcome," Nature Reviews Cancer, 12(4): 298-306 (2012).
Gameiro et al., "Radiation-induced Immunogenic Modulation of Tumor Enhances Antigen Processing and Calreticulin Exposure, Resulting in Enhanced T-cell Killing," Oncotarget 5(2): 403-416 (2014).
Gangadhar et al., "Mitiating the Toxic Effects of Anticancer Immunotherapy," Nature Reviews Clinical Oncology, 11(2): 91-99 (2014).
Garon et al., "Pembrolizumab for the Treatment of Non-small-cell Lung Cancer," The New England Journal of Medicine, 372(21): 2018-2028 (2015).
Guo et al., "Local Activation of p53 in the Tumor Microenvironment Overcomes Immune Suppression and Enhances Antitumor Immunity," Cancer Research, 77(9): 2292-2305 (2017).
Harter et al., "Distribution and Prognostic Relevance of Tumor-infiltrating Lymphocytes (TILs) and PD-1/PD-L1 Immune Checkpoints in Human Brain Metastases," Oncotarget, 6(38): 40836-40839 (2015).
Hassel et al., "Combined Immune Checkpoint Blockade (anti-PD-1/anti-CTLA-4): Evaluation and Management of Adverse Drug Reactions," Cancer Treatment Reviews, 57: 36-49 (2017).
Herbst et al., "Pembrolizumab Versus Docetaxel for Previously Treated, PD-L1-positive, Advanced Non-small-cell Lung Cancer (Keynote-010): A Randomised Controlled Trial," Lancet, 387(10027): 1540-1550 (2016).
Hirayama et al., "Anti-PD-L1 Treatment Enhances Antitumor Effect of Everolimus in a Mouse Model of Renal Cell Carcinoma," Cancer Science, 107(12): 1736-1744 (2016).
Holmgaard et al., "Tumor-expressed IDO Recruits and Activates MDSCs in a Treg-dependent Manner," Cell Reports, 13(2): 412-424 (2015).
Jing et al., "PD-1/PD-L1 Blockades in Non-small-cell Lung Cancer Therapy," OncoTargets and Therapy, 9: 489-502 (2016).
Kaur et al., "Radiation-induced Effects and the Immune System in Cancer," Frontiers in Oncology, 2:191 (2012).
Ke et al., "Non-small-cell Lung Cancer-induced Immunosuppression by Increased Human Regulatory T cells via Foxp3 Promoter Demthylation," Cancer Immunology, Immunotherapy, 65(5): 587-599 (2016).
Kim et al., "Immune Checkpoint Modulators: An Emerging Antiglioma Armamentarium," Journal of Imm. Res., PMID: 26881264 (2016).
Kim et al., "The Clinical Potential of Targeted Nanomedicine: Delivery to Cancer Stem-like Cells," Molecular Therapy: The Journal of the American Society of Gene Therapy, 22(2): 278-291 (2014).
Kim et al., "A Nanoparticle Carrying the p53 Gene Targets Tumors Including Cancer Stem Cells, Sensitizes Glioblastoma to Chemotherapy and Improves Survival," ACS Nano., 8(6): 5494-5514 (2014).
Kim et al., "A Tumor-targeting p53 Nanodelivery System Limits Chemoresistance to Temozolomide Prolonging Survival in a Mouse Model of Glioblastoma Multiforme," Nanomedicine: Nantotechnology, Biology, and Medicine, 11(2): 301-311 (2015).
Kim et al., "Combination with SGT-53 Overcomes Tumor Resistance to a Checkpoint Inhibitor," Oncoimmunology, 7(10): e1484982 (2018).
Kudlak et al., "Acute Lung Injury Following the Use of Granulocyte-macrophage Colony-stimulating Factor," International Journal of Critical Illness and Injury Science, 3(4): 279-281 (2013).
Lechner et al., "Immunogenicity of Murine Solid Tumor Models as a Defining Feature of in vivo Behavior and Response to Immunotherapy," J. Immunother., 36(9): 477-489 (2013).
Lettau et al., "Insights into the Molecular Regulation of FasL (CD178) Biology," European Journal of Cell Biology, 90(6-7): 456-466 (2011).
Li et al., "The Role of Adenovirus-mediated Retinoblastoma 94 in the Treatment of Head and Neck Cancer," Cancer Research 62(16): 4637-4644 (2002).
Mahoney et al., "Combination Cancer Immunotherapy and New Immunomodulatory Targets," Nature Reviews Drug Discovery, 14(8): 561-584 (2015).
Mall et al., "Repeated PD-1/PD-L1 Monoclonal Antibody Administration Induces Fatal Xenogeneic Hypersensitivity Reactions in a Murine Model of Breast Cancer," Oncoimmunology, 5(2): e1075114 (2015).
McGuire et al., "Anti-PD-1-induced High-grade Hepatitis Associated with Corticosteroid-resistant T Cells: A Case Report," Cancer Immunology, Immunotherapy, 67(4): 563-573 (2018).
Mellman et al., "Cancer Immunotherapy Comes of Age," Nature, 480(7378): 480-489 (2011).
Mello et al., "Deciphering p53 Signaling in Tumor Suppression," Current Opinion in Cell Biology, 51: 65-72 (2017).
Menendez et al., "Interactions Between the Tumor Suppressor p53 and Immune Responses," Current Opinion in Oncology, 25(1): 85-92 (2013).
Meslin et al., "Granzyme B-induced Cell Death Involves Induction of p53 Tumor Suppressor Gene and its Activation in Tumor Target Cells," The Journal of Biological Chemistry, 282(45): 32991-32999 (2007).
Moore et al., "Nanocomplex-based TP53 Gene Therapy Promotes Anti-tumor Immunity Through TP53- and STING-dependent Mechanisms," Oncoimmunology, 7(7): e1404216 (2018).
Munoz-Fontela et al., "Emerging Roles of p53 and Other Tumour-suppressor Genes in Immune Regulation," Nature Reviews Immunology, 16(12): 741-750 (2016).
O'Donnell et al., "Acquired Resistance to anti-PD1 Therapy: Checkmate to Checkpoint Blockade?" Genome Medicine, 8(1): 111 (2016).
Ott et al., "Combination Immunotherapy: A Road Map," Journal for Immunotherapy of Cancer, 5:16 (2017).
Owen-Schaub et al., "Wild-type Human p53 and a Temperature-sensitive Mutant Induce Fas/APO-1 Expression," Molecular and Cellular Biology, 15(6): 3032-3040 (1995).
Pardoll et al., "The Blockade of Immune Checkpoints in Cancer Immunotherapy," Nature Reviews Cancer, 12(4): 252-24 (2012).
Pfirschke et al., "Immunogenic Chemotherapy Sensitizes Tumors to Checkpoint Blockade Therapy," Immunity, 44(2): 343-354 (2016).
Pirollo et al., "Safety and Efficacy in Advanced Solid Tumors of a Targeted Nanocomplex Carrying the p53 Gene used in Combination with Docetaxel: A Phase 1B Study," Mol. Ther., 24(9): 1697-1706 (2016).
Prendergast et al., "Discovery of IDO1 Inhibitors: From Bench to Bedside," Cancer Research, 77(24): 6795-67811 (2017).
Ribas et al., "What Does PD-L1 Positive or Negative Mean?" The Journal of Experimental Medicine, 213(13): 2835-2840 (2016).
Safta et al., "Granzyme B-activated p53 Interacts with Bcl-2 to Promote Cytotoxic Lymphocyte-mediated Apoptosis," J. Immunol., 194(1): 418-42 (2015).
Senzer et al., "Phase I Study of a Systemically Delivered p53 Nanoparticle in Advanced Solid Tumors," Molecular Therapy: The Journal of the American Society of Gene Therapy, 21(5): 1096-1103 (2013).
Sica et al., "Macrophage Polarization in Tumour Progression," Seminars in Cancer Biology, 18(5): 349-355 (2008).
Siefker-Radke et al., "A Phase I Study of a Tumor-targeted Systemic Nanodelivery System, SGT-94, in Genitourinary Cancer," Mol. Ther., 24(8): 1484-1491 (2016).

(56) References Cited

OTHER PUBLICATIONS

Soussi et al., "Shaping Genetic Alterations in Human Cancer: the p53 Mutation Paradigm," Cancer Cell, 12(4): 303-312 (2007).
Syn et al., "De-novo and Acquired Resistance to Immune Checkpoint Targeting," The Lancet Oncology, 18(12): e731-e741 (2017).
Taube et al., "Association of PD-1, PD-1 Ligands, and Other Features of the Tumor Immune Microenvironment with Response to anti-PD-1 Therapy," Clinical Cancer Research: An Official Journal of the American Association for Cancer Research, 20(19): 5064-5074 (2014).
Thiery et al., "p53 Potentiation of Tumor Cell Susceptibility to CTL Involves Fas and Mitochondrial Pathways," J. Immunol., 174(2): 871-878 (2005).
Valente et al., "p53 as the Focus of Gene Therapy: Past, Present and Future," Current Drug Targets, PMID: 29336259 (2018).
Wang et al., "p53 Increases MHC Class I Expression by Upregulating the Endoplasmic Reticulum Aminopeptidase ERAP1," Nature Communications, 4: 2359 (2013).
Wang et al., "Suppression of Type I IFN Signaling in Tumors Mediates Resistance to Anti-pD-1 Treatment That Can be Overcome by Radiotherapy," Cancer Research, 77(4): 839-850 (2017).
Willingham et al., "The CD47-signal Regulatory Protein Alpha (SIRPa) Interaction is a Therapeutic Target for Human Solid Tumors," PNAS, 109(17): 6662-6667 (2012).
Xu et al., "Transferrin-liposome-mediated Systemic p53 Gene Therapy in Combination with Radiation Results in Regression of Human Head and Neck Cancer Xenografts," Human Gene Therapy, 10(18): 2941-2952 (1999).
Yu et al., "Allele-specific 53 Mutant Reactivation," Cancer Cell 21(5): 614-625 (2012).
Zaretsky et al., "Mutations Associated with Acquired Resistance to PD-1 Blockade | Melanoma," The New England Journal of Medicine, 375(9): 819-829 (2016).
Zeng et al., "Anti-PD-1 Blockade and Stereotactic Radiation Produce Long-Term Survival in Mice with Intracranial Gliomas," International Journal of Radiation Oncology, Biology, Physics, 86(2): 343-349 (2013).
Zhang et al., "Adenoviral-mediated Retinoblastoma 94 Produces Rapid Telomere Erosion, Chromosomal Crisis, and Caspase-dependent Apoptosis in Bladder Cancer and Immortalized Human Urothelial Cells but not in Normal Urothelial Cells," Cancer Research, 63(4): 760-765 (2003).
Zhou et al., "The Oncolytic Peptide LTX-315 Triggers Immunogenic Cell Death," Cell Death & Disease, 7: e2134 (2016).
Zhu et al., "p53 Induces TAP1 and Enhances the Transport of MHC Class I Peptides," Oncogene, 18(54): 7740-7747 (1999).
Zou et al., "PD-L1 (B7-H1) and PD-1 Pathway Blockade for Cancer Therapy: Mechanisms, Response Biomarkers, and Combinations," Science Translational Medicine, 8(328): 328r4 (2016).

* cited by examiner

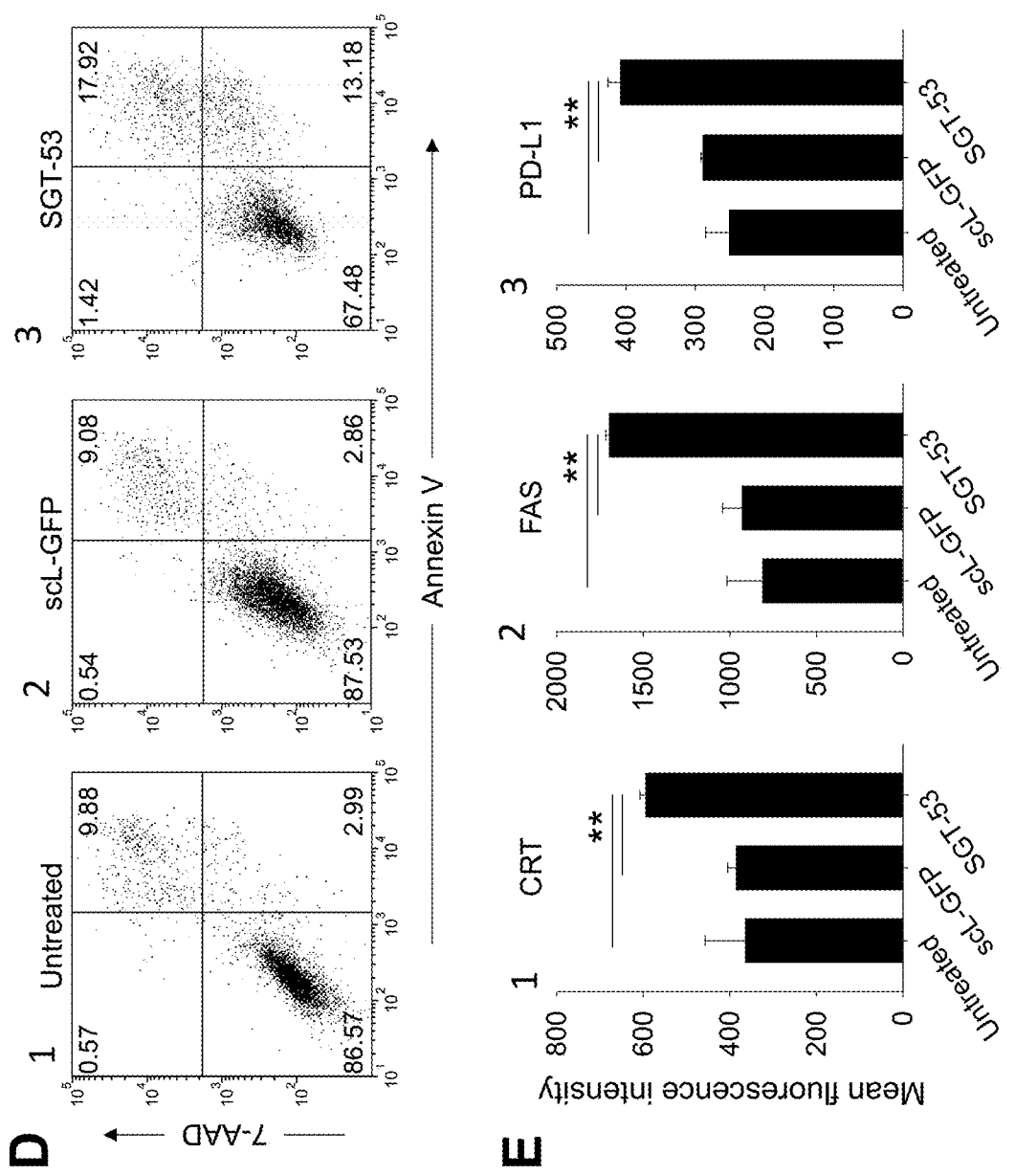
FIG 1D-E

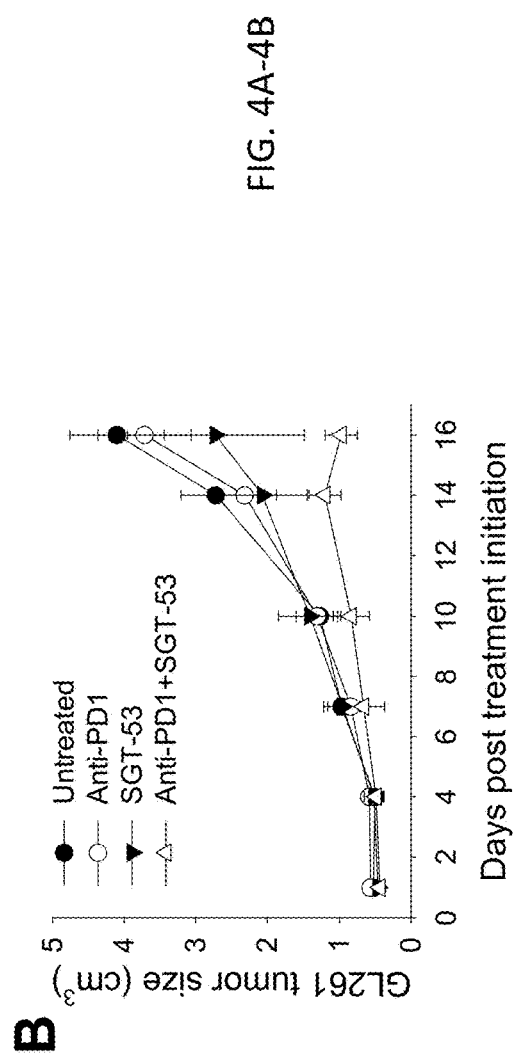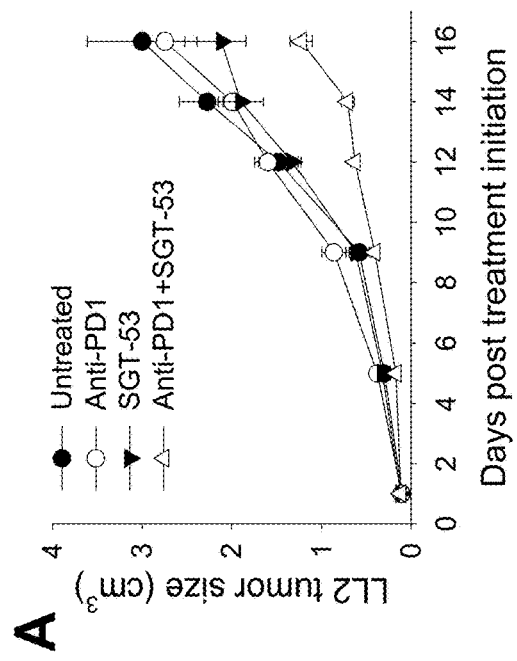
FIG. 4A-4B
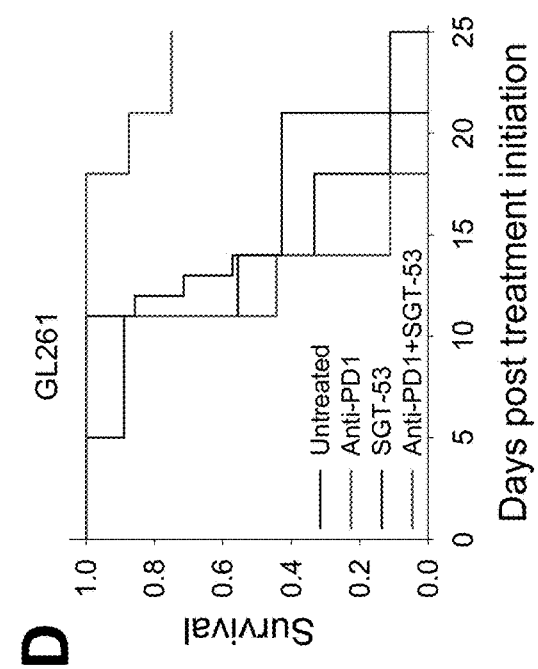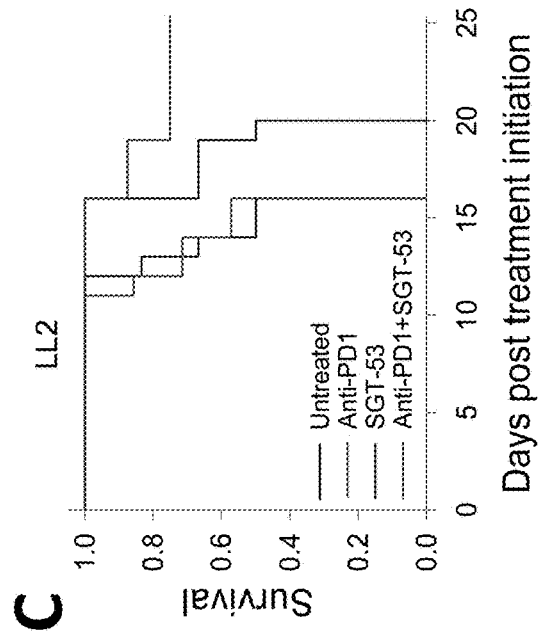
FIG. 4C-4D

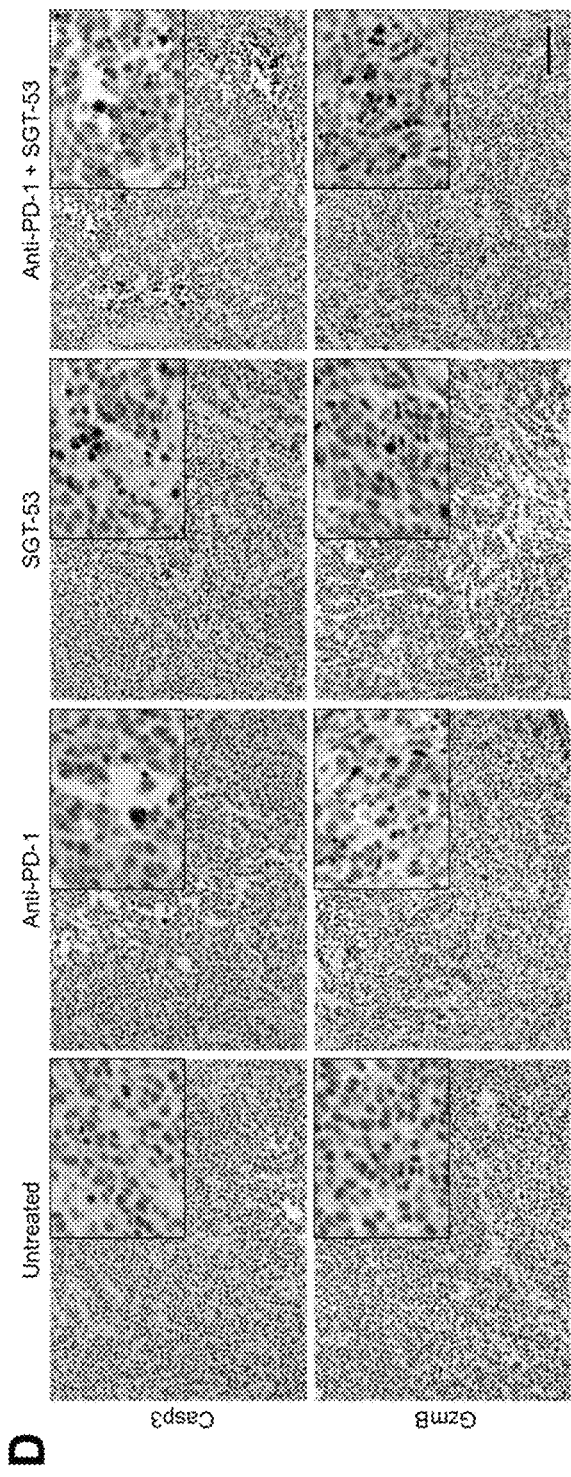
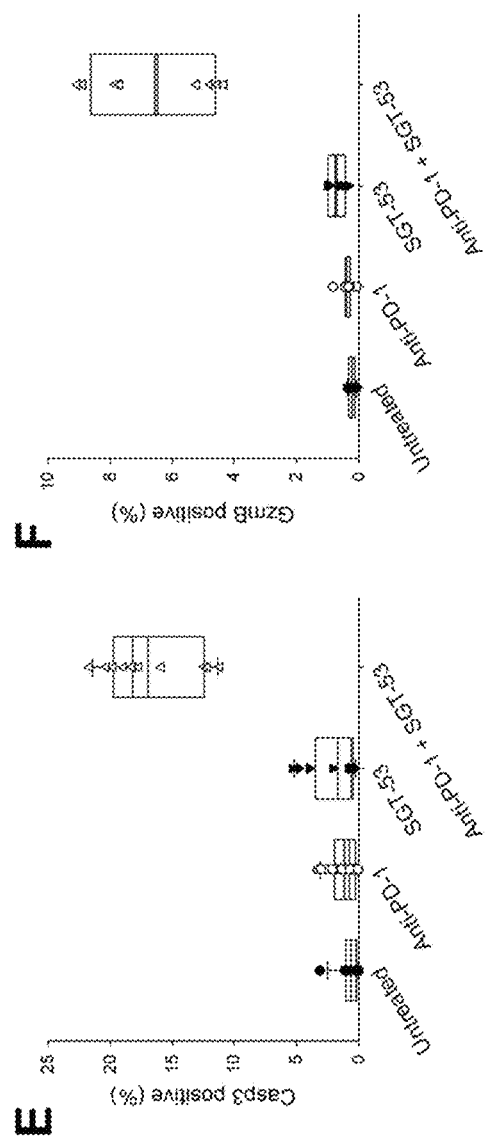
FIG. 12D-12F

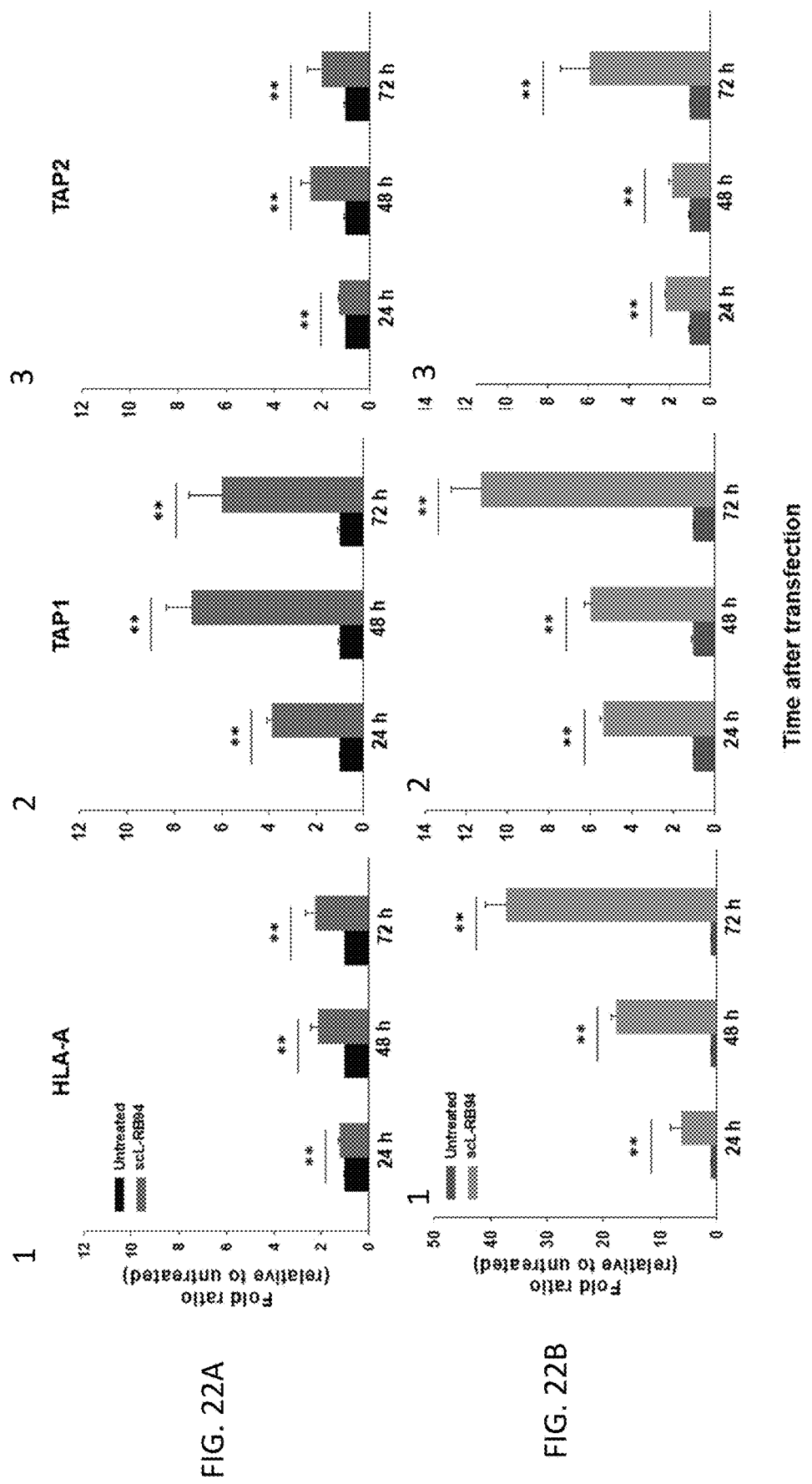

METHODS FOR REDUCING SIDE EFFECTS OF IMMUNOTHERAPY

CROSS REFERENCE TO RELATED APPLICATIONS

This present application claims benefit of U.S. Provisional Patent Application No. 62/745,217, filed Oct. 12, 2019, the disclosure of disclosure of which is incorporated by reference herein in its entirety.

FIELD OF THE INVENTION

This invention provides methods to overcome the current limitations of immune checkpoint immunotherapy to provide more effective methods of treating cancer. In embodiments this invention provides a means of using tumor suppressor gene therapy to augment immune checkpoint inhibition. In one embodiment, immune checkpoint inhibition is augmented by combining antibodies targeting immune checkpoint molecules with SGT-53 (also known as scL-p53) a nanomedicine carrying a plasmid encoding human wild-type p53. In another embodiment another tumor suppressor gene, RB94, delivered by the scL nanocomplex, unexpectedly can induce immunogenic changes in cancer cells, effectively promoting the upregulation of immune recognition molecules and increasing the infiltration of immune cells into the tumor. The involvement of RB94 in upregulating the immune recognition molecules appears to be multifaceted in that scL delivered RB94 increases the ligands related to both innate and adaptive immunity. This invention provides means of increasing tumor immunogenicity, enhancing both innate and adaptive immune responses, and reducing tumor-induced immunosuppression, sensitizing otherwise refractory tumors to anti-immune checkpoint antibodies. In other embodiments this invention also unexpectedly reduces immune-related toxicities that are seen with immunotherapies.

BACKGROUND OF THE INVENTION

Immune checkpoints are regulators of the immune system. These pathways are crucial for self-tolerance, which prevents the immune system from attacking cells indiscriminately. These immune checkpoint molecules can be categorized as inhibitory checkpoint molecules or stimulatory checkpoint molecules.

In recent years, manipulation of immune checkpoints or pathways has emerged as a powerful and promising strategy to stimulate antitumor T cell response and to prevent tumor immune evasion (1, 2) with promise as an effective form of immunotherapy of human cancer (1).

There are several types of immunotherapy, including immune checkpoint inhibitors, non-specific immunotherapies (interferons and interleukins), oncolytic virus therapy, chimeric antigen receptor (CAR) T-cell therapy, and cancer vaccines. Among these immunotherapies, immune checkpoint inhibitors have been demonstrated to elicit durable antitumor immune responses in a range of tumor types. Checkpoint blockade has dramatically improved outcomes for many patients even after their tumors have metastasized.

Monoclonal antibodies that target the cytotoxic T lymphocyte-associated antigen 4 (CTLA-4) or the programmed cell death protein 1 pathway (i.e., PD1/PD-L1) are the most widely studied and have demonstrated clinical effectiveness in various types of cancer (3, 4). However, despite the clinical potential of these immunomodulatory antibodies, a large number of patients either do not respond or develop resistance to checkpoint inhibitors as a single therapeutic modality (5, 6).

One example is glioblastoma multiforme (GBM). Despite immune checkpoint inhibitors demonstrating clinical potential in a range of tumor types, the disappointing result from clinical trials in patients with recurrent GBM represents continued challenges for immunotherapy of brain cancer.

Another example concerns non-small cell lung cancer (NSCLC) tumors. NSCLC have developed an array of strategies to evade or suppress antitumor immune responses, which likely contribute to the failure of conventional treatment (7). The majority of lung cancer diagnosed in the U.S. involve metastatic disease that has a five-year survival rate of just under 6% (Grant 4). The recent emergence of immunotherapy—which activates the body's own immune system to destroy cancer cells—has been seen as holding substantial promise for improved outcome in NSCLC. Antibodies that recognize the immune checkpoint molecules programmed cell death-1 (PD-1) or programmed death-ligand 1 (PD-L1) have been approved by the U.S Food and Drug Administration (FDA) as either first-line or second-line treatments for NSCLC. However, while immunotherapy has proven to be a game changer in oncology generally speaking, treatments involving immune checkpoint inhibitors have met with very limited success in treatment so far for advanced lung cancers with only about 10-20% of NSCLC patients showing prolonged and durable responses (8). In some groups of patients (e.g., never smokers), response rates are only 3-4% (9).

More significantly, some treatment-related toxicities, including death, have been observed which limit the use of these drugs, especially when both anti-PD 1 and anti-CTLA-4 were combined (10). To overcome the current limitations of immune checkpoint immunotherapy, methods to enhance the efficacy and safety would be advantageous (11). One familiar with the art would be aware that there are ongoing efforts that combine checkpoint blockade with other treatment modalities including vaccines, cytokines, radiation and chemotherapeutic agents (12-14). However, it is also well known that none are using the combination of gene replacement therapy and immune checkpoint modulators.

The tumor suppressor p53 is a transcription factor that regulates cell cycle arrest and apoptosis in response to genotoxic and oncogenic stresses. Given that over 50% of all of human cancers have a mutational inactivation of p53 and alterations in the p53 pathway (15, 16) and p53-null mice are highly predisposed to cancer development (17), restoring p53 function is an attractive cancer therapeutic strategy (18, 19). Moreover, recent experimental and clinical results suggest that p53 participates in immune regulation, and that the p53 pathway can be exploited to alter the immunological landscape of tumors for improved cancer therapies (20, 21). However, despite what is known in the art regarding the interaction of p53 and immune regulation there has not been any indication that using p53 gene therapy in combination with antibodies targeting immune checkpoint molecules would reduce the immune related toxicities that have been associated with immunotherapies. Thus these findings are novel, surprising and unexpected.

It is well known that RB94 is a tumor suppressor gene. The protein encoded by this gene is a truncated form of full-length RB 110, a cell cycle regulator and tumor-suppressor originally identified in retinoblastomas (Grant 16, 19). It is know that the Rb94 gene and protein encoded by it is different than the RB 110 gene and the protein it encodes. The RB94 protein lacks 112 N-terminal amino acids of the wild-type RB 110 protein. The loss of these amino acids appears to unleash the tumor suppressor activity of RB 110, and RB94 has been shown to induce cytotoxicity in diverse cancer cell types while leaving normal cells unharmed (Grant 19-22). The efficiency of RB94 is not dependent on the presence or absence of RB 110 in tumors, and RB94 has been shown to induce death in tumor cells that have either wild-type and mutated RB 110 genes (Grant 16, 19). It has been shown that RB94 protein has a longer half-life than RB 110 protein, remains in the active hypo-phosphorylated form for longer time, and causes telomere erosion and chromosomal fragmentation. The anti-tumor effect of RB-94 has been established to be through cell cycle arrest in the G2-M phase, increased levels of apoptosis, decreased telomerase activity and chromosomal fragmentation (22, 23). Thus, it is surprising and unexpected that the nanocomplex delivered RB-94 gene enhances the innate anti-tumor immune response in the host and decreases tumor immune evasion as a means of inhibiting tumor cell growth.

It will be understood by those familiar with the art that the mechanism of action and the pathways involved in such are very different between the p53 and the RB94 genes.

BRIEF SUMMARY OF THE INVENTION

As the use of gene replacement therapy and immune checkpoint modulators for the treatment of cancers in novel and unique, the present invention fulfills these needs by providing a method of treating a disease in a patient, comprising providing a ligand-targeted cationic liposomal complex, comprising a cationic liposome, a targeting ligand that is complexed with the cationic liposome, but is not chemically conjugated to the cationic liposome, and wherein the targeting ligand does not comprise a lipid tag, and a nucleic acid and administering the ligand-targeted cationic liposomal complex in combination with an immune checkpoint modulator to the patient to treat the disease and reduce immune-related toxicity. In a preferred embodiment the nucleic acid encodes a tumor suppressor gene. In a more preferred embodiment the tumor suppressor gene is p53. In an additional preferred embodiment the tumor suppressor gene is RB94.

It also provides a method of treating a disease in a patient, comprising providing a ligand-targeted cationic liposomal complex, comprising a cationic liposome, a targeting ligand that is complexed with the cationic liposome, but is not chemically conjugated to the cationic liposome, and wherein the targeting ligand does not comprise a lipid tag, and a nucleic acid and administering the ligand-targeted cationic liposomal complex to enhance the innate anti-tumor immune response in the host and decrease tumor immune evasion as a means of inhibiting tumor cell growth. In a preferred embodiment the nucleic acid encodes a tumor suppressor gene. In a more preferred embodiment the tumor suppressor gene is RB94.

In suitable embodiment, the disease that is treated is a cancer, such as a primary or metastatic brain tumor, a breast cancer, a neuroendocrine tumor, a melanoma, a pancreatic cancer, a prostate cancer, a head and neck cancer, an ovarian cancer, a lung cancer, a kidney cancer, a liver cancer, a vaginal cancer, a urogenital cancer, a gastric cancer, a colorectal cancer, a cervical cancer, a liposarcoma, an angiosarcoma, a rhabdomyosarcoma, a choriocarcinoma, a retinoblastoma, and a multiple myeloma. In embodiments, the breast cancer is a primary or metastatic breast cancer, an inflammatory breast cancer (IBC), Ductal Carcinoma In Situ (DCIS), or an invasive ductal carcinoma (IDC) including .IDC Type: Tubular Carcinoma of the Breast, IDC Type: Medullary Carcinoma of the Breast, IDC Type: Mucinous Carcinoma of the Breast, IDC Type: Papillary Carcinoma of the Breast, IDC Type: Cribriform Carcinoma of the Breast, as well as Invasive Lobular Carcinoma (ILC), Lobular Carcinoma In Situ (LCIS), Male Breast Cancer, Molecular Subtypes of Breast Cancer, Paget's Disease of the Nipple, Phyllodes Tumors of the Breast, Metastatic Breast Cancer. In embodiments the lung cancer is small cell lung cancer, non-small cell lung cancer (NSCLC) which included adenocarcinoma, squamous cell carcinoma and large cell carcinoma.

In additional embodiments, the disease is an immune related disease.

Suitably, the nucleic acid encodes a tumor suppressor protein. It is well known in the art that p53 and Rb94 are tumor suppressor proteins.

In embodiments, the immune checkpoint modulator is an inhibitor checkpoint molecule, including but not limited to, adenosine A2A receptor (A2AR), B7-H3, B7-H4, B- and T-lymphocyte attenuator (BTLA), cytotoxic T lymphocyte antigen 4 (CTLA-4), Indoleamine 2,3-dioxygenase (IDO), Killer cell immunoglobulin-like receptors (KIR), Lymphocyte-activation gene 3 (LAG3), programmed cell death-1 (PD-1), programmed death-ligand 1 (PD-L1), programmed death-ligand 2 (PD-L2), T-cell immunoglobulin and mucin domain 3 (TIM-3), V-domain Ig suppressor of T cell activation (VISTA) (protein), TIGIT (T cell Ig and ITIM domain), CD47, and Signal regulatory protein alpha (SIRPalpha).

In further embodiments, the immune checkpoint modulator is a stimulatory check point molecule, including but not limited to CD27, CD28, CD40, CD122, CD137, OX40, glucocorticoid-induced tumor necrosis factor receptor-related protein (GITR), and inducible costimulator of T cells (ICOS).

Suitably, the ligand is transferrin, folate, an antibody, an antibody fragment including, but not limited to, a single chain Fv antibody fragment, and in embodiments, the single chain Fv antibody fragment is an anti-transferrin receptor single chain Fv (TfRscFv).

In embodiments, the ligand-targeted cationic liposomal complex is administered via intravenous (IV), intratumoral (IT), intralesional (IL), aerosal, percutaneous, oral, endoscopic, topical, intramuscular (IM), intradermal (ID), intraocular (IO), intraperitoneal (IP), sublingual (SL), transdermal (TD), intranasal (IN), intracerebral (IC), intraorgan (e.g. intrahepatic), slow release implant, subcutaneous administration, or via administration using an osmotic or mechanical pump.

In further embodiments, provided herein is a method of reducing the toxic side effects of an immune checkpoint modulator in a patient, comprising providing a ligand-targeted cationic liposomal complex, comprising a cationic liposome, a targeting ligand that is complexed with the cationic liposome, but is not chemically conjugated to the cationic liposome, and wherein the targeting ligand does not comprise a lipid tag, and a nucleic acid encoding a tumor suppressor protein, and administering the ligand-targeted cationic liposomal complex in combination with an immune checkpoint modulator to the patient, wherein the side effects of the immune checkpoint modulator are reduced or eliminated.

Suitably, the tumor suppressor protein is p53 or RB94.

In embodiments, the immune checkpoint modulator is an inhibitor checkpoint molecule, including but not limited to, A2AR, B7-H3, B7-H4, BTLA, CTLA-4, B7-1, B7-2, IDO, KIR, LAG3, PD-1, PD-L1, PD-L2, TIM-3, VISTA (protein), TIGIT (T cell Ig and ITIM domain), CD47, and SIRPalpha. In suitable embodiments, the inhibitor checkpoint modulator is an anti-PD1 antibody.

In additional embodiments, the immune checkpoint modulator is a stimulatory check point molecule, including but not limited to, CD27, CD28, CD40, CD122, CD137, OX40, GITR, and ICOS.

Suitably, ligand is transferrin, folate, an antibody, an antibody fragment including, but not limited to, a single chain Fv antibody fragment, including wherein the single chain Fv antibody fragment is an anti-transferrin receptor single chain Fv (TfRscFv).

Suitably, the side effects are reduced in a patient undergoing treatment for a cancer, including wherein the cancer is a primary or metastatic brain tumor, a breast cancer, a neuroendocrine tumor, a melanoma, a pancreatic cancer, a prostate cancer, a head and neck cancer, an ovarian cancer, a lung cancer, a kidney cancer, a liver cancer, a vaginal cancer, a urogenital cancer, a gastric cancer, a colorectal cancer, a cervical cancer, a liposarcoma, an angiosarcoma, a rhabdomyosarcoma, a choriocarcinoma, a retinoblastoma, and a multiple myeloma. In embodiments, the breast cancer is a primary or metastatic breast cancer, an inflammatory breast cancer (IBC), Ductal Carcinoma In Situ (DCIS), or an invasive ductal carcinoma (IDC) including .IDC Type: Tubular Carcinoma of the Breast, IDC Type: Medullary Carcinoma of the Breast, IDC Type: Mucinous Carcinoma of the Breast, IDC Type: Papillary Carcinoma of the Breast, IDC Type: Cribriform Carcinoma of the Breast, as well as Invasive Lobular Carcinoma (ILC), Lobular Carcinoma In Situ (LCIS), Male Breast Cancer, Molecular Subtypes of Breast Cancer, Paget's Disease of the Nipple, Phyllodes Tumors of the Breast, Metastatic Breast Cancer. In embodiments the lung cancer is small cell lung cancer, non-small cell lung cancer (NSCLC) which included adenocarcinoma, squamous cell carcinoma and large cell carcinoma.

In additional embodiments, the patient is undergoing treatment for an immune related disease.

Suitably, the side effect is a xenogeneic hypersensitivity reaction.

In additional embodiments, provided herein is a method of treating a cancer expressing a receptor for advanced glycation end products (RAGE), in a patient, comprising providing a ligand-targeted cationic liposomal complex, comprising, a cationic liposome, a targeting ligand that is complexed with the cationic liposome, but is not chemically conjugated to the cationic liposome, and wherein the targeting ligand does not comprise a lipid tag; and a nucleic acid encoding a tumor suppressor protein; and administering the ligand-targeted cationic liposomal complex to the patient to reduce the RAGE expression and treat the cancer. In suitable embodiments, the methods inhibit the development of metastatic disease.

Suitably, the cancer is a primary or metastatic brain tumor, a breast cancer, a neuroendocrine tumor, a melanoma, a pancreatic cancer, a prostate cancer, a head and neck cancer, an ovarian cancer, a lung cancer, a kidney cancer, a liver cancer, a vaginal cancer, a urogenital cancer, a gastric cancer, a colorectal cancer, a cervical cancer, a liposarcoma, an angiosarcoma, a rhabdomyosarcoma, a choriocarcinoma, a retinoblastoma, and a multiple myeloma. In embodiments, the breast cancer is a primary or metastatic breast cancer, an inflammatory breast cancer, or an invasive ductal carcinoma.

In suitable embodiments, the tumor suppressor protein is p53 or RB94.

Suitably, the ligand is a single chain Fv antibody fragment, including the wherein single chain Fv antibody fragment is an anti-transferrin receptor single chain Fv (TfRscFv).

BRIEF DESCRIPTION OF DRAWINGS

The foregoing and other features and aspects of the present technology can be better understood from the following description of embodiments and as illustrated in the accompanying drawings. The accompanying drawings, which are incorporated herein and form a part of the specification, further serve to illustrate the principles of the present technology. The components in the drawings are not necessarily to scale.

FIGS. 1A-1E: SGT-53 increases immunogenicity and induces ICD. (A) 4T1 cells were treated with either SGT-53 or scL-vec nanocomplex. Expression of human p53 was assessed by quantitative RT-PCR. The fold-change relative to mouse GAPDH mRNA is shown on a log scale (n=6). (B) Expression of mouse genes associated with immune responses was assessed by RT-PCR in the cells treated with SGT-53 (n=6). (C) Release of HMGB 1 and ATP was assessed in the culture media (n=6). (D) (1-3) Induction of apoptosis was assessed via Annexin V/7-AAD staining at 48 h after transfection. Numbers in the quadrants indicate the percentage of cells in that quadrant. (E) (1-3) Expression of cell surface components of immunogenicity was assayed at 48 h after transfection via FACS (n=4). Data are shown as mean±SEM. *$p<0.001$, **$p<0.05$, 1-way ANOVA with Bonferroni t-test.

FIGS. 4A-4B: Enhanced tumor growth inhibition by anti-PD1 plus SGT-53 combination in mouse syngeneic tumor models. C57BL/6 mice with s.c. LL2 tumors (A) or GL261 tumors (B) were randomized to therapy with anti-PD1 (200 µg antibody/mouse/injection, i.p.), either alone or in combination with SGT-53 (30 µg DNA/mouse/injection, i.v.) (n=6-10). Tumor sizes were plotted versus the number of days after initiation of the treatment. Data are shown as mean±SEM.

FIGS. 4C-4D Prolongation of survival by anti-PD1 plus SGT-53 combination in mouse syngeneic tumor models. C57BL/6 mice with s.c. LL2 tumors (A) or GL261 tumors (B) were randomized to therapy with anti-PD1 (200 μg antibody/mouse/injection, i.p.), either alone or in combination with SGT-53 (30 μg DNA/mouse/injection, i.v.). Kaplan-Meier survival curve of mice (n=6-10). Mice were injected twice per week with SGT-53 and/or anti-PD 1 for three weeks.

FIG. 12A-12F: The combination of anti-PD-1 and SGT-53 inhibits tumor growth. C57BL/6 mice with subcutaneous GL261 tumor were randomized to therapy with anti-PD-1 (200 ug antibody), SGT-53 (30 ug DNA), or combination of both twice weekly for 2.5 weeks (N=6-10). (A) Changes in tumor sizes were plotted versus the number of days after initiation of the treatment. (B) Quantification of tumor weight at harvest on day 17. Red lines indicate average tumor weight. $*p<0.001$, $**p<0.05$. (C) Changes in gene expression of tumors using NanoString analysis are shown. (D) Representative immunohistochemical staining of Casp3 and GzmB are shown. Scale bar, 100 μm. Quantification of (E) Casp3 and (F) GzmB are shown. DAB signal was analyzed using IHC-Profiler plugin in ImageJ.

(FIG. 20A) scL-RB94 increases NK cells associated with human NSCLC H358 tumors in athymic mice. Mice received 6 intravenous injections of scL-RB94 (30 ug of plasmid DNA per injection) prior to harvesting the tumor and analyzing via FACS for NK cells. (FIG. 20B) FACS analysis of mature dendritic cells infiltrating NSCLC H292 tumors after the mice received 6 intravenous injections of scL-RB94. (FIG. 20C) (1-3). Human NSCLC cell line H292 was transfected with scL-RB94 and harvested after 24 h, 48 h, and 72 h. The transcription levels of 3 NK activation ligands (ULBP2, MICA, and MICB) were assessed by RT-PCR. Each sample was repeated in triplicate *p<0.05, **p<0.001, Student's t test.

FIG. 22A-2B: Human NSCLC cell lines H358 (FIG. 22A (1-3)) and H292 (FIG. 22B (1-3)) were transfected with scL-RB94 and harvested at 24 h, 48 h, and 72 h. The transcription levels of the molecules involved in antigen presentation (HLA-A) and antigen processing (TAP1/2) were assessed with RT-PCR. Each sample was repeated in triplicate. *p<0.05, **p<0.001.

DETAILED DESCRIPTION OF THE INVENTION

Figures 1A, 1B, 1C:
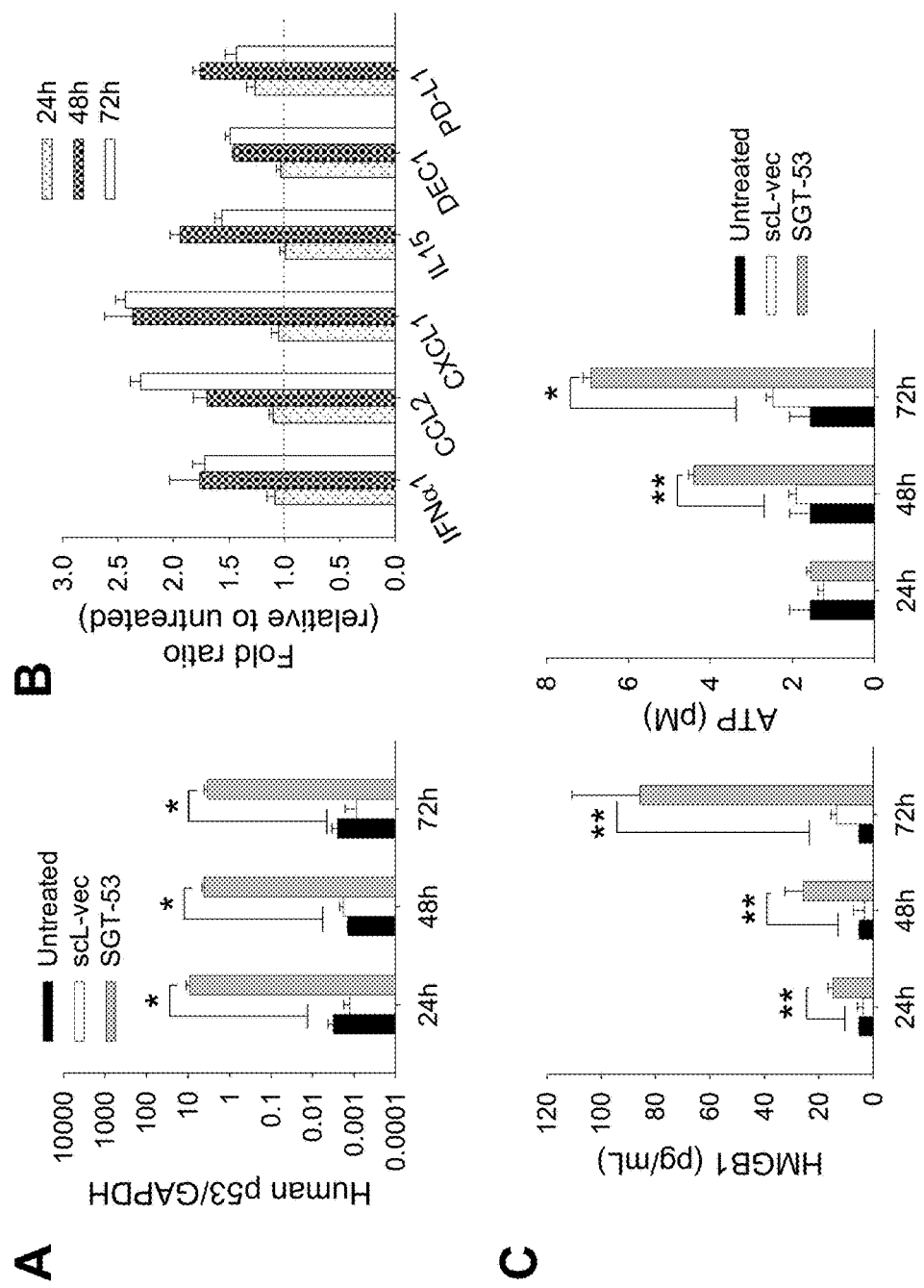

The present invention fulfills the need for a more effective and safer therapeutic modality involving immunotherapies by providing a tumor targeting nanocomplex for delivery of the p53 tumor suppressor gene to tumor cells, even those in the brain, in combination with such immune checkpoint modulators as a new unique therapeutic modality. The present invention also fulfills the need for a more effective therapeutic modality involving immunotherapies by providing a tumor targeting nanocomplex for delivery of the RB94 tumor suppressor gene to tumor cells, such as those in the lungs, alone or in combination with such immune checkpoint modulators, as a new unique therapeutic modality.

Regarding brain tumors, several immune checkpoint antibodies are currently undergoing clinical development for treatment of primary and recurrent brain tumors (2). However, the results from these trial in patients with recurrent GBM have been disappointing and represents continued challenges for immunotherapy of brain cancer. Acquired and intrinsic drug resistance especially coupled with the major problem of restricted permeation of drugs by the blood-brain barrier (BBB) may all contribute to treatment failure in patients with GBM. In addition, GBM has developed an array of strategies to evade/suppress the antitumor immune response, which also contribute to the treatment failure (24, 25). Thus it would be surprising and unexpected for the combination of checkpoint modulators (e.g. stimulatory molecules or inhibitory molecules) and tumor-targeted liposomal gene therapy (crossing the blood-brain-barrier (BBB) to reverse the immunosuppressive microenvironment in the tumor to overcome the unresponsiveness of GBM tumors to checkpoint modulators, including checkpoint inhibitors.

In one embodiment, this invention describes the use of tumor-targeting nanoparticles delivering the tumor suppressor gene p53 to tumor cells to restore p53 function. The tumor suppressor p53 is a transcription factor that regulates cell cycle arrest and apoptosis in response to genotoxic and oncogenic stresses. Given that over 50% of all of human cancers have a mutational inactivation of p53 and alterations in the p53 pathway (15, 16) and p53-null mice are highly predisposed to cancer development (17), restoring p53 function is an attractive cancer therapeutic strategy (18, 19). Understanding of the cellular and molecular processes that link p53 activity to host immune regulation remains incomplete. Nonetheless, recent experimental and clinical results suggest that p53 participates in immune regulation, and that the p53 pathway can be exploited to alter the immunological landscape of tumors for improved cancer therapies (20, 21). Thus, restoring p53 function should boost anti-tumor immunity to augment anti-cancer therapy using molecules that modulate immune checkpoints. However, it is unexpected that restoring p53 function would reduce the toxicities associated with immunotherapy.

SGT-53 is a novel tumor-targeted nanomedicine based on a nanocomplex carrying a plasmid encoding human wild-type p53 (wtp53) for gene therapy. Dynamic Laser Light Scattering (DLS) with a Malvern Zetasizer NanoZS is employed to measure the size of the scL nanocomplexes. Suitably, the size of the complex is less than 400 nm, typically within the range of about 50-400 nm. The zeta-potential, a determinant of the overall charge of the nanocomplex, for these complexes is suitably positive, between about 20 and 50 mV. This proprietary nanodelivery system employed in SGT-53 displays exquisite specificity in delivery of payloads to tumors based on the ability of this nanocomplex to extravasate into the tumor interstitial space and then enter tumor cells via endocytosis mediated by transferrin receptors (TfRs) that are highly elevated on tumor cells including cancer stem cells (26).

The potential of p53 gene therapy to augment checkpoint blockade utilizing a tumor-targeting nanocomplex, SGT-53, in combination with a checkpoint inhibitor (an anti-PD 1 antibody) was examined in several syngeneic mouse tumor models (27). The combination of SGT-53 and the anti-PD 1 antibody resulted in a significantly enhanced inhibition of tumor growth compared to either agent individually in all of the syngeneic mouse tumor models, including breast cancer, non-small cell lung carcinoma, and glioblastoma models. SGT-53 treatment increased immunogenic cell death (ICD) in tumors and enhanced both innate and adaptive immune responses in combination with anti-PD 1, while alleviating tumor-induced immunosuppression.

Unexpectedly, the use of SGT-53 in combination with the immune checkpoint modulator was also found to alleviate the fatal xenogeneic hypersensitivity reaction to an immune checkpoint modulator (an antibody to inhibitory checkpoint molecule PD1) seen in at least one of the syngeneic tumor models (4T1, a model for metastatic breast cancer in BALB/c mice). Thus the use of combining SGT-53 with an immune checkpoint modulator molecule (e.g. anti-PD1 antibody) would not only improve outcomes for cancer patients but also reduce immune-related toxicity and deaths that are seen with such immunotherapies.

The receptor for advanced glycation end products (RAGE) is a multifunctional receptor implicated in diverse processes including inflammation and cancer. RAGE is highly expressed in various cancers and is correlated with poorer outcome in breast and other cancers. RAGE drives tumor progression and metastasis through distinct tumor cell-intrinsic and -extrinsic mechanisms. RAGE expression in breast cancer cells was associated with lymph node and distant metastases in patients with invasive ductal carcinoma, while RAGE-deficient mice displayed a reduced propensity for breast tumor growth.

In another embodiment this invention describes the use of tumor-targeting nanoparticles delivering the tumor suppressor gene RB94 to tumor cells. RB94 is a truncated form of full-length RB 110, a cell cycle regulator and tumor-suppressor originally identified in retinoblastomas (Grant 16, 19). The RB94 protein lacks 112 N-terminal amino acids of the wild-type RB 110 protein. The loss of these amino acids appears to unleash the tumor suppressor activity of RB 110, and RB94 has been shown to induce cytotoxicity in diverse cancer cell types while leaving normal cells unharmed (Grant 19-22). The efficiency of RB94 is not dependent on the presence or absence of RB 110 in the tumors, and RB94 has been shown to induce death in tumor cells that have either wild-type or mutated RB 110 genes (Grant 16, 19). It has been shown that RB94 protein has a longer half-life than RB 110 protein, remains in the active hypo-phosphorylated form for longer time, and causes telomere erosion and chromosomal fragmentation (Grant 20-22). RB 110 is responsible for controlling the cell cycle at the G1/S-checkpoint and thus stands at the crossroads of proliferation, quiescence, senescence, cell differentiation, and apoptosis (Grant 23, 24). Canonically, RB 110 represses the transcription of genes regulated by the E2F family of transcription factors. The binding of hypo-phosphorylated RB 110 to an E2F family member inactivates the transcription factor, preventing the expression of downstream genes that promote cell growth and division (Grant 24, 25). In order for the cell to progress through the G1/S transition, RB 110 must be phosphorylated by cyclin D-CDK4/6 (Grant 26). As stated earlier, it appears that the tumor suppressor function of RB 110 is markedly enhanced by the N-terminal truncation that yields RB94 (Grant 19-21). It is also important to note that due to the differences in RB110 pathways in humans and mice, RB94 is a potent tumor suppressor against human tumors but is not active against mouse tumors (19, 23). Thus, it would be evident to those familiar with the art that there is a major difference between RB 110 and RB94 genes and their protein products. The anti-tumor effect of RB-94 has been established to be through cell cycle arrest in the G2-M phase, increased levels of apoptosis, decreased telomerase activity and chromosomal fragmentation (4, 22). Thus, it is surprising and unexpected that the nanocomplex delivered RB-94 gene (SGT-94 or scL-RB94) enhances the innate anti-tumor immune response in the host and decreases tumor immune evasion as a means of inhibiting tumor cell growth.

The tumor targeting nanoparticle scL-RB94 (also called SGT-94) is composed of a cationic liposome whose surface is decorated with a single-chain antibody fragment recognizing the transferrin receptor (TfR). This targeting moiety enables delivery to a broad range of tumor types that generally all overexpress TfR (17). NSCLCs are among the tumors that overexpress TfR (18). Encapsulated inside the liposome of scL-RB94 is a plasmid carrying the RB94 gene.

Dynamic Laser Light Scattering (DLS) with a Malvern Zetasizer NanoZS is employed to measure the size of the scL-RB94 nanocomplexes. Suitably, the size of the complex is less than 400 nm, typically within the range of about 50-400 nm. The zeta-potential, a determinant of the overall charge of the nanocomplex, for these complexes is suitably positive, between about 20 and 50 mV. The nanodelivery system employed in SGT-94 displays exquisite specificity in delivery of payloads to tumors based on the ability of this nanocomplex to extravasate into the tumor interstitial space and then enter tumor cells via endocytosis mediated by binding to transferrin receptors (TfRs) that are highly elevated on tumor cells including cancer stem cells.

Figures 17A, 17B:
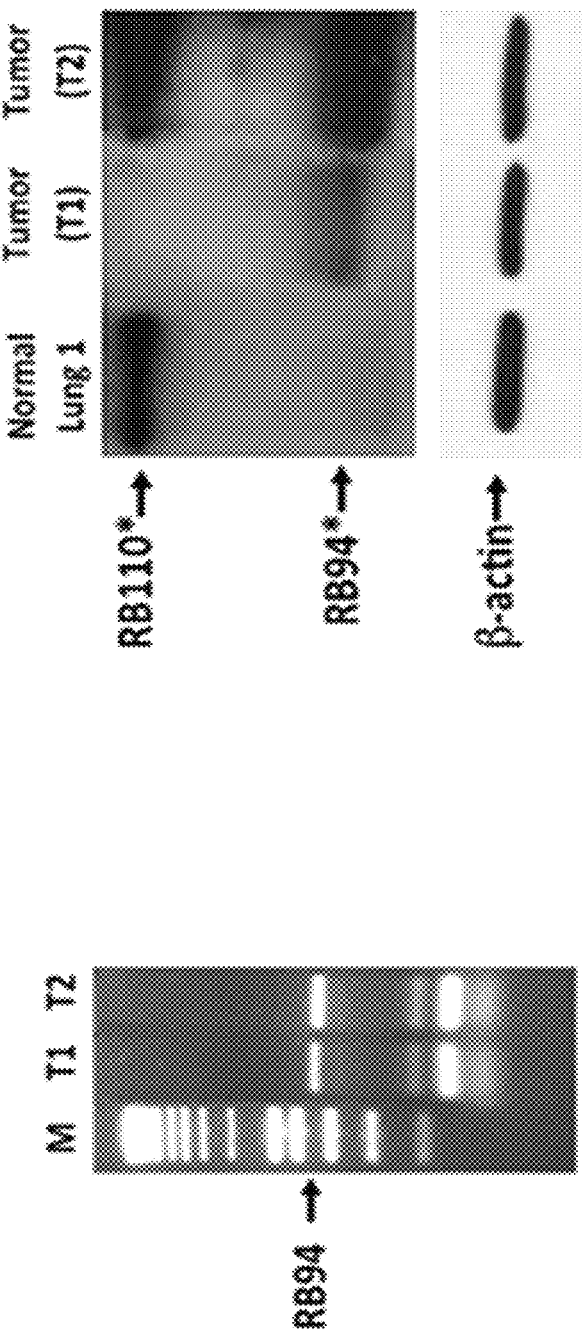
FIG. 17A-17B: Two metastatic tumors (termed T1 & T2) were removed from the lungs of a patient treated with SGT-94 (also called scL-94) in the Phase I trial of SGT-94. The patient's primary tumor was a bladder carcinoma. Each tumor was shown to contain the exogenous RB94 DNA (arrow) detected using RB94-specific primers in DNA PCR (FIG. 17A). Both tumors were expressing RB94 protein as evidenced by western blotting (FIG. 17B) with an antibody that picks up both RB110 and RB94. No RB94 was seen in normal lung. In the smaller tumor (T2) biopsy both RB94 and RB110 were seen with the RB110 likely derived from normal cells in the sample. The western blotting of (3-actin was done as a control for gel loading.

In a completed Phase 1 trial that evaluated SGT-94 (scL-RB94) as single agent in patients with advanced genitourinary cancers, we not only observed a good safety profile for this investigational agent but also saw partial and complete patient responses and disease stabilization (one complete response, two partial responses & three stable diseases in the 11 evaluable patients enrolled in the trial) (Grant 16). In addition to the favorable safety profile and demonstration of anti-tumor activity, we observed that intravenously administered SGT-94 effectively delivered its plasmid payload to metastatic bladder tumor cells in the lungs of one of the patients. Two relatively small (0.5-1.7 cm) tumor nodules (labeled T1 and T2) were removed from the patient's lung and polymerase chain reaction (PCR) was employed to show that the RB94 DNA payload of SGT-94 was present in both metastatic tumors (FIG. 17A). In addition, we demonstrated that the RB94 protein was being expressed in the tumors using western blotting (FIG. 17B). The tumor-targeting specificity of the scL nanocomplex delivery system was confirmed by showing that RB94 protein resulting from the investigational agent, SGT-94 was seen in both T1 and T2, but no RB94 protein was seen in adjacent normal lung tissue. These data demonstrate that in scL-RB94 will be able to reach even relatively small nodules of tumor cells resulting in tumor cell death.

Treatment of mice bearing NSCLC tumors with systemically administered scL-RB94 resulted in tumor regression even after just two systemic treatments (FIG. 18). Immunohistochemical analysis of the tumors revealed a significant increase of apoptotic tumor cells as revealed by TUNEL-positive staining following the scL-RB94 treatment (FIG. 19A). Moreover immunohistochemistry demonstrated the novel finding that RB94 could also induce immunogenic cell death (ICD) as indicated by the increased expression of high-mobility group box 1 (HMGB 1) protein, a marker for ICD (FIG. 19B). Also unexpectedly, quantitative RT-PCR analysis demonstrated that scL-RB94 could upregulate the expression of immune recognition molecules in tumor cells in vitro including the major histocompatibility complex class I (FIGS. 22A and B), T cell activating molecule CD86, programmed death-ligand 1 (PD-L1) (FIG. 23), and NK cell activation ligands (FIG. 20). These unexpected findings indicate that scL-RB94 treatment enhances the host's innate anti-tumor immune response. Treatment with scL-RB94 also decreases tumor immune evasion by shifting the polarization of tumor-associated macrophages from pro-tumoral M2 macrophages to anti-tumoral M1 macrophages (FIG. 21). Another unexpected finding was that after scL-RB94 treatment, a significant increase of CD45 immune cells (FIG. 25A), activated NK cells (FIG. 25B) and mature dendritic cells (FIG. 25C) was observed to be infiltrating the tumor. Collectively, these findings demonstrate that the observed anti-tumor efficacy of scL-RB94 in patients is also unexpectedly due, at least in part, to an enhancement of anti-tumoral innate immunity.

In embodiments a human wild type p53 tumor suppressor gene is used in combination with a molecule that modulates immune checkpoints to treat disease.

In another embodiment a targeted cationic liposomal complex for delivery of the human RB94 tumor suppressor gene is used alone or in combination with a molecule that modulates immune checkpoints to treat disease.

As used herein "in combination" refers to methods where the liposomal complexes and the immune checkpoint modulator are administered at the same time, roughly the same time, or within a specific time span, and can include co-administration of both therapies, or administration of one therapy before or after the other (usually within a few minutes to a few hours to a few days). In combination includes delivery of the liposomal complex in one administration, followed by (or before) administration of the immune checkpoint modulator in a second administration.

Methods for delivering the immune checkpoint modulator are described herein and known in the art, and can include administration of an antibody against A2AR, B7-H3, B7-H4, BTLA, CTLA-4, IDO, KIR, LAG3, PD-1, PD-L1, PD-L2, TIM-3, VISTA (protein), TIGIT (T cell Ig and ITIM domain), CD47, or SIRPalpha via injection, inhalation, etc., The immune checkpoint modulator can also be delivered via a cationic liposomal nanocomplex, if desired, and can be included in the same cationic liposomal complex that includes the nucleic acid or a different cationic liposomal nanocomplex.

In preferred embodiments the antibodies are an anti PD-1 antibody, anti PD-L1, or an anti CTLA-4 antibody.

In embodiments these diseases include but are not limited to cancer, rheumatoid arthritis, autoimmune diseases, sepsis and meningitis, lupus, Achalasia, Addison's disease, Adult Still's disease, Agammaglobulinemia, Alopecia areata, Amyloidosis, Ankylosing spondylitis, Anti-GBM/Anti-TBM nephritis, Antiphospholipid syndrome, Autoimmune angioedema, Autoimmune dysautonomia, Autoimmune hepatitis, Autoimmune inner ear disease (AIED), Autoimmune myocarditis, Autoimmune oophoritis, Autoimmune orchitis, Autoimmune pancreatitis, Autoimmune retinopathy, Autoimmune urticarial, Axonal & neuronal neuropathy (AMAN), Baló disease, Behcet's disease, Benign mucosal pemphigoid, Benign Multiple Sclerosis, Bullous pemphigoid, Castleman disease (CD), Celiac disease, Chagas disease, Chronic inflammatory demyelinating polyneuropathy (CIDP), Chronic recurrent multifocal osteomyelitis (CRMO), Churg-Strauss Syndrome (CSS) or Eosinophilic Granulomatosis (EGPA), Cicatricial pemphigoid, Cogan's syndrome, Cold agglutinin disease, Congenital heart block, Coxsackie myocarditis, CREST syndrome, Crohn's disease, Dermatitis herpetiformis, Dermatomyositis, Devic's disease (neuromyelitis optica), Discoid lupus, Dressler's syndrome, Endometriosis, Eosinophilic esophagitis (EoE), Eosinophilic fasciitis, Erythema nodosum, Essential mixed cryoglobulinemia, Evans syndrome, Fibromyalgia, Fibrosing alveolitis, Gastritis, Giant cell arteritis (temporal arteritis), Giant cell myocarditis, Goodpasture's syndrome, Granulomatosis with Polyangiitis, Graves' disease, Guillain-Barre syndrome, Hemolytic anemia, Henoch-Schonlein purpura (HSP), Herpes gestationis or pemphigoid gestationis (PG), Hidradenitis Suppurativa (HS) (Acne Inversa), Hypogammalglobulinemia, IgA Nephropathy, IgG4-related sclerosing disease, Immune thrombocytopenic purpura (ITP), Inclusion body myositis (IBM), Inflammatory Bowel Disease, Juvenile arthritis, Juvenile myositis (JM), Kawasaki disease, Lambert-Eaton syndrome, Leukocytoclastic vasculitis, Lichen planus, Lichen sclerosis, Ligneous conjunctivitis, Linear IgA disease (LAD), Lupus, Lyme disease chronic, Meniere's disease, Microscopic polyangiitis (MPA), Mixed connective tissue disease (MCTD), Mooren's ulcer, Mucha-Habermann disease, Multifocal Motor Neuropathy (MMN) or MMNCB, Multiple sclerosis, Myasthenia gravis, Myositis, Narcolepsy, Neonatal Lupus, Neuromyelitis optica, Neutropenia, Ocular cicatricial pemphigoid, Optic neuritis, Palindromic rheumatism (PR), PANDAS (OCD), Paraneoplastic cerebellar degeneration (PCD), Paroxysmal nocturnal hemoglobinuria (PNH), Parry Romberg syndrome, Pars planitis (peripheral uveitis), Parsonage-Turner syndrome, Pemphigus, Peripheral neuropathy, Perivenous encephalomyelitis, Pernicious anemia (PA), POEMS syndrome, Polyarteritis nodosa, Polyglandular syndromes type [I, II, III,], Polymyalgia rheumatic, Polymyositis, Postmyocardial infarction syndrome, Postpericardiotomy syndrome, Primary biliary cirrhosis, Primary sclerosing cholangitis, Progesterone dermatitis, Psoriasis, Psoriatic arthritis, Pure red cell aplasia (PRCA), Pyoderma gangrenosum, Raynaud's phenomenon, Reactive Arthritis, Reflex sympathetic dystrophy, Relapsing polychondritis, Restless legs syndrome (RLS), Retroperitoneal fibrosis, Rheumatic fever, Sarcoidosis, Schmidt syndrome, Scleritis, Scleroderma, Sjögren's syndrome, Sperm & testicular autoimmunity, Stiff person syndrome (SPS), Subacute bacterial endocarditis (SBE), Susac's syndrome, Sympathetic ophthalmia (SO), Systemic Lupus Erythematosus, Systemic Sclerosis, Takayasu's arteritis, Temporal arteritis/Giant cell arteritis, Thrombocytopenic purpura (TTP), Tolosa-Hunt syndrome (THS), Transverse myelitis, Ulcerative colitis (UC), Undifferentiated connective tissue disease (UCTD), Uveitis, Vasculitis, Vitiligo, Vogt-Koyanagi-Harada Disease, Wegener's Granulomatosis.

In preferred embodiments the disease is cancer, suitably the cancer being treated is, but is not limited to, a primary or metastatic breast cancer, including inflammatory breast cancer, invasive ductal carcinoma, etc.

In other embodiments the disease is cancer, suitably the cancer being treated is, but is not limited to, a primary or metastatic lung cancer, including NSCLC.

In other embodiments, the cancer being treated is, but is not limited to, a primary or metastatic brain tumor, neuroendocrine tumors, melanoma, pancreatic, prostate, bladder, head and neck, ovarian, kidney, liver, vaginal, urogenital, gastric, colorectal, cervical, liposarcoma, angiosarcoma, rhabdomyosarcoma, choriocarcinoma, retinoblastoma, multiple myeloma and other types of cancer.

In embodiments, the method of preparing the targeted cationic liposomal complex, i.e., the nucleic acid delivery systems described herein, suitably comprise preparing a lipid solution comprising one or more cationic lipids in ethanol, injecting the mixture of lipids into an aqueous solution, thereby forming a cationic liposome, mixing the cationic liposome with a ligand to form the targeted cationic liposome, wherein the ligand is directly complexed with, but not chemically conjugated to, the cationic liposome. The ligand can be an antibody or antibody fragment. The antibody or antibody fragment is mixed with the cationic liposome at room temperature and at a protein:lipid ratio in the range of about 1:20 to about 1:40 (w:w).

Methods for preparing the ligand-targeted cationic liposome complexes are described, for example, in U.S. 2005/0002998, the disclosure of which is incorporated by reference herein in its entirety.

It has been unexpectedly found that no extrusion or sonication is required to form the liposomes and the targeted cationic liposomes having the desired size and Zeta Potential characteristics, according to the methods described herein. In embodiments, evaporation, sonication, milling and/or extrusion of the liposomes is specifically excluded from the disclosed methods. In further embodiments, the methods of preparing targeted cationic liposomes described throughout suitably consist of or consist essentially of the recited elements. In such embodiments, addition of steps such as evaporation, sonication and/or extrusion, are considered a material alteration to such methods and thus are specifically excluded from such methods that consist essentially of the recited elements.

For example, in embodiments, the nucleic acid is a gene, polynucleotide, such as plasmid DNA, DNA fragment, oligonucleotide, oligodeoxynucleotide, antisense oligonucleotide, chimeric RNA/DNA oligonucleotide, RNA, siRNA, ribozyme, viral particle, growth factor, cytokine, immunomodulating agent, or other protein, including proteins which when expressed present an antigen which stimulates or suppresses the immune system. Preferred therapeutic agents are nucleic acid molecules, preferably DNA or siRNA molecules. A preferred DNA molecule is one which encodes a gene such as a wild type p53 molecule, an Rb94 molecule, an Apoptin molecule, an EGFG molecule or an antisense molecule. A preferred HER-2 antisense oligonucleotide is against the HER-2 gene and has the sequence 5'-TCC ATGGTG CTC ACT-3'. A preferred siRNA molecule is one which acts against HER-2 mRNA. Other preferred therapeutic molecules can be determined by one of ordinary skill in the art without undue experimentation.

The ligand can be any ligand the receptor for which is differentially expressed on the target cell. Examples include transferrin, folate, other vitamins, EGF, insulin, Heregulin, RGD peptides or other polypeptides reactive to integrin receptors, antibodies or their fragments. A preferred antibody fragment is a single chain Fv fragment of an antibody. The antibody or antibody fragment is one which will bind to a receptor on the surface of the target cell, and preferably to a receptor that is differentially expressed on the target cell. One preferred antibody is an anti-TfR monoclonal antibody and a preferred antibody fragment is a scFv based on an anti-TfR monoclonal antibody. Another preferred antibody is an anti-HER-2 monoclonal antibody, and another preferred antibody fragment is a scFv based on an anti-HER-2 monoclonal antibody.

The ligand is mixed with the liposome at room temperature and at a ligand:liposome ratio in the range of about 1:0.001 to 1:500 (w:w), preferably about 1:10 to about 1:50 (w:w).

Nucleic acid is mixed with the cationic liposome at room temperature and at an agent:lipid ratio in the range of about 1:0.1 to about 1:50 (µg:nmole), preferably about 1:10 to about 1:24 (µg:nmole). In complexes, for example, in which the ligand is transferrin and the nucleic acid is plasmid DNA, useful ratios of nucleic to liposome to ligand typically are within the range of about 1 µg:nmole:0.1-50 nmoles: 0.1-100 µg, preferably 1 µg: 5-24 nmoles:6-36 µg, most preferably about 1 µg: 10 nmoles: 12.5 µg. If the ligand is TfRscFv, useful ratios of ligand to liposome typically are within the range of about 1:5 to 1:40 (µg: µg), preferably 1:30 (µg: µg), and the ratio of plasmid DNA to liposome typically is within the range of about 1:6 to 1:20 (µg: µg), preferably 1:10 (µg: µg). If the therapeutic agent is an oligonucleotide (ODN) rather than plasmid DNA, typical ratios of ligand, liposome and the ODN are 0.1 nmole to 36 nmole (ODN:liposome) and 0.1 µg to 100 µg (ligand: liposome), preferably 0.5 nmoles to 20 nmoles (ODN: liposome) and 0.5 µg to 50 µg (ligand:liposome), most preferably 1 nmole to 15 nmole (ODN:liposome) and 1 µg to 30 µg (ligand:liposome). If the therapeutic agent is an siRNA, useful ratios of the components can be 0.1 µg to 30 nmole(siRNA:liposome) and 0.1 µg to 100 µg (TfRscFv:

liposome), preferably 1 µg to 7 nmole (siRNA:lipsosome) and 1 µg to 30 µg (TfRscFv:liposome).

In a further embodiment, the molar ratio of nucleic acid molecules to liposome complex is in the range of about 0.5:1 to about 1:40 (µg total nucleic acid: µg liposome), or about 1:1 to about 1:40 (µg total nucleic acid: µg liposome), suitably about 1:5 to about 1:20 (µg total nucleic acid: µg liposome), more suitably about 1:10 (µg total nucleic acid: µg liposome).

A wide variety of cationic liposomes are useful in the preparation of the complexes. Published PCT application WO99/25320, incorporated herein by reference, describes the preparation of several cationic liposomes. Examples of desirable liposomes include those that comprise a mixture of dioleoyltrimethylammonium phosphate (DOTAP) and dioleoylphosphatidylethanolamine (DOPE) and/or cholesterol (chol), or a mixture of dimethyldioctadecylammonium bromide (DDAB) and DOPE and/or cholesterol, or a mixture of dimethyldioctadecylammonium bromide (DDAB) and DOPE, or a mixture of dioleoyltrimethylammonium phosphate (DOTAP) and dioleoylphosphatidylethanolamine (DOPE). The ratio of the lipids can be varied to optimize the efficiency of uptake of the therapeutic molecule for the specific target cell type. The liposome can comprise a mixture of one or more cationic lipids and one or more neutral or helper lipids. A desirable ratio of cationic lipid(s) to neutral or helper lipid(s) is about 1:(0.5-3), preferably 1:(1-2) (molar ratio).

In the preferred embodiment the nucleic acid encodes a tumor suppressor protein. In embodiments, the tumor suppressor protein is p53, including human wild-type p53.

In other embodiments the tumor suppressor protein is RB94.

In one preferred embodiment, methods of treating cancer in a patient, comprises administering to the patient a targeted cationic liposome complex comprising a plasmid DNA expressing wild-type p53 gene. The methods further comprise administering a modifier of an inhibitory checkpoint molecule or stimulatory checkpoint molecule.

In another preferred embodiment, methods of treating cancer in a patient, comprises administering to the patient a targeted cationic liposome complex comprising a plasmid DNA expressing the RB94 gene. The methods may further comprise administering a modifier of an inhibitory checkpoint molecule or stimulatory checkpoint molecule.

In other embodiments, methods of treating cancer in a patient, comprising administering to the patient a targeted cationic liposome complex comprising a plasmid DNA expressing another gene or gene that that has immunomodulatory activity. The methods further comprise administering a modifier of an inhibitory checkpoint molecule or stimulatory checkpoint molecule.

In embodiments, these inhibitory checkpoint molecules include, but are not limited to, A2AR, B7-H3, B7-H4, BTLA, CTLA-4, IDO, KIR, LAG3, PD-1, PD-L1, PD-L2, TIM-3, VISTA (protein), TIGIT (T cell Ig and ITIM domain), CD47, and SIRPalpha.

In other embodiments these stimulatory checkpoint molecules include, but are not limited to, CD27, CD28, CD40, CD122, CD137, OX40, GITR, and ICOS.

Drugs or drug candidates that inhibit/block the inhibitory checkpoint molecules are sometimes known as checkpoint inhibitors; this idea is often referred to as immune checkpoint blockade, or simply checkpoint blockade (3, 28). Checkpoint inhibitor drugs have seen growth in pharmaceutical research in cancer by companies including Bristol-Myers Squibb, Merck, Roche and AstraZeneca.

In further embodiments methods of treating other immune related diseases in a patient comprise administering to the patient a targeted cationic liposome complex comprising a plasmid DNA expressing wild-type p53 gene or the RB94 gene. The methods further comprise administering a modifier of an inhibitory checkpoint molecule or stimulatory checkpoint molecule.

In other embodiments, methods of treating other immune related diseases in a patient, comprising administering to the patient a targeted cationic liposome complex comprising a nucleic acid, suitably a plasmid DNA expressing another gene or gene that that has immunomodulatory activity. The methods further comprise administering a modifier of an inhibitory checkpoint molecule or stimulatory checkpoint molecule.

In other embodiments, the SGT-53 nanocomplex can be used to target the cell surface receptor RAGE to treat cancer (primary and metastatic) and other diseases including inflammation.

In embodiments, the administration is intravenous (IV), intratumoral (IT), intralesional (IL), aerosal, percutaneous, oral, endoscopic, topical, intramuscular (IM), intradermal (ID), intraocular (IO), intraperitoneal (IP), sublingual (SL), transdermal (TD), intranasal (IN), intracerebral (IC), intra-organ (e.g. intrahepatic), slow release implant, or subcutaneous administration, or via administration using an osmotic or mechanical pump.

In additional embodiments, provided herein are methods of treating a disease in a patient, comprising: providing a ligand-targeted cationic liposomal complex, comprising: a cationic liposome; a targeting ligand that is complexed with the cationic liposome, but is not chemically conjugated to the cationic liposome, and wherein the targeting ligand does not comprise a lipid tag; and a nucleic acid encoding RB94; and administering the ligand-targeted cationic liposomal complex in combination with an immune checkpoint modulator to the patient to treat the disease.

Suitably, the disease is a cancer, including wherein the cancer is a primary or metastatic brain tumor, a breast cancer, a neuroendocrine tumor, a melanoma, a pancreatic cancer, a prostate cancer, a head and neck cancer, an ovarian cancer, a lung cancer, a bladder cancer, a kidney cancer, a liver cancer, a vaginal cancer, a urogenital cancer, a gastric cancer, a colorectal cancer, a cervical cancer, a liposarcoma, an angiosarcoma, a rhabdomyosarcoma, a choriocarcinoma, a retinoblastoma, and a multiple myeloma. In embodiments, the lung cancer is a Non small cell lung cancer (NSCLC), an Adenocarcinoma; a Squamous cell carcinoma, a Large cell carcinoma, a Small Cell Lung Cancer. Suitably, the breast cancer is a primary or metastatic breast cancer, an inflammatory breast cancer, a Ductal Carcinoma In Situ (DCIS), invasive ductal carcinoma (IDC) including IDC Type: Tubular Carcinoma of the Breast, IDC Type: Medullary Carcinoma of the Breast, IDC Type: Mucinous Carcinoma of the Breast, IDC Type: Papillary Carcinoma of the Breast, IDC Type: Cribriform Carcinoma of the Breast, as well as Invasive Lobular Carcinoma (ILC), Lobular Carcinoma In Situ (LCIS), Male Breast Cancer, Molecular Subtypes of Breast Cancer, Paget's Disease of the Nipple, Phyllodes Tumors of the Breast, and Metastatic Breast Cancer. In embodiments, the breast cancer is an inflammatory breast cancer Suitably, the disease is an immune related disease.

In embodiments, the immune checkpoint modulator is an inhibitor checkpoint molecule, and in embodiments, the inhibitor checkpoint modulator is selected from the group consisting of A2AR, B7-H3, B7-H4, BTLA, CTLA-4, IDO, KIR, LAG3, PD-1, PD-L1, PD-L2, TIM-3, VISTA (protein), TIGIT (T cell Ig and ITIM domain), CD47, and SIRPalpha. Suitably, the immune checkpoint modulator is a stimulatory check point molecule. Including, the stimulatory check point molecule is selected from the group consisting of CD27, CD28, CD40, CD122, CD137, OX40, GITR, and ICOS.

In embodiments, the ligand is a single chain Fv antibody fragment, including wherein the single chain Fv antibody fragment is an anti-transferrin receptor single chain Fv (TfRscFv).

In embodiments, the ligand-targeted cationic liposomal complex is administered via intravenous (IV), intratumoral (IT), intralesional (IL), aerosal, percutaneous, oral, endoscopic, topical, intramuscular (IM), intradermal (ID), intraocular (IO), intraperitoneal (IP), sublingual (SL), transdermal (TD), intranasal (IN), intracereberal (IC), intraorgan (e.g. intrahepatic), slow release implant, subcutaneous administration, or via administration using an osmotic or mechanical pump.

In further embodiments, provided herein is a method of reducing the toxic side effects of an immune checkpoint modulator in a patient, comprising: providing a ligand-targeted cationic liposomal complex, comprising: a cationic liposome; a targeting ligand that is complexed with the cationic liposome, but is not chemically conjugated to the cationic liposome, and wherein the targeting ligand does not comprise a lipid tag; and a nucleic acid encoding RB94; and administering the ligand-targeted cationic liposomal complex in combination with an immune checkpoint modulator to the patient, wherein the side effects of the immune checkpoint modulator are reduced or eliminated.

Suitably, the immune checkpoint modulator is an inhibitor checkpoint molecule, including wherein the inhibitor checkpoint modulator is selected from the group consisting of A2AR, B7-H3, B7-H4, BTLA, CTLA-4, IDO, KIR, LAG3, PD-1, PD-L1, PD-L2, TIM-3, VISTA (protein), TIGIT (T cell Ig and ITIM domain), CD47, and SIRPalpha. In embodiments, the inhibitor checkpoint modulator is an anti-PD1 antibody. In embodiments, the immune checkpoint modulator is a stimulatory check point molecule. Suitably, the stimulatory check point molecule is selected from the group consisting of CD27, CD28, CD40, CD122, CD137, OX40, GITR, and ICOS.

Suitably, the ligand is a single chain Fv antibody fragment, including wherein the single chain Fv antibody fragment is an anti-transferrin receptor single chain Fv (TfRscFv).

Suitably, the side effects are reduced in a patient undergoing treatment for a cancer. In embodiments, the cancer is a primary or metastatic brain tumor, a breast cancer, a neuroendocrine tumor, a melanoma, a pancreatic cancer, a prostate cancer, a head and neck cancer, an ovarian cancer, a lung cancer, a kidney cancer, a liver cancer, a vaginal cancer, a urogenital cancer, a gastric cancer, a bladder cancer, a colorectal cancer, a cervical cancer, a liposarcoma, an angiosarcoma, a rhabdomyosarcoma, a choriocarcinoma, a retinoblastoma, and a multiple myeloma. Suitably, the lung cancer is a Non small cell lung cancer (NSCLC), an Adenocarcinoma; a Squamous cell carcinoma, a Large cell carcinoma, a Small Cell Lung Cancer In embodiments, the breast cancer is a primary or metastatic breast cancer, an inflammatory breast cancer, a Ductal Carcinoma In Situ (DCIS), invasive ductal carcinoma (IDC) including IDC Type: Tubular Carcinoma of the Breast, IDC Type: Medullary Carcinoma of the Breast, IDC Type: Mucinous Carcinoma of the Breast, IDC Type: Papillary Carcinoma of the Breast, IDC Type: Cribriform Carcinoma of the Breast, as well as Invasive Lobular Carcinoma (ILC), Lobular Carcinoma In Situ (LCIS), Male Breast Cancer, Molecular Subtypes of Breast Cancer, Paget's Disease of the Nipple, Phyllodes Tumors of the Breast, and Metastatic Breast Cancer. Suitably, the breast cancer is an inflammatory breast cancer In embodiments, the patient is undergoing treatment for an immune related disease.

In embodiments, the side effect is a xenogeneic hypersensitivity reaction.

Suitably, the ligand-targeted cationic liposomal complex is administered via intravenous (IV), intratumoral (IT), intralesional (IL), aerosal, percutaneous, oral, endoscopic, topical, intramuscular (IM), intradermal (ID), intraocular (IO), intraperitoneal (IP), sublingual (SL), transdermal (TD), intranasal (IN), intracereberal (IC), intraorgan (e.g. intrahepatic), slow release implant, subcutaneous administration, or via administration using an osmotic or mechanical pump.

Also provided herein is a method of treating a cancer expressing a receptor for advanced glycation end products (RAGE), in a patient, comprising: providing a ligand-targeted cationic liposomal complex, comprising: a cationic liposome; a targeting ligand that is complexed with the cationic liposome, but is not chemically conjugated to the cationic liposome, and wherein the targeting ligand does not comprise a lipid tag; and a nucleic acid encoding RB94; and administering the ligand-targeted cationic liposomal complex to the patient to reduce the RAGE expression and treat the cancer.

Suitably, the cancer is a primary or metastatic brain tumor, a breast cancer, a neuroendocrine tumor, a melanoma, a pancreatic cancer, a prostate cancer, a head and neck cancer, an ovarian cancer, a lung cancer, a bladder cancer, a kidney cancer, a liver cancer, a vaginal cancer, a urogenital cancer, a gastric cancer, a colorectal cancer, a cervical cancer, a liposarcoma, an angiosarcoma, a rhabdomyosarcoma, a choriocarcinoma, a retinoblastoma, and a multiple myeloma. In embodiments, the lung cancer is a Non small cell lung cancer (NSCLC), an Adenocarcinoma; a Squamous cell carcinoma, a Large cell carcinoma, a Small Cell Lung Cancer. In embodiments, the breast cancer is a primary or metastatic breast cancer, an inflammatory breast cancer, a Ductal Carcinoma In Situ (DCIS), invasive ductal carcinoma (IDC) including IDC Type: Tubular Carcinoma of the Breast, IDC Type: Medullary Carcinoma of the Breast, IDC Type: Mucinous Carcinoma of the Breast, IDC Type: Papillary Carcinoma of the Breast, IDC Type: Cribriform Carcinoma of the Breast, as well as Invasive Lobular Carcinoma (ILC), Lobular Carcinoma In Situ (LCIS), Male Breast Cancer, Molecular Subtypes of Breast Cancer, Paget's Disease of the Nipple, Phyllodes Tumors of the Breast, and Metastatic Breast Cancer. Suitably, the breast cancer is an inflammatory breast cancer In embodiments, the ligand is a single chain Fv antibody fragment, including wherein the single chain Fv antibody fragment is an anti-transferrin receptor single chain Fv (TfRscFv).

Suitably the ligand-targeted cationic liposomal complex is administered via intravenous (IV), intratumoral (IT), intralesional (IL), aerosal, percutaneous, oral, endoscopic, topical, intramuscular (IM), intradermal (ID), intraocular (IO), intraperitoneal (IP), sublingual (SL), transdermal (TD), intranasal (IN), intracereberal (IC), intraorgan (e.g. intrahepatic), slow release implant, subcutaneous administration, or via administration using an osmotic or mechanical pump.

In embodiments, the method inhibits the development of metastatic disease.

In further embodiments, provided herein is a method of treating a cancer in a patient, comprising: providing a ligand-targeted cationic liposomal complex, comprising: a cationic liposome; a targeting ligand that is complexed with the cationic liposome, but is not chemically conjugated to the cationic liposome, and wherein the targeting ligand does not comprise a lipid tag; and a nucleic acid encoding RB94 or p53; and administering the ligand-targeted cationic liposomal complex in combination with an immune checkpoint modulator and a chemotherapeutic agent to the patient to treat the disease.

In embodiments, the cancer is a primary or metastatic brain tumor, a breast cancer, a neuroendocrine tumor, a melanoma, a pancreatic cancer, a prostate cancer, a head and neck cancer, an ovarian cancer, a lung cancer, a bladder cancer, a kidney cancer, a liver cancer, a vaginal cancer, a urogenital cancer, a gastric cancer, a colorectal cancer, a cervical cancer, a liposarcoma, an angiosarcoma, a rhabdomyosarcoma, a choriocarcinoma, a retinoblastoma, and a multiple myeloma. Suitably, the lung cancer is a Non small cell lung cancer (NSCLC), an Adenocarcinoma; a Squamous cell carcinoma, a Large cell carcinoma, a Small Cell Lung Cancer. Suitably, the breast cancer is a primary or metastatic breast cancer, an inflammatory breast cancer, a Ductal Carcinoma In Situ (DCIS), invasive ductal carcinoma (IDC) including IDC Type: Tubular Carcinoma of the Breast, IDC Type: Medullary Carcinoma of the Breast, IDC Type: Mucinous Carcinoma of the Breast, IDC Type: Papillary Carcinoma of the Breast, IDC Type: Cribriform Carcinoma of the Breast, as well as Invasive Lobular Carcinoma (ILC), Lobular Carcinoma In Situ (LCIS), Male Breast Cancer, Molecular Subtypes of Breast Cancer, Paget's Disease of the Nipple, Phyllodes Tumors of the Breast, and Metastatic Breast Cancer. In embodiments, the breast cancer is an inflammatory breast cancer Suitably, the immune checkpoint modulator is an inhibitor checkpoint molecule. In embodiments, the inhibitor checkpoint modulator is selected from the group consisting of A2AR, B7-H3, B7-H4, BTLA, CTLA-4, IDO, KIR, LAG3, PD-1, PD-L1, PD-L2, TIM-3, VISTA (protein), TIGIT (T cell Ig and ITIM domain), CD47, and SIRPalpha. Suitably, the immune checkpoint modulator is a stimulatory check point molecule, including wherein the stimulatory check point molecule is selected from the group consisting of CD27, CD28, CD40, CD122, CD137, OX40, GITR, and ICOS.

Suitably, ligand is a single chain Fv antibody fragment, including wherein the single chain Fv antibody fragment is an anti-transferrin receptor single chain Fv (TfRscFv).

In embodiments, the ligand-targeted cationic liposomal complex is administered via intravenous (IV), intratumoral (IT), intralesional (IL), aerosal, percutaneous, oral, endoscopic, topical, intramuscular (IM), intradermal (ID), intraocular (IO), intraperitoneal (IP), sublingual (SL), transdermal (TD), intranasal (IN), intracereberal (IC), intraorgan (e.g. intrahepatic), slow release implant, subcutaneous administration, or via administration using an osmotic or mechanical pump.

In embodiments, the chemotherapeutic agent is selected from the group consisting of cisplatin, carboplatin, docetaxel, gemcitabine, paclitaxel, vinorelbine, and pemetrexed.

EXAMPLES

Example 1

Preparation of Targeted Cationic Liposome DNA Complex

It has been determined that a simple mixing of the TfRscFv and the cationic liposome (which does not contain any lipid with a reducible group such as Maleimide DOPE or any reducible group), instead of chemical conjugation, results in formation of an immunologically active complex, wherein the ligand is bound directly to the liposome without the use of a linker or chemical-conjugation molecule, that still efficiently binds to and transfects tumor cells (see e.g., U.S. Published Patent Application No. 2003/0044407, the disclosure of which, including the compositions and methods disclosed therein, is incorporated by reference herein).

The TfRscFv-immunoliposome complexes are prepared by mixing the TfRscFv with the cationic liposome composition at defined ratios of single chain protein to liposome and DNA to n moles (or ug) total lipid in the mixed complex in the ranges described throughout. The preparation of the complexes described below in subsequent Examples was in accordance with the following general procedure.

The ligand is mixed with the liposome at room temperature and at a ligand:liposome ratio in the range of about 1:0.001 to 1:500 (ug:nmole), preferably about 1:10 to about 1:50 (ug:nmole). The therapeutic agent is mixed with the cationic liposome at room temperature and at an agent:lipid ratio in the range of about 1:01 to about 1:50 (ug:nmole), preferably about 1:10 to about 1:24 (ug:nmole). In complexes, for example, in which the ligand is transferrin and the therapeutic agent is plasmid DNA, useful ratios of therapeutic agent to liposome to ligand typically are within the range of about 1 ug: 0.1-50 nmoles: 0.1-100 ug, preferably 1 ug: 5-24 nmoles:6-36 ug, most preferably about 1 ug: 10 nmoles: 12.5 ug. If the ligand is TfRscFv, useful ratios of ligand to liposome typically are within the range of about 1:5 to 1:40 (ug:ug), preferably 1:30 (ug:ug), and the ratio of plasmid DNA to liposome typically is within the range of about 1:6 to 1:20 (ug:ug), preferably 1:10 (ug:ug).

Exemplary lipid compositions include:

| LipA | DOTAP/DOPE | 1:1 molar ratio |
|------|------------|-----------------|
| LipB | DDAB/DOPE | 1:1 molar ratio |
| LipC | DDAB/DOPE | 1:2 molar ratio |
| LipD | DOTAP/Chol | 1:1 molar ratio |
| LipE | DDAB/Chol | 1:1 molar ratio |
| LipG | DOTAP/DOPE/Chol | 2:1:1 molar ratio |
| LipH | DDAB/DOPE/Chol | 2:1:1 molar ratio |

More specifically, the appropriate amount of 2 mM liposome (A-H described above) is mixed with any water (e.g., DI water) if required to give a desired volume and inverted to mix. To the liposome-water mixture, the appropriate amount of TfRscFv is added to give the desired ratio and mixed by gentle inversion for about 1 second to about 2 minutes. This mixture is kept at room temperature for about 10 minutes to about 20 minutes (inverted gently for 5-10 seconds after approximately 5 minutes). At the same time, the appropriate amount of DNA is mixed by inversion for about 1 second to about 2 minutes with any water required to give a desired volume or concentration. Typically, for use in an in vitro assay, it is desirable that the concentration of DNA is in the range of about 0.01 μg to about 10 μg per well; for in vivo use, it is desirable to provide about 5 μg to about 100 µg of DNA per injection. The DNA solution is quickly added to the TfRscFv-liposome solution and the mixture is inverted for about 1 second to about 2 minutes. The final mixture is kept at room temperature for about 10 minutes to about 20 minutes, gently inverting for 5-10 seconds after approximately 5 minutes. For in vitro experiments, the targeted cationic liposome nanocomplex carrying plasmid DNA, e.g. the wt p53 gene or the RB94 gene, is further diluted with serum-free media (SFM). For use in vivo 50% dextrose or 50-70% sucrose is added to a final concentration of 1-20% (V:V), suitably 5-20% (V:V) and mixed by gentle inversion for about 1 second to about 2 minutes. A specific example at a suitable ratio of 1:30 (TfRscFv:liposome, w:w) and 1:14 (µg DNA:n mole total Lipid) is as follows. For 40 µg of DNA in a final volume of 800 µl, mix 183 µl water with 280 µl of 2 mM liposome solution. Add 34 µl of TfRscFv (with a concentration of 0.4 µg/ml). Mix 183 µl water with 40 µl of 1 µg/1 µl DNA. Add 80 µl of 50% Dextrose as the last step.

For in vitro experiments, SGT-53 or SGT-94 is further diluted with serum-free media (SFM). For animal injections, 5-10% dextrose or sucrose was added to the SGT-53 or SGT-94 preparation.

The SGT-53 or SGT-94 nanocomplex can be used immediately after preparation or lyophilized to dryness and stored at −20 to 8° C. and stored prior to use. If lyophilized, SGT-53 is reconstituted by the addition of an amount of sterile, endotoxin free water equivalent to the original volume prior to lyophilization. After swirling for 30 sec to 1 min to dissolve. The vial is sonicated in a bath sonicator at 37 kHz, 100% power for 1 to 10 minutes at 31-34° C. The vial is swirled gently every 30-60 sec during the sonication.

The size (number average) of the final complex prepared by the methods is between about 10 to 800 nm, suitably about 50 to 400 nm, most suitably about 25 to 200 nm with a zeta potential of between about 1 and 100 mV, more suitably 10 to 60 mV and most suitably 20 to 50 mV as determined by dynamic light scattering using a Malvern Zetasizer ZS. This size is small enough to efficiently pass through the tumor capillary bed and reach tumor cells, and also small enough to efficiently pass through the capillary bed and reach the target APC cells.

For example, using the method described above, the size and zeta potential of SGT-53 and SGT-94 were determined by dynamic light scattering at 25° C. with a Zetasizer Nano ZS System (Malvern Instruments). The mean particle size (number average) in water was in the range of 100-125 nm (e.g. 114.4±8.4 nm). The mean zeta potential of SGT-53 was in the range of 25 to 30 mV (e.g. 28.2±1.2 mV).

Example 2

SGT-53 Increases Immunogenicity of 4T1 Cells

4T1 cells were plated at $6.0 \times 10^5$ cells per 10 cm dish for 24 h before transfection. scL-53 (SGT-53) was prepared as described above in Example 1 and added in SFM to the dishes at a concentration of 7 µg of DNA/dish. As a control treatment, scL-GFP or scL-vec nanocomplexes were prepared using either GFP expression plasmid pCMV-GFP or empty plasmid pCMV, respectively. After incubation for 4 h at 37° C., the medium was replaced with complete medium which includes serum, and the cells were further incubated. At the indicated time after treatment, cells were collected for analysis.

Following exposure of 4T1 mouse breast cancer cells in culture to a tumor-targeting liposome complex (nanocomplex) loaded with a plasmid encoding human wtp53 (SGT-53) or with an empty vector control plasmid (scL-vec) (7 ug DNA/dish), quantitative RT-PCR was performed to assess expression of human p53 (FIG. 1A) as well as mouse genes associated with immune responses (FIG. 1B). A high level of human p53 mRNA (>3 logs above the background signal of untreated cells when normalized to mouse GAPDH) was detected at 24, 48, and 72 h only in the cells treated with SGT-53 (FIG. 1A). Following SGT-53 treatment, increased expression of type I interferon (IFNalpha1) and several cytokines related to innate immunity (CCL2, CXCL1 and IL15) were evident at 48 and 72 h after treatment (FIG. 1B). Increased expression of DEC1, indicative of cellular senescence was also observed (FIG. 1B). Notably, we observed a significant increase in the level of programmed death-ligand 1 (PD-L1) mRNA in cultured 4T1 cells (a mouse model of metastatic breast cancer) after SGT-53 treatment (FIG. 1B). We have also observed increased release of high mobility group box 1 (HMGB 1) and ATP in the culture media following SGT-53 treatment (FIG. 1C), which supports induction of Immunogenic Cell Death (ICD). To assess whether introduction of human wtp53 altered 4T1 cell survival, we examined apoptotic activity using an Annexin V assay (FIG. 1D). Both Annex V+/7-AAD− (apoptotic) and Annex V+/7-AAD+(dead) cells were significantly increased after SGT-53 treatment compared to either untreated cells or those exposed to the control nanocomplex loaded with a plasmid encoding GFP (scL-GFP). FACS analysis of 4T1 cells revealed significantly increased surface expression of calreticulin (CRT), Fas cell surface death receptor (FAS), and PD-L1 following SGT-53 treatment while scL-GFP did not increase the surface expression of any these markers (FIG. 1E). Surface expression of the endoplasmic reticulum (ER) protein CRT is an indicative of ICD as are release of innate immune receptor ligands (HMGB 1 and ATP). Together, these data indicate that expression of functional p53 resulting from treatment with SGT-53 is responsible for both induction of ICD and alterations in the immunogenicity of 4T1 cells in vitro and that these effects are not merely due to the introduction of a generic plasmid DNA.

Figure 2A:
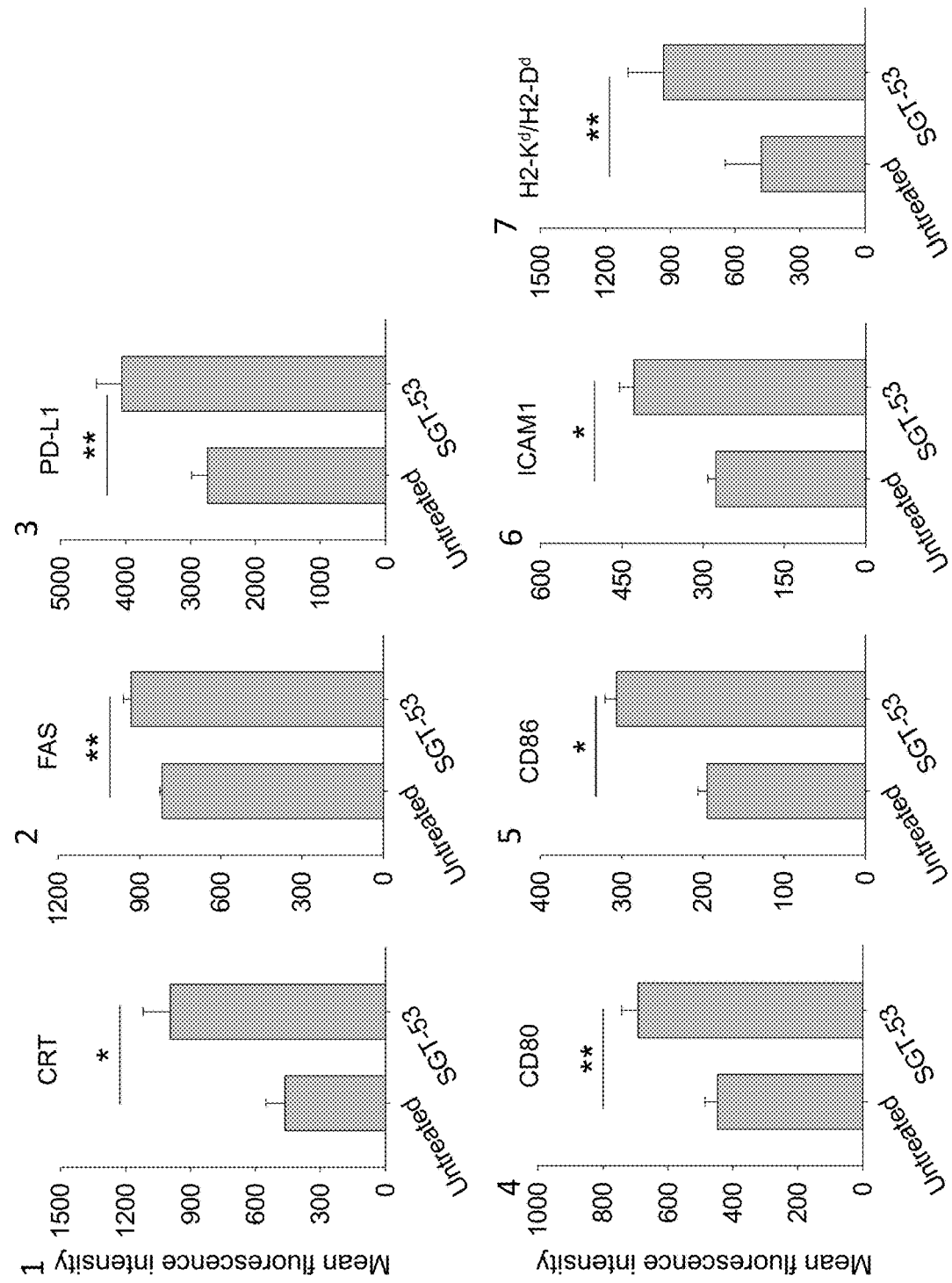
FIG. 2A (1-7). SGT-53 increases immunogenicity of tumor in vivo. Mice bearing established 4T1 tumor were i.v. treated with SGT-53 (30 µg DNA/mouse). Expression of cell surface components of immunogenicity was assayed 48 h later via FACS and compared with those in tumor from untreated mice (n=4). Tumor cells were dissociated by enzymatic digestion and identified by gating CD45-CD31-live cells. Data are shown as mean±SEM. *$p<0.001$, **$p<0.05$, Student's t test.
Figure 2B:
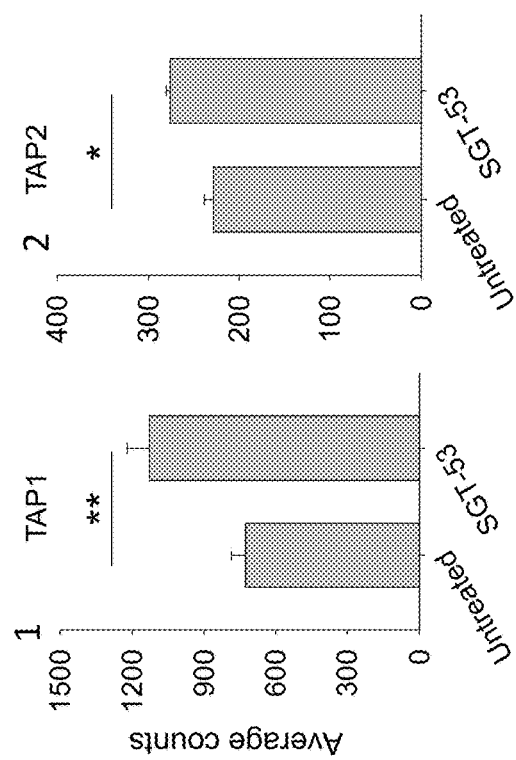
FIG. 2B (1-2): SGT-53 increases TAP1 and TAP2 expression in vivo. Mice bearing established 4T1 tumor were i.v. treated with SGT-53 (30 µg DNA/mouse). Expression of TAP1 and TAP2 was assayed 48 h later via NanoString and compared with those in tumor from untreated mice (n=4). Data are shown as mean±SEM. *$p<0.001$, Student's t test.

Following SGT-53 treatment, the altered immunogenicity of 4T1 tumor cells was further evaluated in vivo (FIG. 2A). Mice bearing subcutaneous (s.c.) syngeneic 4T1 tumors were treated with SGT-53 via tail vein injection, and the impact of SGT-53 treatment on a number of immune-relevant markers examined. Similar to our findings in vitro, FACS analysis of harvested tumors revealed significantly increased surface expression of immune cell recognition molecules including CRT, FAS, PD-L1, CD80, CD86, ICAM1 and MHC class I (H2-Kd/H2-Dd) after SGT-53 treatment (FIG. 2A). Gene expression analysis of tumors using NanoString showed the increased mRNA levels of transporter associated with antigen processing 1 (TAP1) and TAP2 after SGT-53 treatment, which are implicated as important TP53 dependent components of antigen presenting machinery and mediators of ICD (FIG. 2B) (29, 30). Together with the in vitro results, these in vivo data show that p53 alters the expression of immunogenic markers on the surface of tumor cells and induces ICD of tumor cells. In short, the tumors treated with SGT-53 appear to be more immunologically "hot", and this change would be expected to result in an increased immune response to tumor cells expressing the exogenous p53 encoded by the DNA payload of SGT-53.

Example 3

Figure 3A:
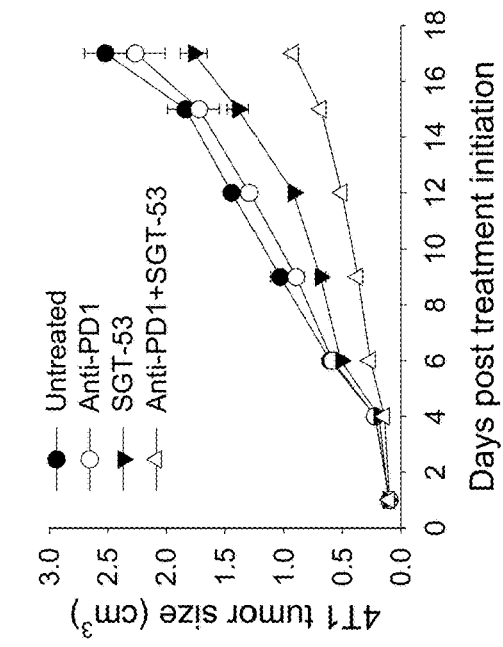
FIGS. 3A-3D: Enhanced tumor growth inhibition by the combination of anti-PD1 and SGT-53. BALB/c mice with s.c. 4T1 tumor were randomized to therapy with anti-PD 1, either alone or in combination with SGT-53 (n=10). (A) Treatment schedule. Mice received total 5 injections of SGT-53 and/or 5 injections of anti-PD1. (B) Changes in tumor sizes were plotted versus the number of days after initiation of the treatment. (C) Quantification of tumor weight at harvest on day 17. For group treated with anti-PD1, tumors were harvested on day 16 or 17 when the mice were moribund. *$p<0.05$, **$p<0.001$, 1-way ANOVA with Bonferroni t-test. (D) Changes in body weight are shown. Data are shown as mean±SEM.

The Combination of an Anti-PD1 Antibody and SGT-53 is More Effective than Either Agent Individually in Inhibiting Tumor Growth and Metastasis Given the above data demonstrating the increased immunogenicity triggered by SGT-53, mice bearing s.c. established 4T1 tumors were treated with an anti-PD1 antibody alone or in combination with SGT-53 using the treatment schedule shown in FIG. 3A.

For the syngeneic 4T1 breast tumor model, 5-6 week old female BALB/c mice (Envigo) were s.c. inoculated with 4T1 cells in serum free media (SFM) ($0.5 \times 10^6$ cells/site). For the syngeneic LL2 lung cancer or GL261 glioblastoma models, 5-6 week old female C57BL/6 mice (Envigo) were s.c. inoculated with either LL2 cells ($0.5 \times 10^6$ cells/site) or GL261 cells ($1.0 \times 10^6$ cells/site), respectively. Mice were systemically injected with either SGT-53 [1 to 100 ug DNA/injection/mouse, intravenous (i.v.), preferably 5 to 60, more preferably 10 to 40, e.g. 30 ug], anti-PD1 antibodies [1 to 500 µg/injection/mouse, intraperitoneal (i.p.), e.g. preferably 10 to 400, more preferably 20 to 300 e.g. 200 ug, RMP1-14, BioXCell] or the combination of both, following the indicated treatment schedule in FIG. 3A.

Figure 3B:
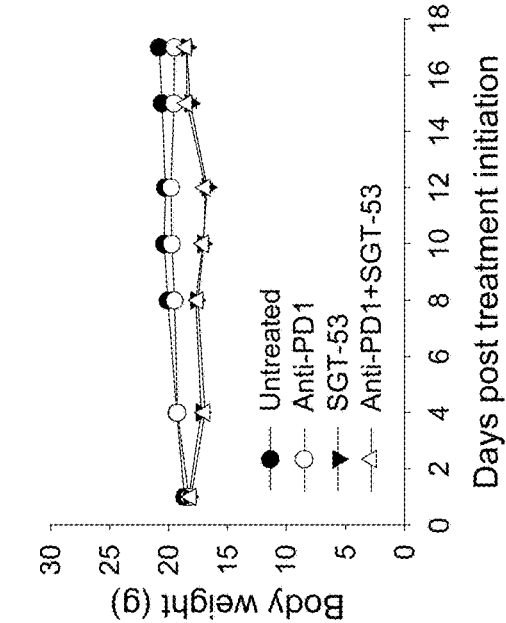
Figure 3C:
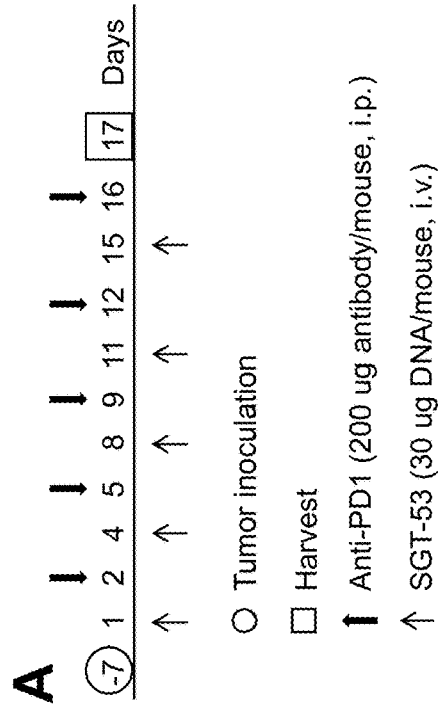
Figure 3D:
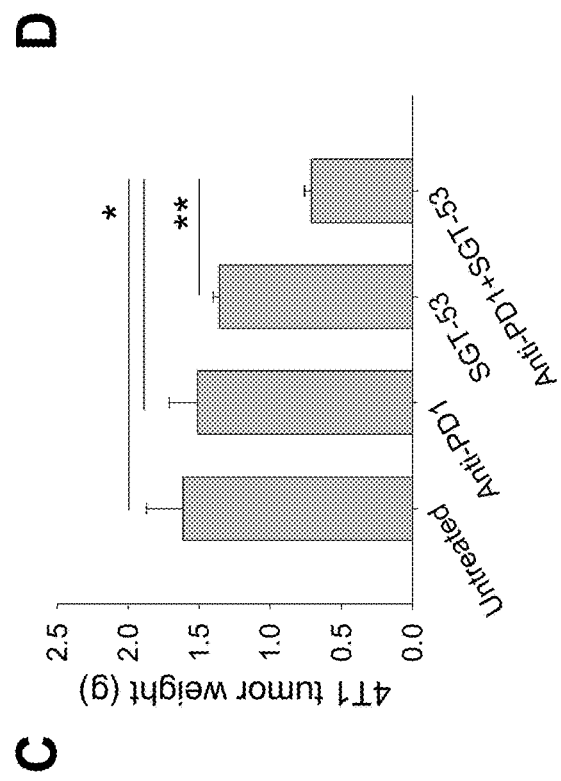

Anti-PD 1 (called a "checkpoint inhibitor") is an antibody directed against the inhibitory checkpoint molecule PD 1. No significant inhibition of tumor growth was seen with anti-PD 1 monotherapy indicating that the 4T1 tumors display inherent therapeutic resistance to anti-PD 1 checkpoint blockade (FIG. 3B). SGT-53 treatment alone resulted in some inhibition of 4T1 tumor growth. However, the combination of anti-PD 1 plus SGT-53 treatment resulted in a significantly diminished tumor growth leading to markedly smaller tumors compared to those in mice given either agent individually (FIGS. 3B&C). No significant decrease in body weight, accompanied the tumor growth inhibition seen with the combination treatment (FIG. 3D).

The observation of enhanced anti-tumor effect of anti-PD1 plus SGT-53 combination treatment was not limited to the 4T1 breast cancer model. Using the same treatment regimen, we have also seen improved anti-tumor efficacy in other mouse syngeneic tumor models including LL2 non-small cell lung carcinoma (FIG. 4A) and GL261 glioblastoma (FIG. 4B). In both tumor models, neither anti-PD 1 antibody nor SGT-53 treatment individually altered tumor growth dramatically. In contrast, similar to the effect seen with 4T1 tumors, the combination of anti-PD 1 and SGT-53 significantly delayed tumor growth of both LL2 and GL261. Moreover, the combination of anti-PD1 and SGT-53 clearly showed a strong, statistically significant survival benefit in both tumor models compared to both of the single agent treatments (FIG. 4C-4D). Thus, all three tumor models examined here were relatively unresponsive to anti-PD 1 treatment, but SGT-53 sensitized each to an anti-PD1 antibody. We have also previously observed a similar enhancement of anti-tumor activity in mouse syngeneic model of head and neck cancer (31). Collectively, our results demonstrate that SGT-53 treatment has the potential to convert tumors resistant to anti-PD 1 therapy to more responsive tumors. Extrapolating to human cancers, this conversion to sensitivity has the will bring patients that do not respond to anti-PD 1 therapy into the category of responders and thereby enable checkpoint blockade agents to benefit a larger percentage of the total patient population.

Our observation of enhanced inhibition of 4T1 tumor growth by the combination of SGT-53 and anti-PD 1 treatment was supported by IHC staining. Mice were euthanized after completing treatment (day 17) or when the control animals developed excessive tumor burden. Harvested tumor, lung, and liver were fixed in 10% neutral buffered formalin, paraffin embedded, and sectioned at 5 µm. Tumor sections were stained for Casp3 (Cell Signaling Technology, 9661) or Ki-67 (Dako, M7240) antibodies according to manufacturer's instructions. TUNEL staining was performed using the ApopTag peroxidase in situ apoptosis detection kit (Millipore, S7100) according to manufacturer's instructions. H&E (Surgipath, Leica Biosystems) staining was performed on lung and liver sections. Images were captured using Olympus DP70 camera on Olympus BX61 microscope. The percentages of Casp3, TUNEL, or Ki-67 positive cells were counted using the ImmunoRatio, an automated cell counting software (http://153.1.200.58:8080/immunoratio/) at least five fields of view from three tumor sections.

Figures 5A, 5B:
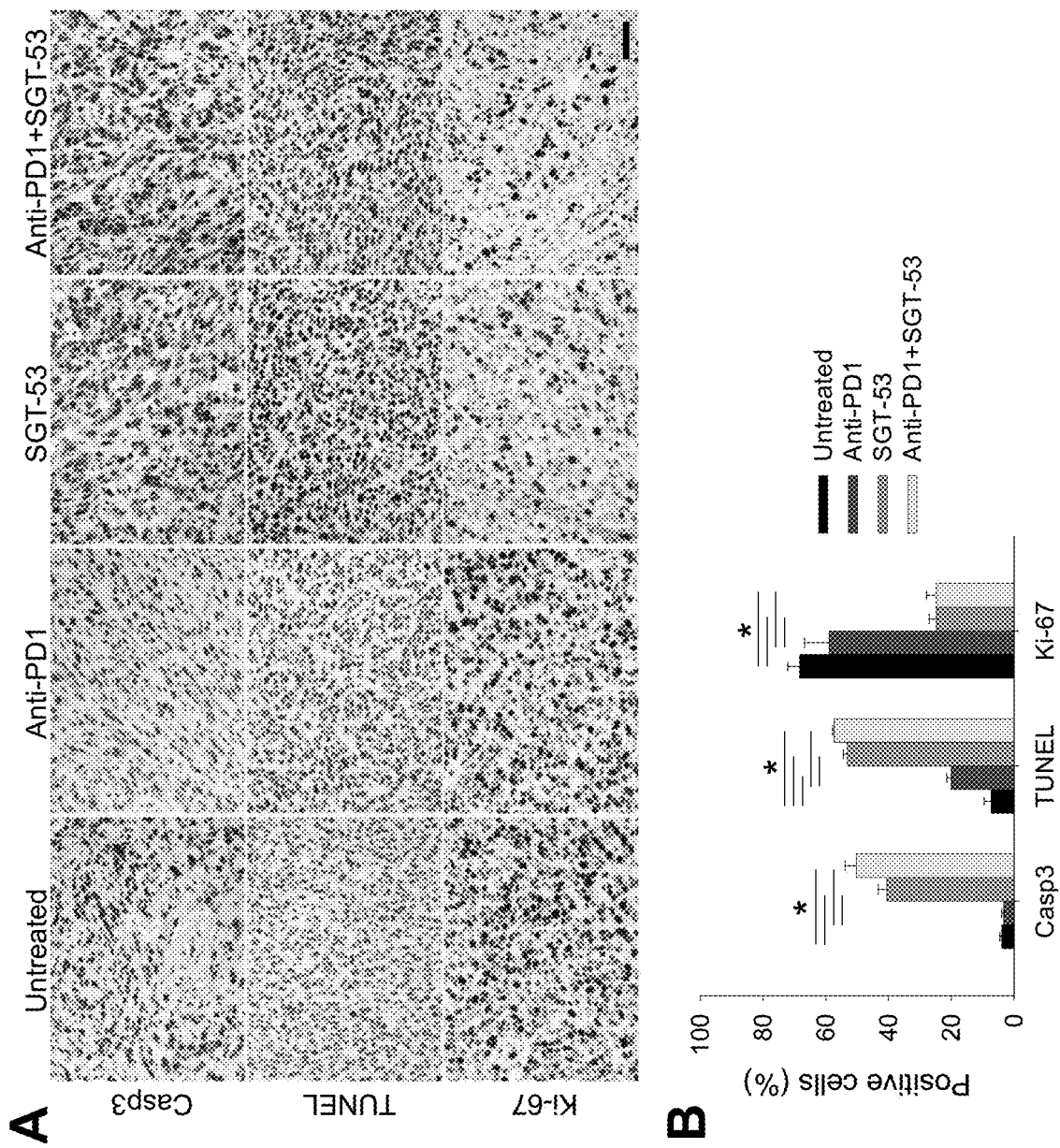
FIGS. 5A-5B: SGT-53 increases apoptosis and inhibits proliferation of 4T1 tumor in vivo. IHC staining of tumors treated as shown in FIG. 3A. Representative IHC staining (A) and quantification (B) of Casp3, TUNEL, and Ki-67 are shown. Scale bar, 50 μm. At least five fields of view from three tumor sections were counted using the ImmunoRatio, an automated cell counting software (http://153.1.200.58:8080/immunoratio/). Data are shown as mean±SEM. $*p<0.05$, 1-way ANOVA with Bonferroni t-test.

The IHC showed increased active caspase-3 (Casp3) and TUNEL indicative of tumor cell apoptosis as well as by decreased Ki-67 expression reflecting reduced tumor cell proliferation (FIG. 5A). Tumors in mice treated with SGT-53 alone or in combination with the anti-PD1 antibody treatment exhibited significantly higher levels of Casp3-positive and TUNEL-positive cells when compared to tumors in untreated mice or those treated with anti-PD1 alone (FIG. 5B). Combining anti-PD1 and SGT-53 showed only a modest increase of apoptotic cells compared to SGT-53 treatment alone consistent with the known role of p53 as a driver of apoptosis. Tumors in mice treated with SGT-53 alone or in combination with the anti-PD 1 antibody exhibited a significantly lower level of Ki-67-positive cells compared to tumors in mice either untreated or treated with anti-PD 1 monotherapy. Our data indicate that Ki-67 levels were not affected by anti-PD1 as a single agent, nor did anti-PD1 accentuate the inhibition of Ki-67 expression seen in mice treated with SGT-53 alone.

Example 4

SGT-53 Dramatically Reduces Metastases of 4T1 Tumor in the Lungs

Figures 6A, 6B:
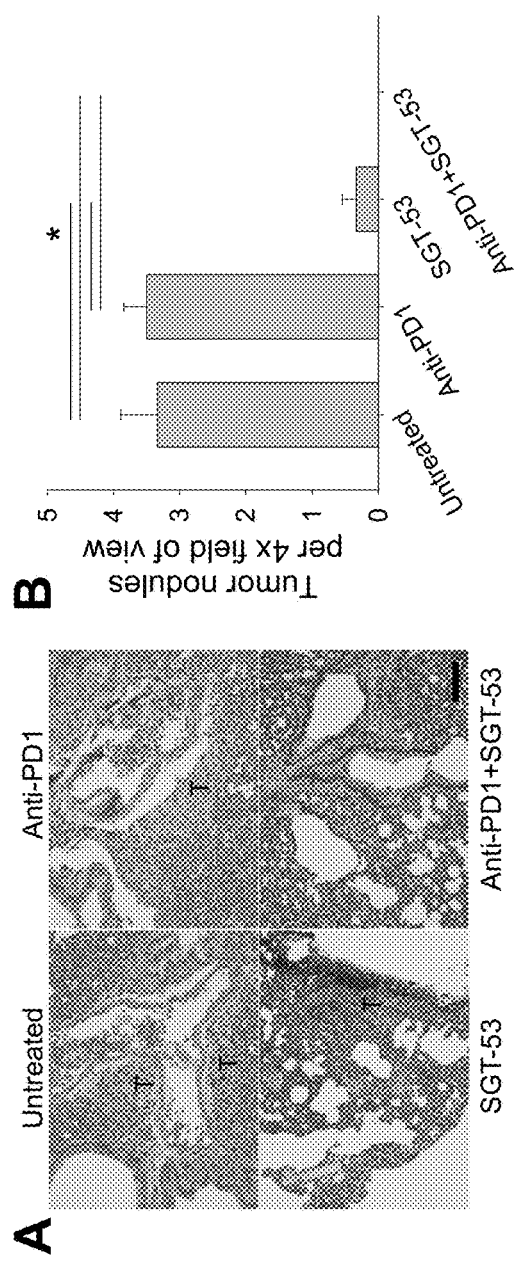
FIGS. 6A-6B: SGT-53 substantially reduces lung metastases of 4T1 tumors. Lung tissues were harvested from tumor-bearing BALB/c mice treated as shown in FIG. 3A. (A) Representative images of H&E stain of lung. T, tumor. Scale bar, 100 μm. (B) Metastatic lung nodules were microscopically counted per 4× field of view and plotted. At least five fields of view from three tissue sections were counted and averaged. Data are shown as mean±SEM. $*p<0.001$, 1-way ANOVA with Bonferroni t-test.

Mice bearing the 4T1 subcutaneous breast tumors, induced as described in Example 3, experience metastases to the lungs resembling some breast cancer patients in this regard. Indeed, 4T1 is considered to be a mouse model for metastatic breast cancer. It is possible to quantify microscopically 4T1 metastatic nodules in sections of the lungs of the 4T1-bearing mice (FIG. 6A). Treatment of the mice with SGT-53 alone was able to reduce substantially metastases of 4T1 tumor in the lungs whereas treatment with anti-PD 1 alone was essentially ineffective (FIGS. 6A&B). In mice treated with the combination of SGT-53 plus anti-PD1 antibody, virtually no 4T1 lung nodules were detected. These results are consistent with our earlier findings showing improved anti-tumor activity with the combination treatment and suggests that the combination treatment may be able to reduce the lung metastases from breast cancers that contributes to breast cancer mortality.

Example 5

SGT-53 Enhances Immune Responses in 4T1 Tumor In Vivo

The findings described above in EXAMPLES 2-4 are consistent with enhancement of both innate and adaptive immunity. To extend these observations, FACS analyses of tumor infiltrating myeloid cells were conducted in 4T1 tumors, induced as described above, following SGT-53 treatment either as a single agent or in combination with an anti-PD1.

Tumors were harvested, weighed, and cells were dissociated by enzymatic digestion in Hank's balanced solution containing 1 mg/mL collagenase D (Roche, 1108888200) and 2 mM DNase I (Sigma, D4263) for 1 h at 37° C. Cells collected from these in vivo studies (or in vitro studies) were stained with antibodies against FAS (152606), PD-L1 (124308), CD80 (104716), CD86 (105037), ICAM1 (116120), H-2Kd/H-2Dd (114708), I-A/I-E (107632), CD45 (103146), CD31 (102424), CD3 (100218), CD4 (100449), CD8a (100708), CD11c (117310), F4/80 (123110), CD107a (121608), Gr1 (108452), FoxP3 (126419), GzmB (515406), IFNgamma (505839, all from BioLegend), CD11b (BD Biosciences, 552850), and CRT (Novus Biologicals, NBP1-47518APC). For the cells isolated from the tumor tissue, they were labelled with Zombie-NIR viability dye (BioLegend, 423105) prior to the staining with antibodies according to the manufacturer's instructions. To assess the level of apoptosis, cells were stained with Annexin V apoptosis detection kit with 7-AAD (BioLegend, 640926). Cells were analyzed by LSRFortessa flow cytometer (BD Biosciences).

Figures 7A, 7B:
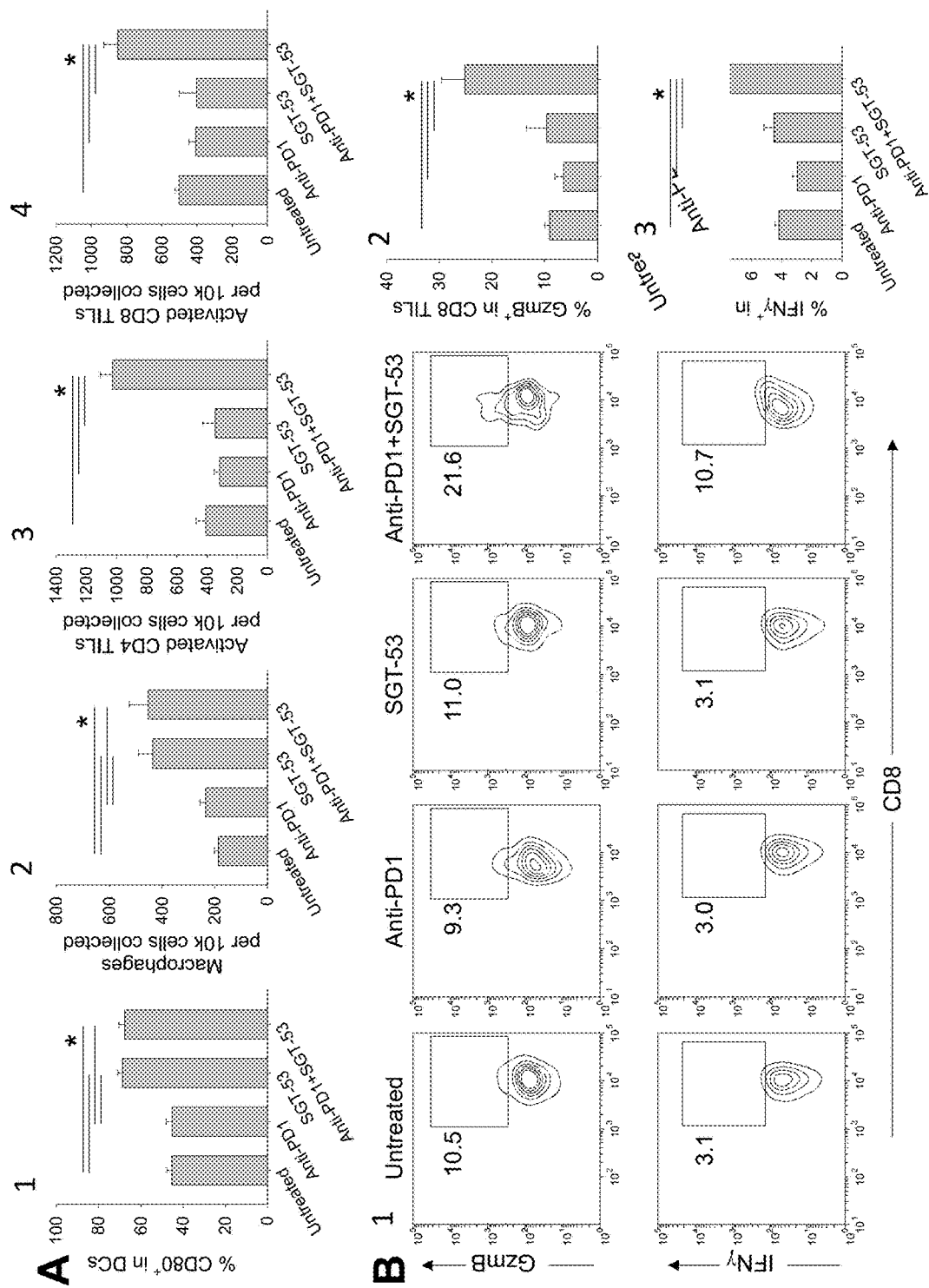
FIGS. 7A-7E SGT-53 enhances immune responses in 4T1 tumor in vivo. Tumor cells were dissociated and immune cell infiltration was assessed via FACS. (A) (1-4) Infiltrating immune cells were identified by gating CD45+ live cells including DCs (CD11c+I-A/I-E+), macrophages (CD11b+F4/80+), activated CD4 TILs (CD3+CD4+CD107a+), and activated CD8 TILs (CD3+CD8+CD107a+). Infiltrating cells are shown in terms of absolute number of cells per 1×104 live cells collected (n=6-8). (B) (1-3) Representative FACS plots (left panels) and graphs (right panels) of CTLs (CD3+CD8+GzmB+ or CD3+CD8+IFNγ+) are shown. Numbers in the plots indicate the percentage of cells (n=6-8). (C) (1-2) Immunosuppressive MDSCs (CD11b+Gr1+) and Tregs (CD3+CD4+FoxP3+) were identified (n=6-8). (D) Altered expression of genes associated with immunosuppression in the tumor tissue were assessed via NanoString. (E) (1-4) Expression of genes associated with immunosuppressive enzymes was assessed by RT-PCR in the tumors (n=6-8). The fold-change relative to untreated tumors is shown. Data are shown as mean±SEM. $*p<0.05$, 1-way ANOVA with Bonferroni t-test.
Figures 7C, 7D, 7E:
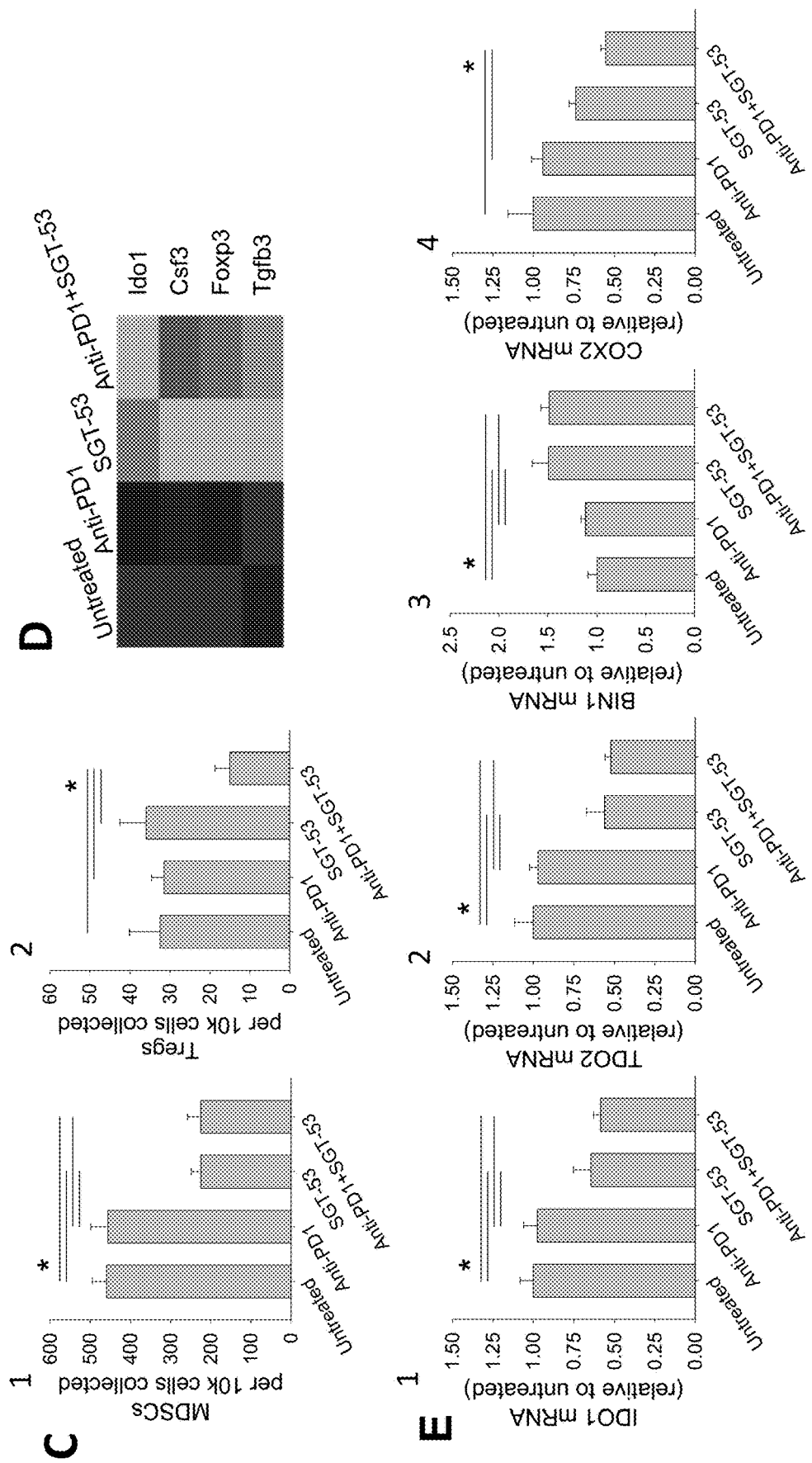

The FACS analysis from the 4T1 tumors revealed an increase of CD80+ activated dendritic cells (DCs) and tumor infiltrating macrophages following SGT-53 treatment either as a single agent or in combination with an anti-PD 1 (FIG. 7A). Treatment with anti-PD 1 alone did not affect the number of tumor infiltrating macrophages or DCs. When SGT-53 was combined with anti-PD 1 antibody, the number of activated tumor-infiltrating lymphocytes (TILs) was substantially increased. However, neither anti-PD 1 antibody nor SGT-53 alone led to significant increase of activated TILs. We also observed a significant increase in granzyme B (GzmB)-positive or IFN gamma (IFNγ)-positive cytotoxic T cells (CTLs) in tumors following treatment with anti-PD 1 plus SGT-53, whereas no significant increase of CTLs were observed with anti-PD1 or SGT-53 individually (FIG. 7B). Tumor infiltrating immunosuppressive cells including myeloid derived suppressor cells (MDSCs) and regulatory T cells (Tregs) were significantly altered by SGT-53 treatment (FIG. 7C). Tumors treated with SGT-53 alone or in combination with anti-PD1 showed significantly less MDSCs compared with tumors in untreated mice or those treated with anti-PD1 alone. A significant reduction of Tregs was observed when mice were treated with anti-PD 1 plus SGT-53.

Gene expression in the tumors was analyzed using NanoString (NanoString Technologies) using two commercially available gene panels (mouse PanCancer Pathways and mouse PanCancer Immune profiler) containing a total of 1330 unique genes. Fifty-eight (58) RNAs was isolated as described above from 4T1 tumor tissues and hybridized with probes according to the manufacture's protocols. The resulting RNA complexes were subsequently immobilized and counted on an nCounter® analyzer (NanoString Technologies). Raw data were normalized based on the geometric mean of negative controls, internal housekeeping genes, and positive controls in nSolver 3.0 software (NanoString Technologies). Normalized counts from genes included in both panels were analyzed further using nSolver 3.0.

The NanoString analysis revealed a significant down-modulation of genes associated with immunosuppression including indoleamine 2,3-dioxygenase 1 (IDO1) and FoxP3 following SGT-53 treatment (FIG. 7D). Quantitative RT-PCR analysis was also performed on the tumor samples. Total RNAs were extracted from tumor tissues using Pure-Link RNA Mini Kit (Ambion, 12183018A) according to the manufacturer's protocol. One microgram of extracted RNA was reverse transcribed in 20 μL reaction volume with Superscript IV VILO Master Mix (Life Technologies, 11766050) with ezDNase enzyme, which removes genomic DNA, following the manufacturer's protocol. PCR was performed using TaqMan Fast Advanced Master Mix (Life Technologies, 4444557) and TaqMan gene expression assays (Life Technologies) for human p53 (Hs01034249_ml), mouse IFNalpha1 (Mm03030145_gH), mouse CCL2 (Mm00441242_m1), mouse CXCL1 (Mm04207460_ml), mouse IL15 (Mm00434210_m1), mouse DEC1 (Mm00478593_ml), mouse PD-L1 (Mm00452054_ml), and mouse GAPDH (Mm99999915_g1) with StepOnePlus RT-PCR system (Life Technologies). Relative mRNA expression was analyzed using StepOne Software v2.3 via the ΔΔCt method with normalization to GAPDH mRNA. Samples were assayed in triplicate.

The results of the RT-PCR analysis of the tumors further confirmed the down-modulation of immunosuppressive enzymes both IDO1 and tryptophan 2,3-dioxygenase 2 (TDO2) by SGT-53 treatment via modulating bridging integrator 1 (BIN1, negative regulator) and cytochrome c oxidase 2 (COX2, positive regulator) (FIG. 7E). These data all demonstrate that p53 expression from SGT-53 alters the tumor microenvironment (TME) in such a way to reduce tumor evasion and to enhance anti-tumor immunity and adaptive immune response in combination with anti-PD1 treatment. Tumors appear to be more immunologically "hot" in mice treated with the combination of the two agents, i.e., these tumors are more prone to trigger responses by both the innate and adaptive immune systems. The primary mechanism of the anti-PD1 checkpoint inhibitors is thought to be release of the PD1-mediated immunosuppression of T cells, it is perhaps not surprising that the anti-PD 1 as a single agent did not have an impact on the level of tumor infiltration by cells of the innate immune system i.e., DCs and macrophages (FIG. 7A, left two panels). The effect of the anti-PD1 antibody was apparent in combination with SGT-53 in the T-cell-related results (FIG. 7A, right two panels). Collectively, these results indicate that the role of SGT-53 is to prime the TME and that the resultant "hot" tumors are more sensitive to the release from PD1-mediated immunosuppression of T cells by the anti-PD1 component of the combination treatment.

Example 6

Figure 8A:
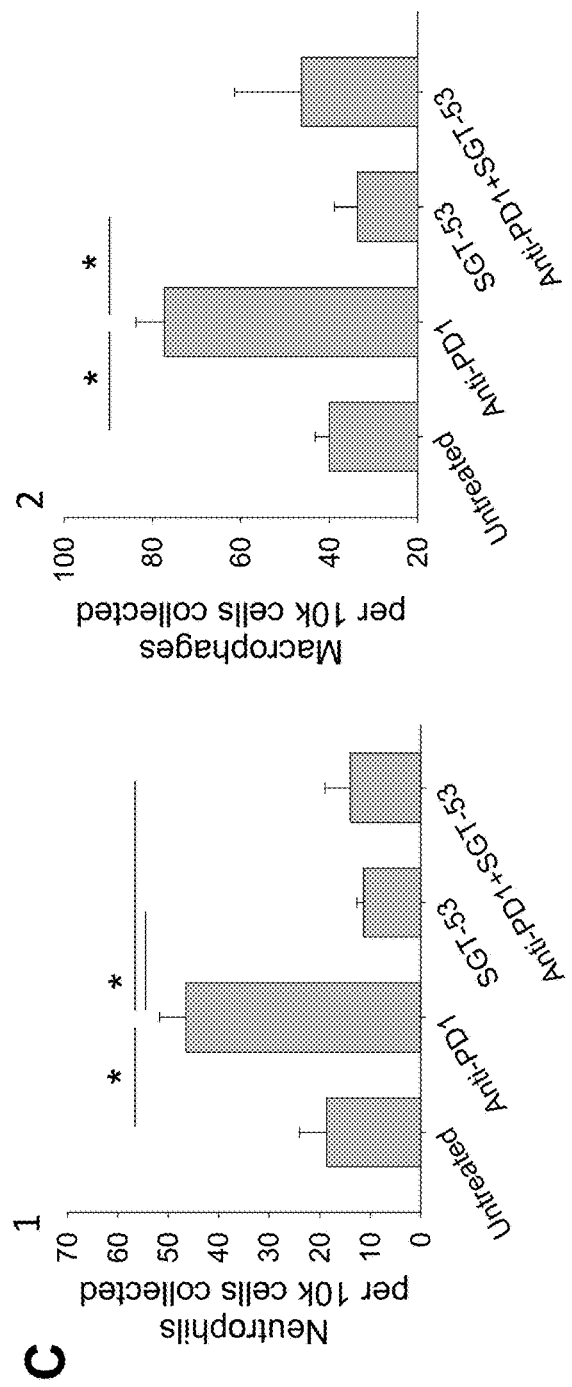
FIGS. 8A-8E SGT-53 prevents fatal xenogeneic hypersensitivity following repeated anti-PD1 administration in a syngeneic 4T1 breast cancer model. (A) Survival of BALB/c mice bearing 4T1 tumor after repeated dosing with anti-PD1 antibody alone or in combination with SGT-53. Mice received total five injections of SGT-53 and/or five injections of anti-PD 1 following the treatment schedule shown in FIG. 3A. Arrows indicate the anti-PD1 injection. (B) Representative H&E stains of lungs and livers of mice treated with either anti-PD 1 alone or in combination with SGT-53. Arrowheads indicate neutrophilic accumulation. Scale bars, 200 μm. (C) (1-2) Infiltrating neutrophils (CD11b+F4/80-Gr1hi) and macrophages (CD11b+F4/80+) were assayed in the lung via FACS (n=4). Infiltrating cells are shown in absolute number of cells per 1×104 live cells collected. (D) Heatmap of significantly altered gene expression in tumor tissue from mice treated with anti-PD 1 antibody that were reversed in tumor tissue from mice treated with anti-PD 1 plus SGT-53. (E) (1-2) Sera from tumor bearing mice receiving the indicated treatment were collected and analyzed for levels of mouse GM-CSF or TNFα using ELISA (n=8). Data are shown as mean±SEM. $*p<0.05$, $**p<0.001$, 1-way ANOVA with Bonferroni t-test.
Figure 8B:
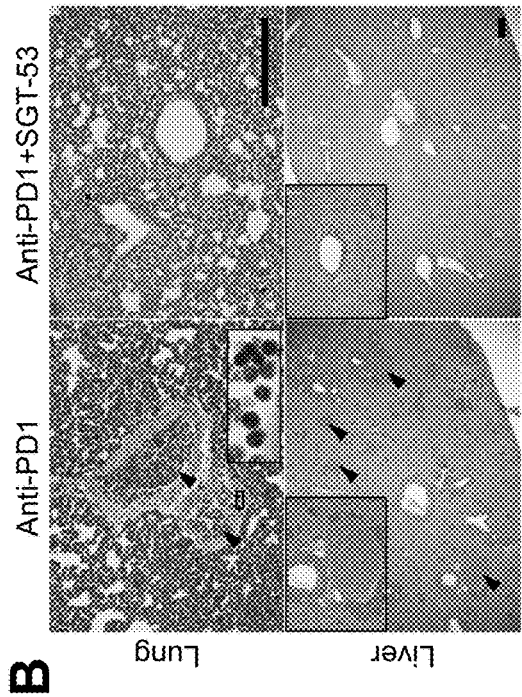
Figure 8C:
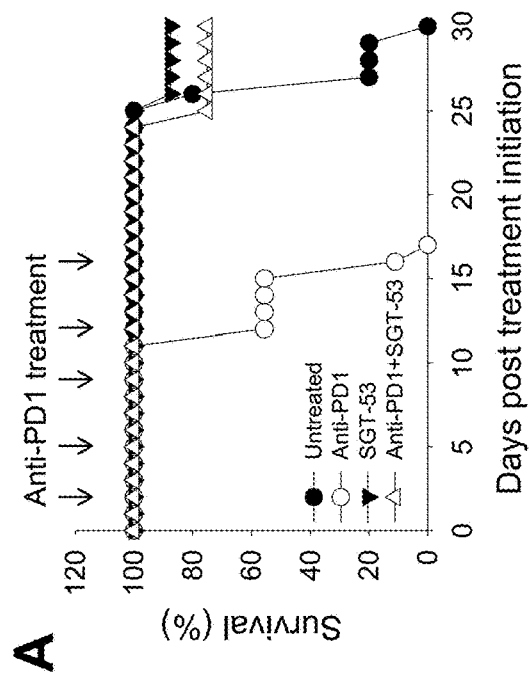

SGT-53 Prevents Fatal Xenogeneic Hypersensitivity Following Repeated Anti-PD1 Administration in a Syngeneic 4T1 Breast Cancer Model We observed that BALB/c mice bearing 4T1 tumors died after multiple injections of anti-PD 1 antibody (clone RMP1-14; rat IgG). This death of the mice occurred within one hour after either the fourth or fifth injection, prior to their tumors having grown large enough to kill the animals (FIG. 8A). However, non-tumor bearing BALB/c mice survived the same treatment regimen and C57BL/6 mice bearing LL2 or GL261 tumors were not killed by the same anti-PD1 antibody. Others have also observed this fatal hypersensitivity after repeated injections of anti-PD 1 (clone J43; hamster IgG) or anti-PD-L1 (clone 10F.9G2; rat IgG) in the syngeneic 4T1 tumor model and suggested that mortality was associated with neutrophil-mediated anaphylaxis involving accumulation of neutrophils in the lungs (32). Unexpectedly and surprisingly, this fatal hypersensitivity seen with anti-PD1 antibody was not observed in the same 4T1 model when the PD1 blockade was combined with SGT-53 (FIG. 8A). Necropsy of mice that had received five injections with anti-PD 1 revealed massive infiltration of neutrophils and macrophages in the lung and liver (FIG. 8B), and FACS analysis confirmed abnormalities reflecting neutrophil and macrophage infiltration in the lung (FIG. 8C). The lung infiltration by neutrophils seen after treatment with anti-PD 1 antibody alone was eliminated if SGT-53 was given in conjunction with anti-PD 1. It is well known in the field that multiple injections of anti-PD 1 antibody triggered neutrophil-mediated anaphylaxis that kills the 4T1-bearing mice. Unexpectedly concurrent treatment with SGT-53 prevented both the neutrophil invasion of the lungs and livers and the death of the mice that were otherwise killed by anti-PD 1 antibody treatment. Although rare and generally of low severity, hepatitis due to immunotherapy with anti-PD 1 also has been reported (33).

Figure 8D:
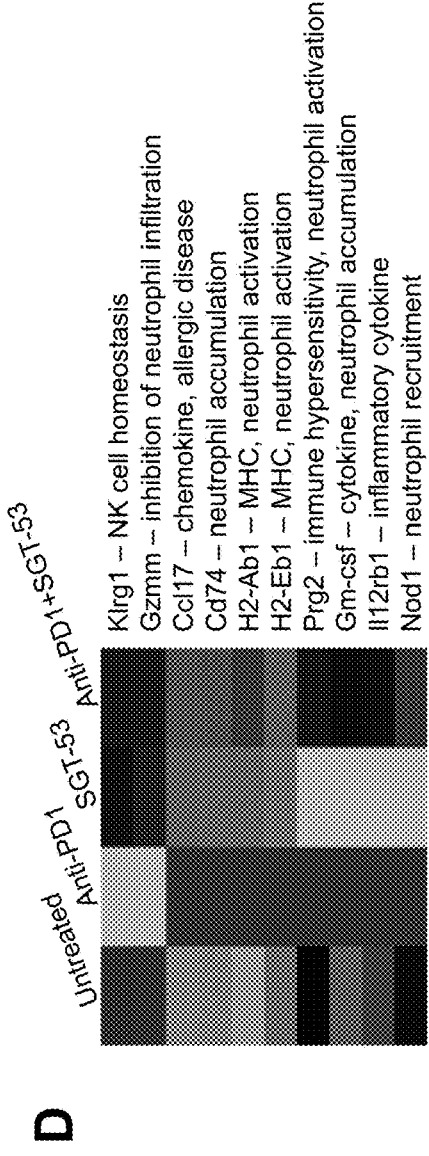
Figure 8E:
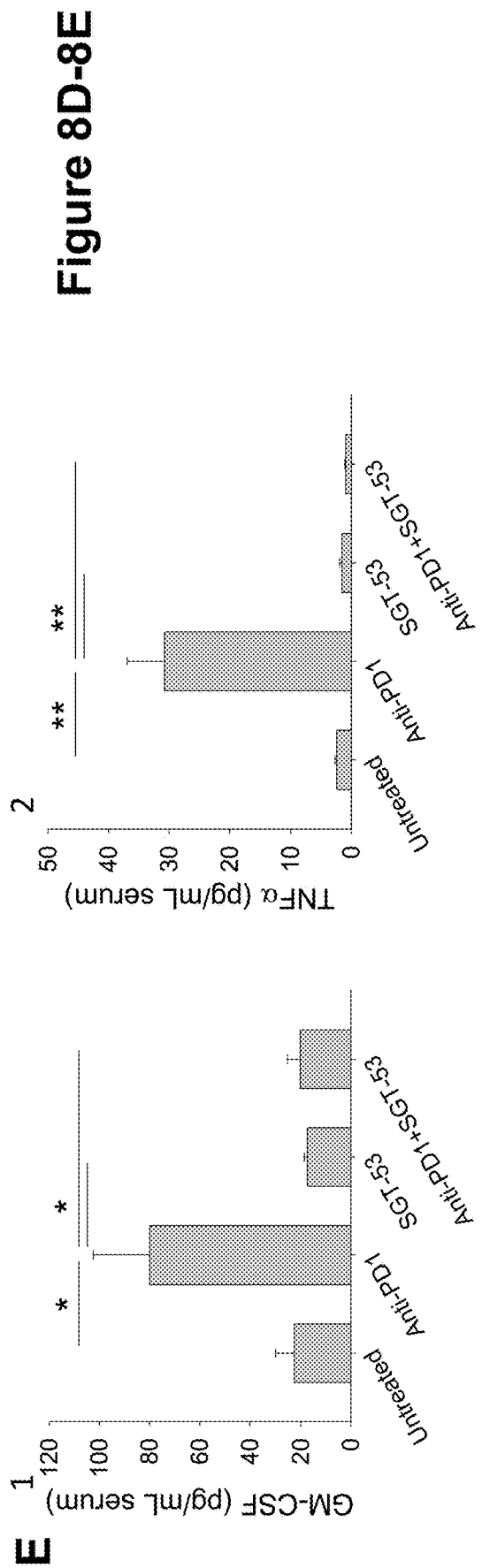

To understand the molecular basis of these observations, we performed gene expression profiling of tumor tissues from the mice. For these analyses, we employed the NanoString technique and specifically looked for candidate genes that were modulated by anti-PD 1 treatment alone but not when SGT-53 was added to anti-PD1 (FIG. 8D). The logic here was that some change(s) in gene expression would be linked to the anaphylactic death of 4T1-bearing mice, and that if SGT-53 prevents this death, then SGT-53 might prevent the underlying alteration in gene expression. Multiple genes involved in immune hypersensitivity and neutrophil recruitment, priming, and activation (Ccl17, Cd74, Prg2, Nod1, and GM-CSF) were identified as being upregulated by anti-PD1 monotherapy, while genes involved in inhibiting excessive neutrophil infiltration (e.g., Gzmm) were downregulated. The changes in expression of this set of genes were not observed with the combination treatment with anti-PD1 plus SGT-53. GM-CSF has been directly linked to lung-damaging neutrophil accumulation (34). GM-CSF mRNA was up-regulated with anti-PD1 treatment, but unexpectedly, when SGT-53 was added to the checkpoint blockade, GM-CSF expression in tumors was similar to that seen in the tumors of untreated animals. A similar unexpected result was observed with serum concentration of GM-CSF as assessed by ELISA (FIG. 8E). Serum GM-CSF was significantly increased (~4-fold) in 4T1 tumor-bearing mice receiving anti-PD1 treatment alone, but when SGT-53 treatment was added, GM-CSF levels in the sera were similar to that seen in untreated animals. Anti-PD 1 treatment also increased the serum level of the pro-inflammatory cytokine TNFalpha, in this case by ~12.8-fold (FIG. 8E). TNFalpha is known to be related to the cytokine-release syndrome seen after infusion of certain monoclonal antibodies (35). Once again, we had the unexpected result that SGT-53 treatment added to anti-PD 1 treatment resulted in TNFalpha levels equivalent to those seen in untreated animals. We have thus identified a set of genes that are candidates in the fatal xenogeneic hypersensitivity reaction that we see in 4T1-bearing mice. It was unexpected and surprising that SGT-53 treatment prevented the modulation of the expression of these genes by anti-PD 1 monotherapy and "rescues" the mice from the otherwise fatal treatment with this checkpoint inhibitor. Taken together with above efficacy data, these results demonstrate that SGT-53 renders checkpoint blockade not only more effective but also safer.

DISCUSSION

It has long been appreciated that the restoration of p53 function via gene therapy has potential to combat cancer (18). While the killing of cancer cells by p53 does not require a fully functional immune system, p53 can push cancer cells toward apoptotic death and tends to sensitize tumors to conventional therapeutic modalities (chemotherapy and radiotherapy) that result in DNA damage (36). Indeed, we have shown that the restoration of p53 function via SGT-53, a tumor-targeted nanomedicine, could inhibit tumor growth and sensitize xenografts of human tumors in nude mice lacking T cells to both chemotherapy (37, 38) and radiotherapy (39). Nonetheless, it has become clear that p53 also participates in various aspects of immune modulation in cancer (40). In the present study, we are reporting that introducing functional wtp53 gene via SGT-53 can induce immunogenic changes of cancer cells, effectively promote anti-tumor immunity, and reduce tumor-induced immunosuppression in the TME. By augmenting anti-PD 1 immune checkpoint blockade, the SGT-53 was able to convert mouse syngeneic tumors that were relatively insensitive to anti-PD 1 into tumors that were more responsive to anti-PD 1 therapy. This priming or sensitization of tumors to anti-PD 1 resulted in a significant inhibition of tumor growth. In support of our observation is a recent report suggested that the tumoricidal effects of p53 following nutlin-3a treatment (which inhibits the interaction between p53 and mdm2 that blunts p53 activity) promoted systemic anti-tumor immunity (41). The induction of immunogenic conditions in the TME with an immunogenic chemotherapy or radiation therapy is thought to convert immunologically "cold" tumors into "hot" tumors via release of tumor neoantigens (42, 43). Similarly, the pushing of tumor cells toward immunogenic death by SGT-53 may be quite effective in promoting in tumor elimination by the immune system.

The involvement of p53 in immune regulation appears to be multifaceted in that SGT-53 treatment modified immunogenicity of tumor cells, increased both innate and adaptive immunity, and reduced tumor-induced immunosuppression in the TME. In cultured 4T1 mouse breast cancer cells, we observed changes indicative of ICD after SGT-53 treatment including increased surface expression of the ER protein CRT and release of cell death associated molecular patterns (HMGB 1 and ATP) (44). Several additional alterations in immunogenicity were also observed with SGT-53 treatment including type I IFN responses and increased tumor expression of CD80, CD86, FAS, TAP1/2, and MHC I molecules in vivo. We have previously shown that SGT-53 treatment of MOC1 head and neck cancer cells could upregulate the expression of genes involved in antigen processing and presentation including CRT, calnexin, endoplasmic reticulum amino peptidase 1, and TAP1/2 involving stimulator of interferon genes (STING) pathway (45). The increased expression of MHC I molecules could also be linked to the increased type I IFN responses (46). Importantly, resistance to anti-PD 1 therapy could be mediated by suppression of type I IFN signaling in a preclinical model of Kras-mutated p53-deficient lung cancer (46). In this model, induction of IFNγ by radiotherapy was able to elevate MHC I expression and restore the responsiveness of resistant tumors to anti-PD 1 therapy. Increased FAS expression with SGT-53 treatment could also increase CTL-mediated apoptosis of tumor cells since CTLs use FAS/FAS ligand binding to induce apoptosis of target cells during the CTL-tumor cell interaction (47, 48). These observations recapitulate previous findings (30, 45, 49-51), and it is reasonable to believe that elevated expression of these component of immunogenicity would be instrumental in achieving efficient anti-tumor immune responses.

Moreover, we have observed increased production of cytokines (e.g., CCL2, CXCL1, and IL15) related to recruitment of innate immune cells after SGT-53 treatment of 4T1 cells. In line with this data, SGT-53 resulted in a significant increase of activated DCs and macrophage infiltration in TME in vivo. In addition, the increases in the number of activated TILs and GzmB-positive/IFNγ-positive CTLs in the tumor were associated with the increased anti-tumor efficacy in 4T1 tumor-bearing mice treated with the combination of SGT-53 plus anti-PD1. Supporting our data, there is increasing evidence indicating that p53 can regulate the cell-mediated adaptive immune response to tumors and ultimately promote CTL-induced cancer cell death (30, 48-50). Moreover, introduction of p53 into tumor cells was shown to enhance induction of apoptosis following exposure to CTL-mediated cytotoxic insults (50) and p53 accumulation in tumor cells is an indispensable component in the GzmB-induced apoptotic signaling pathway (52, 53).

The cytotoxicity of CD8 TILs against the tumor can be influenced by multiple immunosuppressive factors in the local TME, such as suppressive cytokines, suppressor cells (e.g., Tregs and MDSCs), and signaling through inhibitory immune ligands (54-56). Tregs and MDSCs are crucial populations in enforcing immunosuppression in the TME (41). Although further investigations on underlying mechanisms are needed, our study showed that elevated p53 expression resulting from SGT-53 treatment can be exploited as a new means of eliminating these immunosuppressive cells, accounting for the increase in activated TILs and anti-tumor immunity seen in vivo when SGT-53 is used in combination with checkpoint blockade. Importantly, gene expression profiling revealed the significant down-modulation of IDO1, an enzyme known for its key immunosuppressive role in many human cancers, following SGT-53 treatment. It has been previously shown that tryptophan depletion by cancer cell-expressed IDO1 could lead to the T cell anergy and activation of immunosuppressive Tregs and MDSCs (57, 58). Currently, drugs targeting IDO1 pathway are in clinical trials to reverse the tumor-induced immunosuppression (58). In accordance with our data, a recent report demonstrated that restoration of p53 activity via nutlin-3a was able to induce ICD and promote CD8 T cell-dependent anti-tumor immunity in mice bearing EL4 tumor (41). In that study, activated p53 was able to eliminate immunosuppressive MDSCs. However, reactivation of endogenous p53 via nutlin-3a requires tumor cells harboring wtp53 and many tumor cells would be expected to be unresponsive to nutlin-3a. In contrast, our tumor-targeted gene therapy approach to restore functional p53 and subsequently induce tumor cell immunogenicity and anti-tumor immunity would not be expected to be dependent on the p53 status of the tumor. Indeed, in human tumor cell lines, we have observed that SGT-53 can push cells harboring either WT or mutated p53 readily into apoptotic death (37, 38).

Despite clinical success of immunotherapy based on blockade of the PD1/PD-L1 axis, only a subset of patients exhibit durable responses (6). Moreover, therapeutic resistance can also develop. A recent study found that mutations that affected the antigen presentation and the sensitivity of tumor cells to T cell-derived IFNs could cause acquired resistance to anti-PD 1 therapy (5, 59). To overcome, or potentially prevent, the development of acquired immunotherapeutic resistance, a very large number of trials are now underway that combine checkpoint blockade with a wide range of other agents (14). In many cases, the combination under study appears to be lacking any strong mechanistic rationale for that particular combination. Although the elements involved in tumor response are complex (14), studies seeking biomarkers that might be used to predict response to anti-PD 1 antibody have found that tumor expression of PD-L1 is the single feature most highly correlated with response (60, 61). It has been suggested that cancer patients who do not respond to treatment with anti-PD 1 antibodies are those having tumors with relatively low expression of PD-L1 (3, 61-63). Our experiments revealed that SGT-53 treatment up-regulated PD-L1 expression in cultured 4T1 cells and in mouse syngeneic breast tumors in vivo. This PD-L1 up-regulation has also been observed in other mouse syngeneic tumor models (e.g., MOC1 head and neck cancer (45), GL261 glioblastoma and LL2 lung cancer, data not shown). Thus, it is our hypothesis that SGT-53 treatment will also elevate expression of PD-L1 on human tumors and expand the fraction of patients who respond to anti-PD1 antibodies. The ability of SGT-53 to elevate tumor PD-L1 in multiple syngeneic mouse models together with the fact that the treatment with SGT-53 plus the checkpoint inhibitor results in enhanced infiltration of the tumors by TILs provides a clear rationale for a trial involving this combination. This notion is supported by our observation in four syngeneic tumor models (4T1 breast cancer, LL2 lung cancer, and GL261 glioblastoma shown here plus MOC1 head and neck cancer (45)). These observations supports the contention that the combination of SGT-53 and anti-PD1 antibody could prove more efficacious as an immunotherapy regimen than the checkpoint blockade alone and thereby improve outcomes for cancer patients.

In addition to inhibiting tumor growth, SGT-53 plus anti-PD 1 reduced metastases. Mice bearing 4T1, a highly metastatic breast tumor, experience metastases to the lung akin to what is observed in some breast cancer patients. Strikingly, in the lungs of 4T1 tumor bearing mice, SGT-53 alone was able to reduce substantially metastatic tumor nodules, whereas anti-PD1 antibody treatment alone was essentially ineffective in blocking lung metastases. In mice treated with the anti-PD 1/SGT-53 combination, 4T1 lung nodules were essentially not detected. Although further studies are warranted, these data would support a combination clinical trial of an anti-PD1 antibody plus SGT-53.

Although PD1/PD-L1 checkpoint blockade is normally well-tolerated, three patients receiving nivolumab died from pneumonitis while participating in a trial (64). We observed that BALB/c mice bearing 4T1 tumors were killed when given 4-5 injections of anti-PD 1 antibody (clone RMP1-14; rat IgG). Deaths from the anti-PD 1 treatment of mice occurred prior to their tumors having grown large enough to be fatal. Hypersensitivity leading to death after repeated injections of xenogeneic anti-PD1 (clone J43; hamster IgG) or anti-PD-L1 (clone 10F.9G2; rat IgG) has also been observed by others using the 4T1 tumor model in BALB/c mice (32). Increased accumulation of neutrophils in the lung and the neutrophil-induced anaphylaxis were identified as the cause of death (32). We saw an abnormal lung infiltration of neutrophils only with anti-PD 1 antibody monotherapy but not with either SGT-53 alone or with the combination of anti-PD 1 and SGT-53 treatment. Likewise, mortality of mice seen after treatment with anti-PD1 antibody alone was prevented when SGT-53 was given in conjunction with the checkpoint inhibitor. Gene expression profiling of 4T1 tumors using the NanoString nCounter® analysis revealed a set of candidate genes linked to our observations. Many of these candidate genes are known to be involved in cellular immune responses including neutrophil priming and activation. The involvement of these candidate genes in the fatal xenogenic response warrants further study as does the mechanism by which death is averted by exposure to SGT-53. Nonetheless, our data suggest that SGT-53, when added to anti-PD 1 immunotherapy, may augment checkpoint blockade not only in terms of rendering checkpoint inhibitors more effective but also in making them safer for patients.

In summary, we describe that SGT-53 not only increased the immunogenicity of tumor cells and the number of tumor-infiltrating immune cells but also unexpectedly alleviated immunosuppression and improved anti-tumor activity when used in combination with an anti-PD1 antibody. This improved efficacy of the combination therapy was observed in three mouse syngeneic tumor models (4T1 breast cancer, LL2 non-small cell lung cancer and GL261 glioblastoma). A similar enhancement of anti-tumor activity was also observed in mouse syngeneic model of MOC1 head and neck cancer (45). Given that SGT-53 could alleviate fatal hypersensitivity associated with an anti-PD 1 antibody in 4T1 breast cancer, this nanomedicine may be able to reduce immune-related adverse events that are sometimes seen with cancer immunotherapies, an unexpected finding. Collectively, our data suggest that SGT-53, representing tumor-targeted p53 gene therapy, has potential to augment significantly immune checkpoint blockade agents for improved outcomes in a variety of malignancies. It is possible that the SGT-53 would not only improve outcomes in patients that already respond to checkpoint blockade, but also increase the percentage of patients who respond. SGT-53 has completed a first-in-man Phase I and Ib trials with favorable safety profiles (65, 66) and is now being evaluated in multiple Phase Ib and II trials as combination therapy with currently approved chemotherapeutic agents. Our data here provide a strong mechanistic rationale for combining SGT-53 and PD1/PD-L1-based immune checkpoint blockade in a clinical trial setting.

Example 7

SGT-53 Treatment Downregulates RAGE Expression in the Tumor and Impairs the Metastasis of Breast Cancer Cells in the Lung In tumor cells the p53 gene is downstream of RAGE and RAGE influences the activity of p53, not the reverse. However, we unexpectedly found that treating tumor cells with SGT-53 resulted in the down modulation of RAGE.

Figures 9A, 9B:
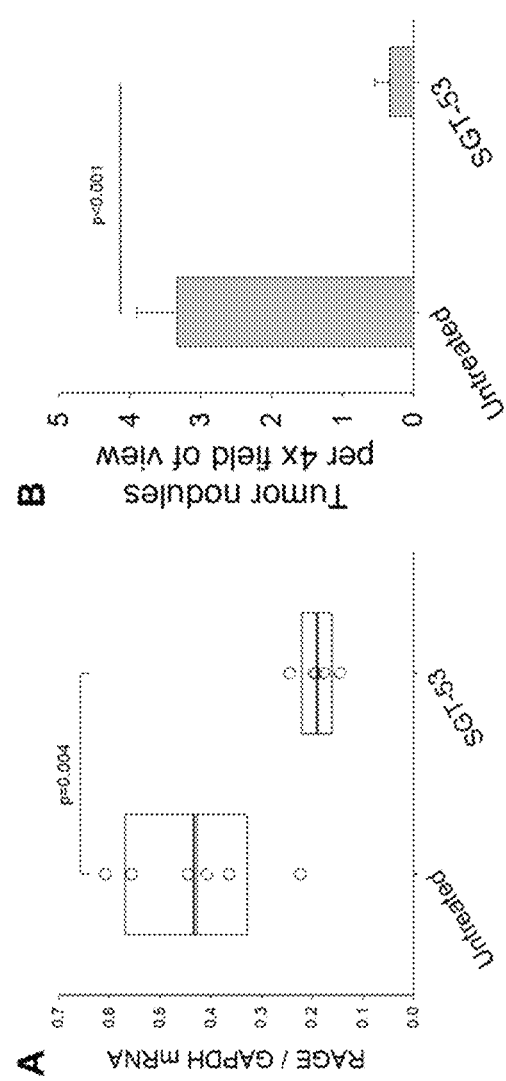
FIG. 9A-9B: SGT-53 treatment downregulates RAGE expression in the tumor and impairs the metastasis of breast cancer cells in the lung. BALB/c mice with subcutaneous 4T1 tumor were treated with SGT-53 (30 ug DNA/mouse, IV). Mice received treatments twice per week for 2.5 weeks. Tumors and lungs were harvested on day 17 after initiation of the treatment. (A) Expression of RAGE in the tumor tissue were assessed via TaqMan assay. (B) Metastatic lung nodules were microscopically counted per 4×field of view and plotted.

In our established model of lung metastasis of 4T1 breast cancer as described above in Example 3, a systemic treatment of SGT-53 significantly downregulated the expression of RAGE in the tumor and clearly inhibited metastasis development in the lungs of tumor-bearing mice (FIG. 9), confirming inhibition of RAGE via SGT-53 as a viable approach for treating metastatic cancers.

Figures 10A, 10B:
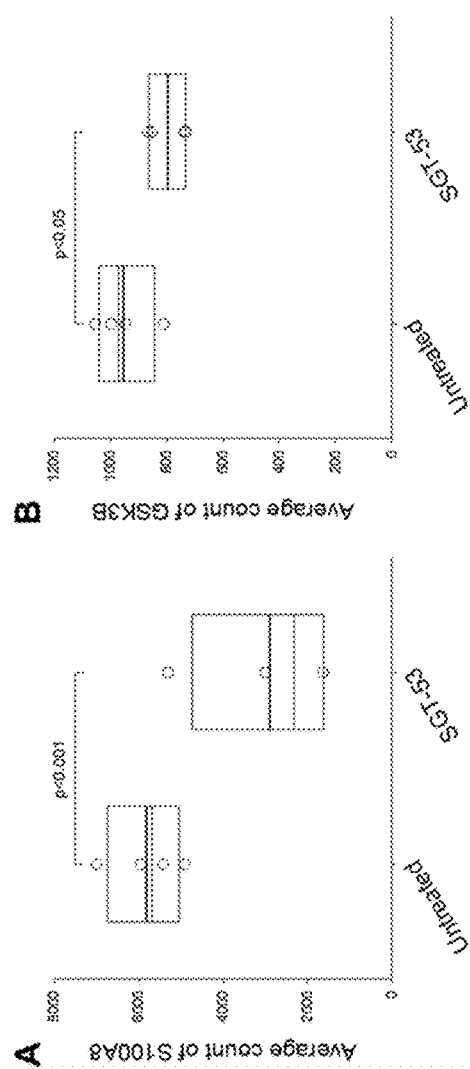
FIG. 10A-10B: Transcriptome analysis of S100A8 and GSK3B by NanoString nCounter Gene Expression Array. BALB/c mice with subcutaneous 4T1 tumor were treated with SGT-53 (30 ug DNA/mouse, IV). Mice received treatments twice per week for 2.5 weeks. Tumors were harvested on day 17 after initiation of the treatment. Expression of (A) S100A8 and (B) GSK3B in the tumor tissue were assessed via NanoString nCounter Gene Expression Array.

Moreover, RAGE binding to S100A8 promotes the migration and invasion of human breast cancer cells through actin polymerization and epithelial-mesenchymal transition. Moreover, RAGE binding to S100A8 promotes lung metastasis in vivo. In the 4T1 breast cancer model, we unexpectedly found, as determined via NanoString transcriptome analysis, that in addition to down modulating RAGE expression, SGT-53 treatment also significantly reduced the transcripts of S100A8 and its downstream target GSK3B, which have a direct effect on cell migration and vascular remodeling (FIG. 10A-10B). Consequently, SGT-53 treatment also unexpectedly circumvents RAGE through this mechanism to significantly inhibit breast cancer metastasis in the lungs of tumor-bearing mice.

Figure 11:
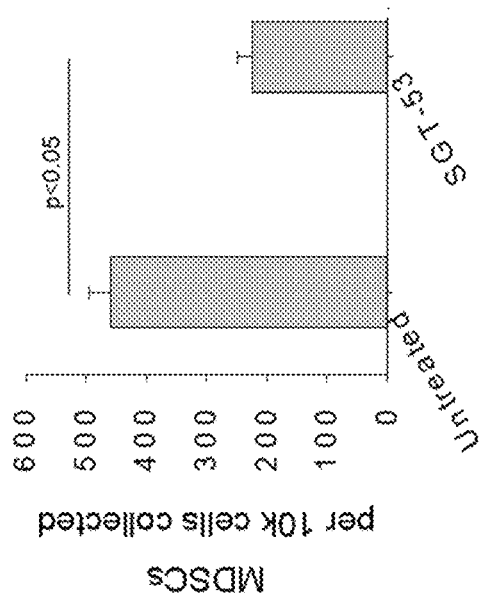
FIG. 11: SGT-53 treatment eliminates immunosuppressive MDSCs in tumor. Tumor cells were dissociated and immune cell infiltration was assessed via FACS. Immunosuppressive MDSCs (CD11b+Gr1+) were identified and shown in terms of absolute number of cells per 1×104 live cells collected.

Myeloid-derived suppressor cells (MDSCs) are a heterogeneous population of cells that constitute an important component of the immune regulatory system. While there are multiple different mechanisms that cancer cells employ, MDSCs are one of the key drivers of tumor-mediated immune evasion. In recent years, researchers have found that MDSCs and S100A8 operated together through a positive feedback loop to promote tumor development and metastasis. Specifically, the role of S100A8 in the recruitment of MDSCs into either primary or metastatic tumor microenvironments has been demonstrated, suggesting S100A8 as a potential target to reverse MDSC-mediated immunosuppression. We have observed the elimination of MDSCs in 4T1 tumors following SGT-53 treatment (FIG. 11). This result demonstrates again the unexpected benefit of treatment with SGT-53. By decreasing expression of S100A8 SGT-53 will overcome immunosuppression as well as inhibit metastasis development.

Importantly, based upon data from immunosuppressed murine models, it has been suggested that MDSCs play an important role in tumor progression and the metastatic process that is independent of their immunosuppressive properties. Consequently, targeting MDSCs either in combination with cancer immunotherapy or independently as part of an approach to inhibit the metastatic process could be a very clinically promising strategy. Based upon our unexpected findings, targeting MDSCs using SGT-53 would result in improved clinical benefit for cancer patients.

In fact, SGT-53 has been used in combination with anti-PD-1 antibody and chemotherapeutic agent carboplatin to treat a human patient with inflammatory breast cancer.

The patient was treated at Northwestern University, Chicago, IL. This patient was a postmenopausal woman with recurrent inflammatory breast cancer. The patient was treated with SGT-53, carboplatin and anti-PD-1 antibody. Over 12 weeks of time, the patient received 21 doses of SGT-53 at 3.6 mg DNA/infusion, 3 doses of 200 mg anti-PD-1 antibody and 9 doses of carboplatin.

The patient tolerated the treatment well demonstrating the safety of this approach. Although having previously failed treatment with the anti-PD-1 antibody alone, there was significant response to the combination treatment. PET/CT scan was done about 6 weeks after the start of the combination regimen. There was no evidence of progression and the lung nodule previously identified was no longer metabolically active. Test using circulating tumor DNA (ctDNA) revealed that the tumor was no longer detectable. Given that the patient had previously progressed on immune checkpoint inhibitor treatment, the investigator deemed that this combination regimen was unexpectedly beneficial to the patient.

Example 8

Combination of Anti-PD-1 and SGT-53 Effectively Inhibits GL261 Tumor Growth

In both subcutaneous and intracranial tumor models of GBM described in examples above, anti-PD-1 treatment as monotherapy had no demonstrable therapeutic benefit suggesting an inherent therapeutic resistance to anti-PD-1 checkpoint blockade. SGT-53 monotherapy showed a marginal antitumor effect but mediated immunogenic changes of tumor cells in vivo. However, when the combination regimen was given, a significant antitumor effect and survival benefit were observed accompanied by increased immune cell infiltrations within tumor.

These unexpected results suggest that introducing functional p53 by SGT-53 nanocomplex is able to boost antitumor immunity and sensitize GBM tumors to anti-PD-1 therapy. Combining anti-PD-1 treatment with SGT-53 nanocomplex could substantially expand the number of patients that benefit from anti-PD-1 and enhance the very poor prognosis for GBM patients.

GL261 is a syngeneic mouse model of GBM. For the subcutaneous GBM tumor model, 6 week old female C57BL/6 mice (Envigo) were inoculated with GL261 cells ($1.0\times10^6$ cells/mouse. Mice were systemically injected with either SGT-53 [1 to 100 ug DNA/injection/mouse, intravenous (i.v.), preferably 5 to 60, more preferably 10 to 40, e.g. 30 ug], anti-PD1 antibodies [1 to 500 µg/injection/mouse, intraperitoneal (i.p.), e.g. preferably 10 to 400, more preferably 20 to 300 e.g. 200 ug, RMP1-14, BioXCell] or the combination of both, twice weekly. The SGT-53 nanocomplex was prepared as described in Example 1.

Figures 12A, 12B, 12C:
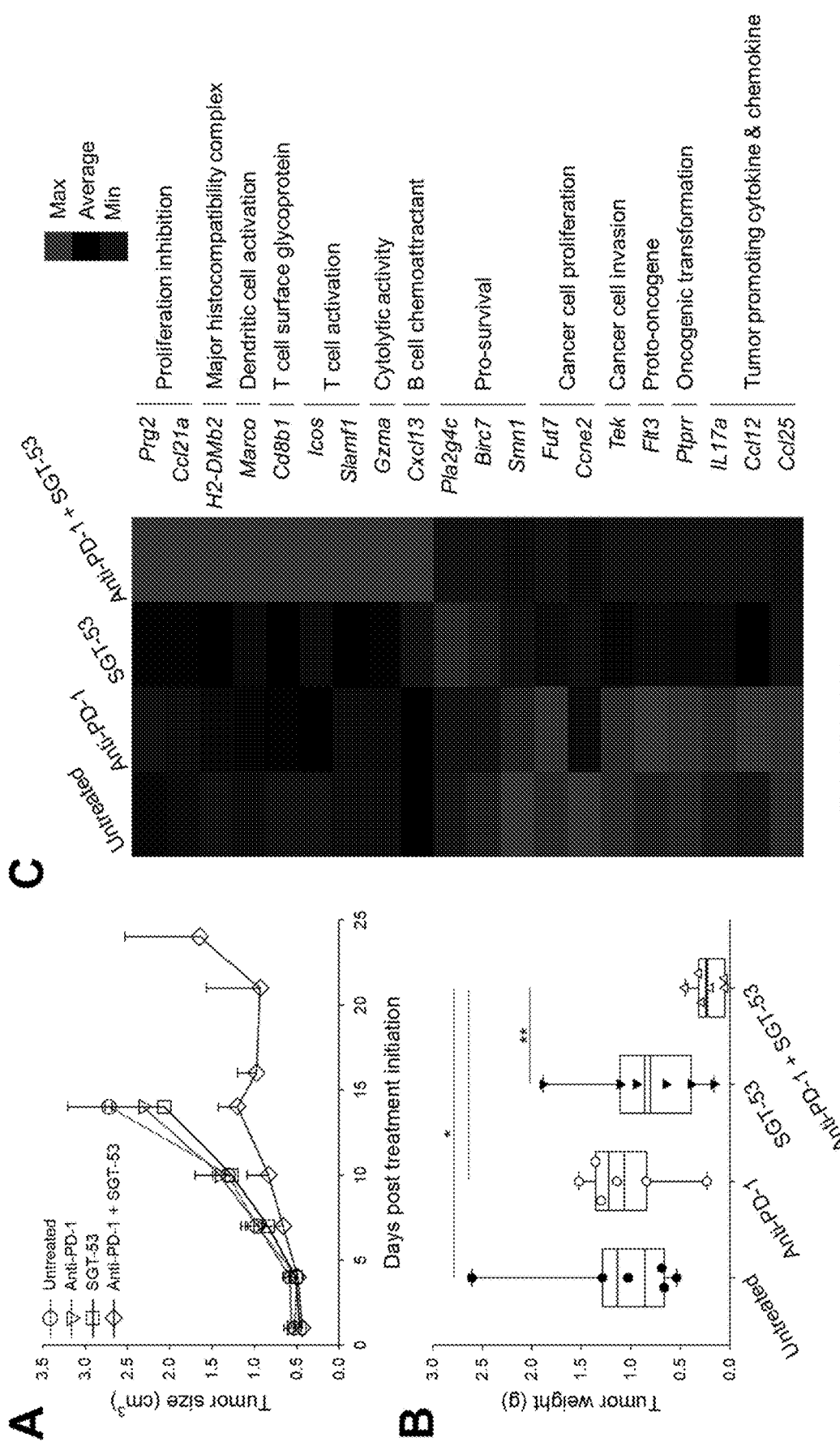

Mice bearing subcutaneously established GL261 tumors were treated with anti-PD-1, SGT-53 or the combination of both treatments. No significant inhibition of tumor growth was seen with anti-PD-1 monotherapy indicating that GL261 tumors display inherent therapeutic resistance to anti-PD-1 checkpoint blockade (GBM FIG. 12A). SGT-53 treatment alone resulted in no significant inhibition of GL261 tumor growth either. However, the combination treatment resulted in a significantly retarded tumor growth leading to markedly smaller tumors compared to those in mice given either agent individually. This synergistic activity was unexpected based upon the literature since genes usually cannot cross the BBB. Sixteen days post treatment initiation, the tumors were harvested and the average tumor weight was compared among the treatment groups (FIG. 12B). The tumors from animals that received combination treatment showed significantly decreased weight (225.5±43.0 mg) compared to untreated control (1132.9±212.5 mg) or treated with either single agents (1064.3±128.9 mg and 855.7±168.2 mg for anti-PD-1 and SGT-53, respectively).

Transcriptome analysis of GL261 tumors was performed using the NanoString nCounter®. For the NanoString, two commercially available gene panels (mouse PanCancer Pathways and mouse PanCancer Immune profiler) containing total 1330 unique genes were used. RNA from GL261 tumor was hybridized with probes and counted on nCounter® analyzer (NanoString Technologies). Raw data were analyzed using nSolver 3.0 software (NanoString Technologies). The NanoString analysis revealed modulation of genes linked to either cancer progression (proliferation, invasion) or immune activation (antigen presentation, T cell activation) by the combination treatment (FIG. 12C).

Immunohistochemical analysis was also performed on the tumors. The mice were euthanized after completing treatment (day 17) or when the control animals developed excessive tumor burden. Harvested tumors were fixed in 10% neutral buffered formalin, paraffin embedded, and sectioned at 5 um. Tumor sections were stained for active caspase-3 (Casp3, Cell Signaling Technology) or granzyme B (GzmB, AbCam) antibodies. Images were captured using Olympus DP70 camera on Olympus BX61 microscope. In tumors treated with combination of SGT-53 and anti-PD-1, immunohistochemical analysis revealed increased Casp3 staining indicative of tumor cell apoptosis compared to tumors in untreated mice or those treated with single agent treatments (FIG. 12D, E). We also observed a significant increase of GzmB-positive staining (FIG. 12D, F) in tumors indicating increased cytotoxic T cell (CTL) immunity following the combination treatment compared to controls. These data indicate that the combination of an anti-PD-1 antibody and SGT-53 is more effective than either agent individually in inhibiting tumor growth and inducing apoptosis in this tumor model.

Example 9

Combination of Anti-PD-1 and SGT-53 Enhances Immune Responses In Vivo

To investigate whether the observed antitumor response is associated with enhanced host immunity, we assessed tumor-infiltrating immune cells using flow cytometry analysis. For Flow Cytometry, the tumors were dissociated by enzymatic digestion in Hank's balanced solution containing 1 mg/mL collagenase D (Roche) and 2 mM DNase I (Sigma) for 1 h at 37° C. Subsequently, the cells were labelled with Zombie-NIR viability dye (BioLegend) and stained with antibodies against FAS, CD206, CD86, ICAM1, H-2Kb/H-2Db, CD45, CD31, CD3, CD4, CD8a, FoxP3, GzmB (all from BioLegend), CD11b (BD Biosciences), and CRT (Novus Biologicals). Cells were analyzed by LSRFortessa flow cytometer (BD Biosciences).

Figures 13A, 13B, 13C, 13D:
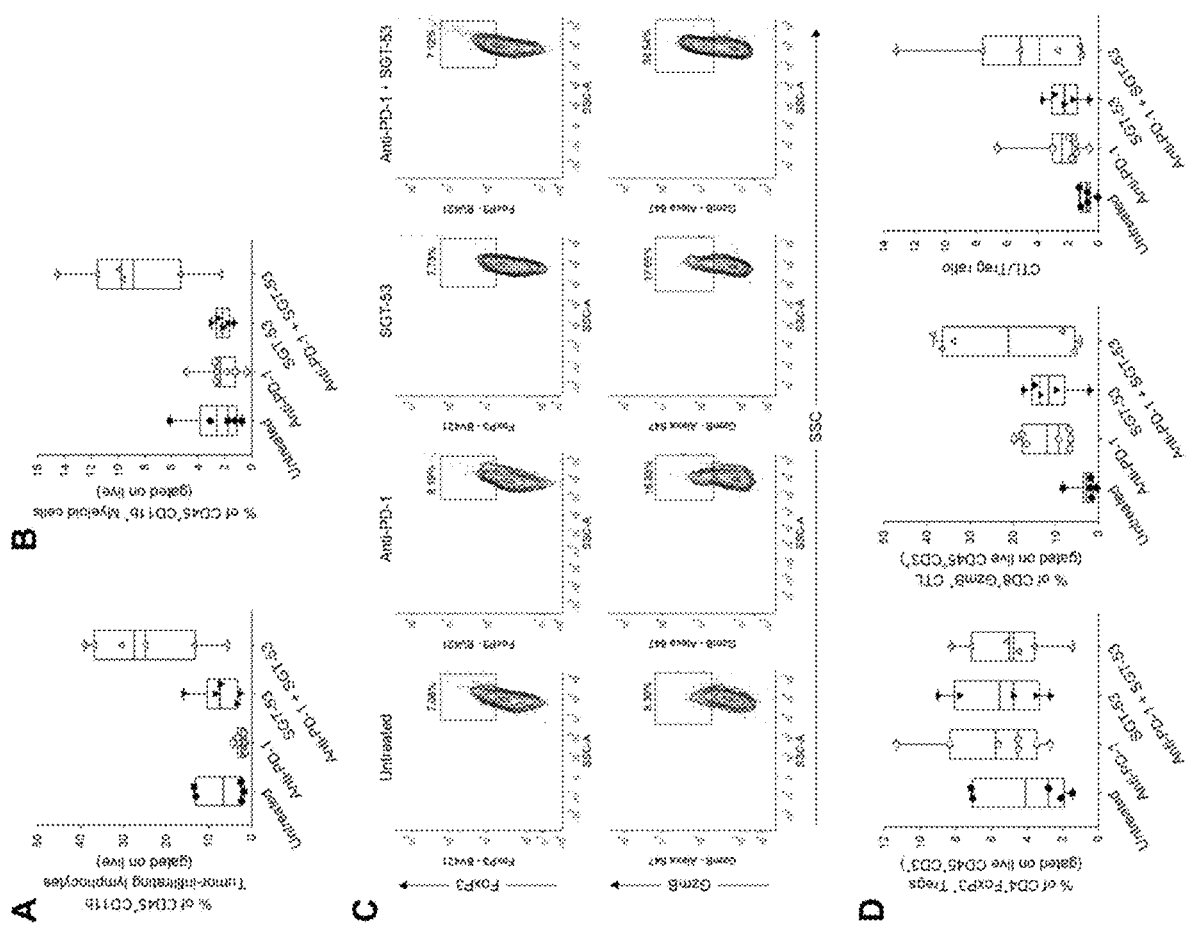
FIG. 13A-13D: The combination of anti-PD-1 and SGT-53 enhances immune responses in vivo. Tumor cells were dissociated and tumor-infiltrating immune cells were assessed via flow cytometry. (A) Tumor-infiltrating lymphocytes and (B) myeloid cells were identified by gating CD45+CD11b- live cells and CD45+CD11b+ live cells respectively. Red lines indicate average percentage of cells. (C) Representative FACS plots of Treg (CD3+CD4+FoxP3+, upper panels) and CTL (CD3+CD8+GzmB+, lower panels) are shown. (D) Quantifications of Treg (left panel) and CTL (middle panel) were plotted in graphs. The ratio of CTL/Treg was plotted (right panel). Red lines indicate average percentage of cells. $*p<0.001$, $**p<0.05$.

In tumors treated with anti-PD-1 plus SGT-53, there was a significant increase of both CD45+CD11b lymphocytes (FIG. 13A) and CD45+CD11b+ myeloid cells among isolated tumor cells (FIG. 13B). Further analysis of regulatory T cells (Treg, $CD3^+CD4^+FoxP3^+$) and CTLs ($CD3^+CD8^+GzmB^+$) showed the substantially increased number of CTLs present in tumors with the combination treatment, while the number of Treg remained similar through the groups (FIG. 13C, D). Unexpectedly, an increase in the ratio of CTLs and Tregs, which is associated with improved prognoses in many cancers, was observed only in tumors with the combination treatment (FIG. 13D). However, neither anti-PD-1 antibody nor SGT-53 monotherapy led to significant increase of CTL/Treg ratio. Together, these data demonstrate that SGT-53 in combination with anti-PD-1 can increase immune cell infiltration within tumor and change tumor microenvironment into immunologically 'hot' tumor.

Example 10

SGT-53 Increases Immunogenicity of Tumor Cells

Figures 14A, 14B, 14C:
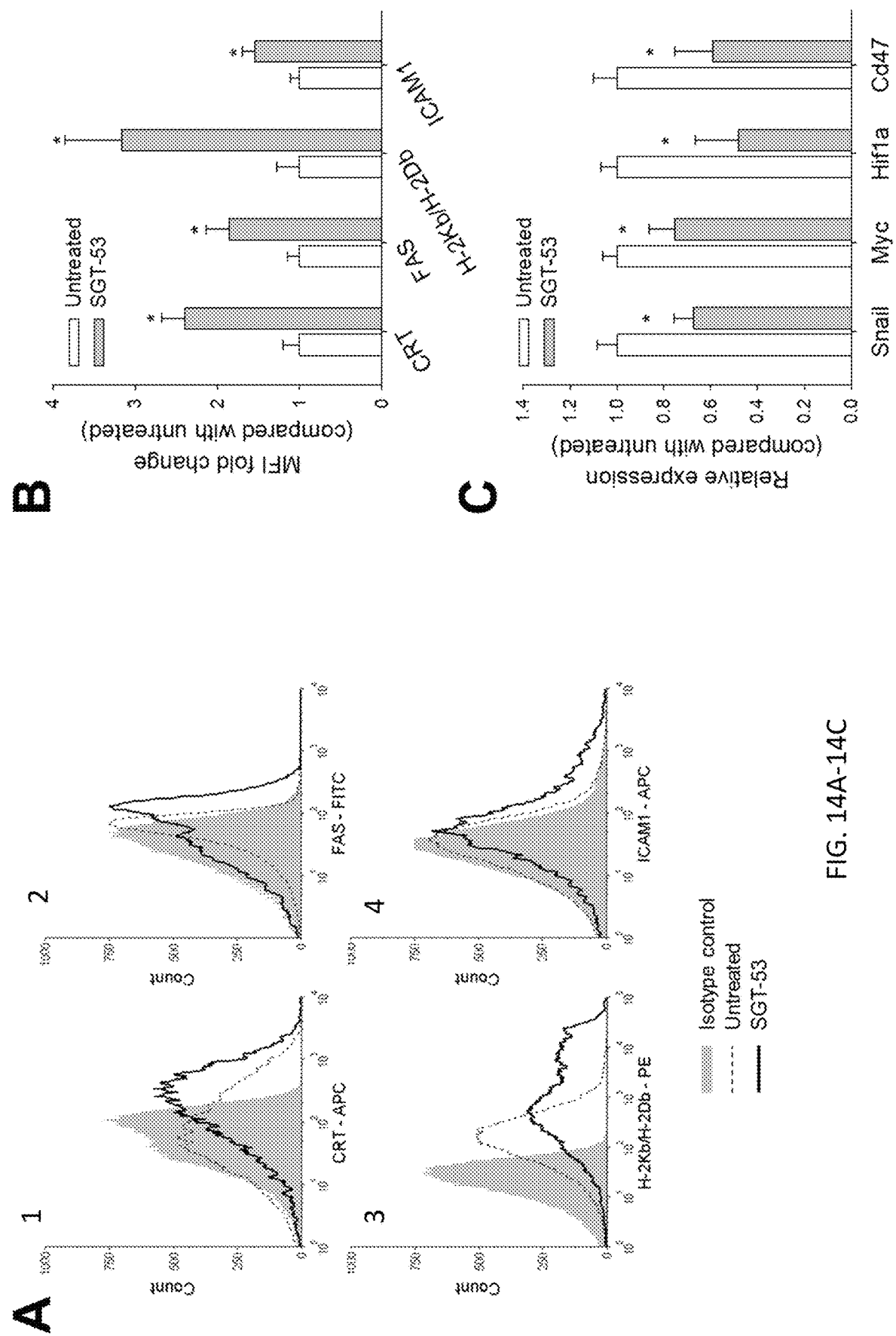
FIG. 14A-14C: SGT-53 increases immunogenicity of tumor. Mice bearing GL261 tumor were intravenously treated with SGT-53 (30 μg DNA). Tumor cells were dissociated and identified by gating CD45-CD31- live cells. (A) (1-4) Expression of cell surface components of immunogenicity was assayed via flow cytometry. (B) The fold changes of mean fluorescence intensity (MFI) were plotted in comparison with those in tumor from untreated mice. (C) Representative immunohistochemical staining of CD47 are shown. Scale bar, um. (D) Changes in mRNA level of CD47 and CD47-associated genes in GL261 tumors treated with SGT-53 were assessed by quantitative RT-PCR. The fold-changes relative to untreated tumor are shown. *p<0.05.

To evaluate whether introduction of wtp53 altered immunogenicity of tumor cells, mice bearing subcutaneous GL261 tumors, induced as described above in Example 8, were treated with SGT-53 via tail vein injection, and the impact of SGT-53 treatment on a number of immune-relevant markers examined. Flow cytometry analysis revealed a significantly increased surface expression of immune cell recognition molecules including calreticulin (CRT), FAS, MHC class I ($H-2K^b/H-2D^b$), and ICAM1 after SGT-53 treatment in vivo (FIG. 14A, B). Notably, we observed an increased surface expression of endoplasmic reticulum (ER) protein CRT, an indicative of immunogenic cell death (ICD). With SGT-53 treatment, immunohistochemical analysis of GL261 tumor showed reduced expression of CD47 compared with untreated tumors (FIG. 14C). Similarly, quantitative RT-PCR analysis of SGT-53 treated tumors showed a significant downregulation of Cd47 mRNA as well as Snail, Myc, and Hif1 mRNAs that are shown to regulate CD47 expression in comparison with untreated tumors. Importantly, CD47 serves as a "don't eat me signal" and loss of CD47 leads to phagocytosis (67). Thus, decreased CD47 signals along with the increased CRT signals can promote immunogenic phagocytosis by phagocytic innate cells for antigen presentation and turn on the cancer immunity cycle. Collectively, these data demonstrate the unexpected result that expression of functional p53 is responsible for both induction of ICD and alterations in the immunogenicity of GL261 cells. In short, the tumors treated with SGT-53 appear to be more immunologically 'hot', and this change would be expected to augment adaptive checkpoint inhibitors against 'cold' tumors such as GBM.

Example 11

Combined SGT-53 and Anti-PD-1 Treatment Leads to Improved Survival in an Intracranial GBM Model To determine in vivo efficacy of combinatorial SGT-53 and anti-PD-1 therapies, we performed a survival study using intracranially implanted GL261 tumors. For the intracranial GBM tumor model, 6 week old female albino C57BL/6 mice (Charles River) were stereotactically inoculated with GL261 cells ($2.0 \times 10^5$ cells/mouse). Mice were systemically injected with either SGT-53 [1 to 100 ug DNA/injection/mouse, intravenous (i.v.), preferably 5 to 60, more preferably 10 to 40, e.g. 30 ug], anti-PD1 antibodies [1 to 500 μg/injection/mouse, intraperitoneal (i.p.), e.g. preferably 10 to 400, more preferably 20 to 300 e.g. 200 ug, RMP1-14, BioXCell] or the combination of both, twice weekly. The SGT-53 nanocomplex was prepared as described in Example 1.

Figures 15A, 15B:
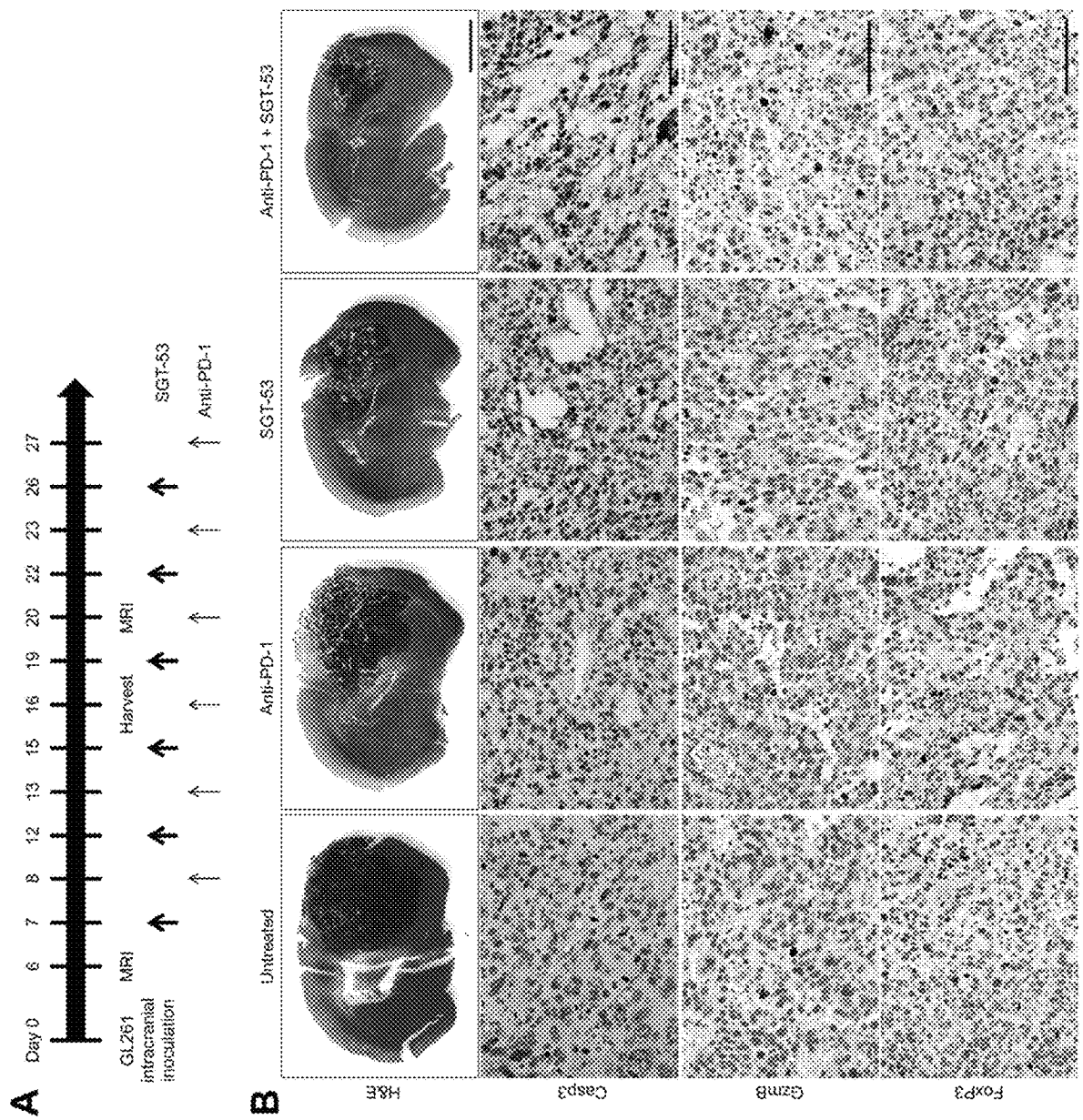
FIG. 15A-15H: Combination treatment enhances tumor growth inhibition and survival in intracranial GL261 tumors. (A) Treatment schedule. Based on the MRI on day 6, tumor-bearing mice were randomized to therapy with anti-PD-1 (200 ug antibody), SGT-53 (30 ug DNA) or combination of both (N=10). (B) Histological examination of mouse brain on day 16. Representative H&E (Scale bar, 2 mm) and immunohistochemical staining of Casp3, GzmB and FoxP3 (Scale bars, 100 um) are shown. Quantification of (C) Casp3, (D) GzmB and (E) FoxP3 signal was performed using IHC-Profiler plugin in ImageJ. (F) Representative MRI images acquired on days 6 and 20. Yellow dashed lines surround tumor area. (G) A volumetric assessment of brain tumor (N=5). Red lines indicate average tumor volume. *p<0.001, **p<0.05. (H) Kaplan-Meier survival curves (left panel, N=6). Median survival and statistical significance were determined by log-rank testing and summarized in the table (right panel).

Six days post tumor inoculation, the presence of tumor was confirmed by MRI and treatment was started using the schedule shown in FIG. 15A.

Figures 15C, 15D, 15E, 15F, 15G, 15H:
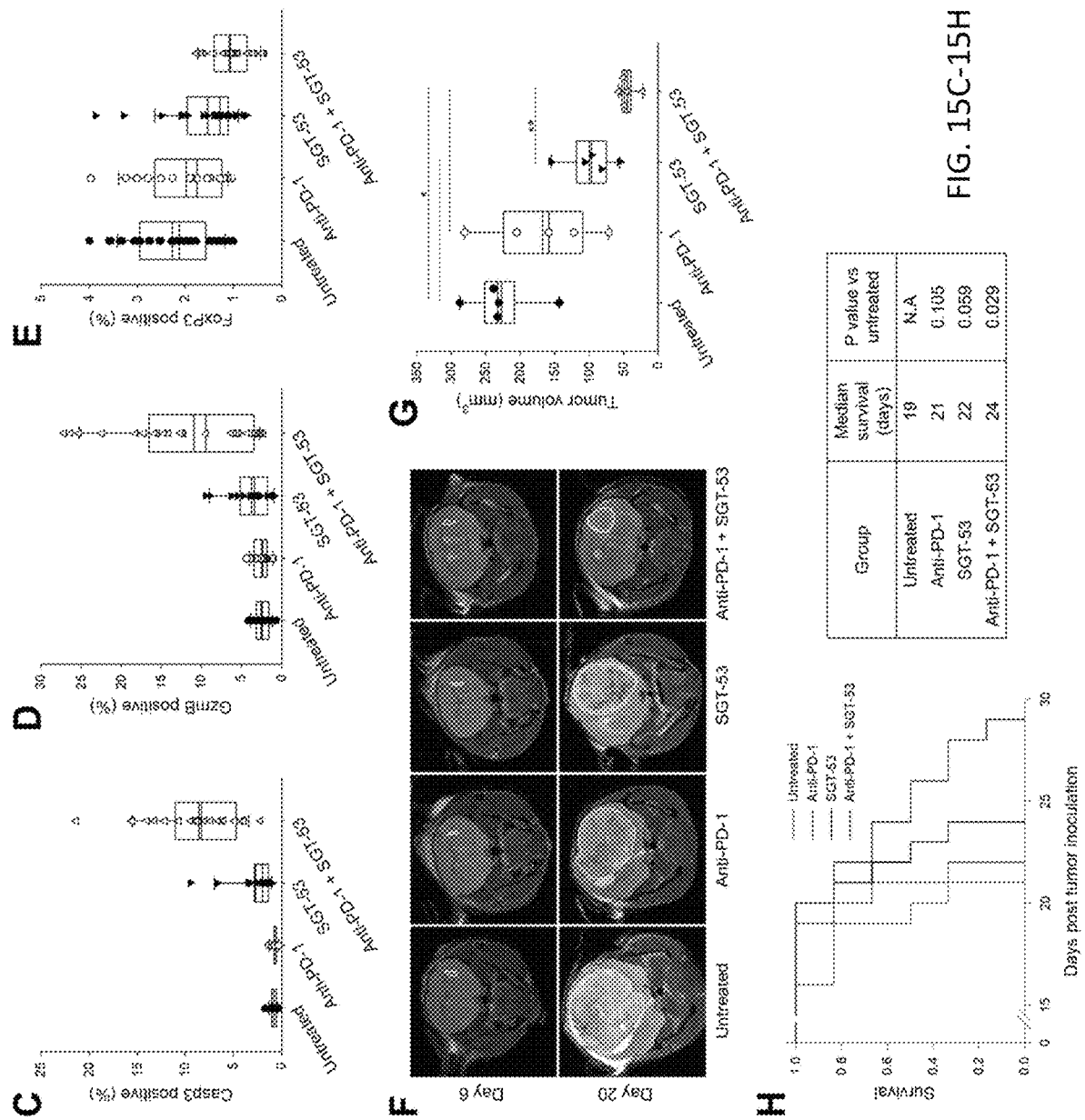

The tumors were examined by immunohistochemistry. The mice were euthanized after completing treatment (day 17) or when the control animals developed excessive tumor burden. Harvested tumors were fixed in 10% neutral buffered formalin, paraffin embedded, and sectioned at 5 um. Tumor sections were stained for active caspase-3 (Casp3, Cell Signaling Technology) or granzyme B (GzmB, AbCam) antibodies. Images were captured using Olympus DP70 camera on Olympus BX61 microscope. Similar to the subcutaneous tumor study, here also we observed the unexpected results of enhanced antitumor effect of anti-PD-1 plus SGT-53 combination treatment was evident on day 16 (FIG. 15B). We observed a significant increase of Casp3 (FIG. 15C) and GzmB (FIG. 15D) positive staining together with a significant decrease of FoxP3 (FIG. 15E) in tumors indicating increased CTL immunity and tumor cell apoptosis following treatment with anti-PD-1 plus SGT-53 compared to untreated control or monotherapies. MRI-based measurement of tumor volume further revealed a significant inhibition of tumor growth by combined treatment (FIG. 15F, G), while anti-PD-1 alone showed no antitumor effect and SGT-53 alone showed a moderate antitumor effect compared with untreated controls. We have observed that all of the untreated mice had succumbed to their disease prior to day 21 and no animals survived beyond day 24 receiving either monotherapies, demonstrating no significant survival benefit by either single agent treatments (FIG. 15H). However, mice receiving SGT-53 plus anti-PD-1 therapy demonstrated increased survival. Collectively, these observations supports the unexpected findings that the combination of SGT-53 and anti-PD-1 antibody was more efficacious as an immunotherapy regimen than the checkpoint blockade alone and thereby would improve outcomes for cancer patients.

Example 12

SGT-53 Modulates Polarization of Macrophages

Macrophages, as highly plastic cells, play an important role in tumor immunity and regulates the growth or regression of tumors. Specifically, anti-inflammatory M2 macrophages predominate in human cancers and actively stimulate tumor growth, while pro-inflammatory M1 macrophages can slow or stop cancer growth (68). Here, we examined the effects of SGT-53 on tumor-associated macrophage phenotypes both in vitro and in vivo.

Figures 16A, 16B, 16C, 16D, 16E, 16F:
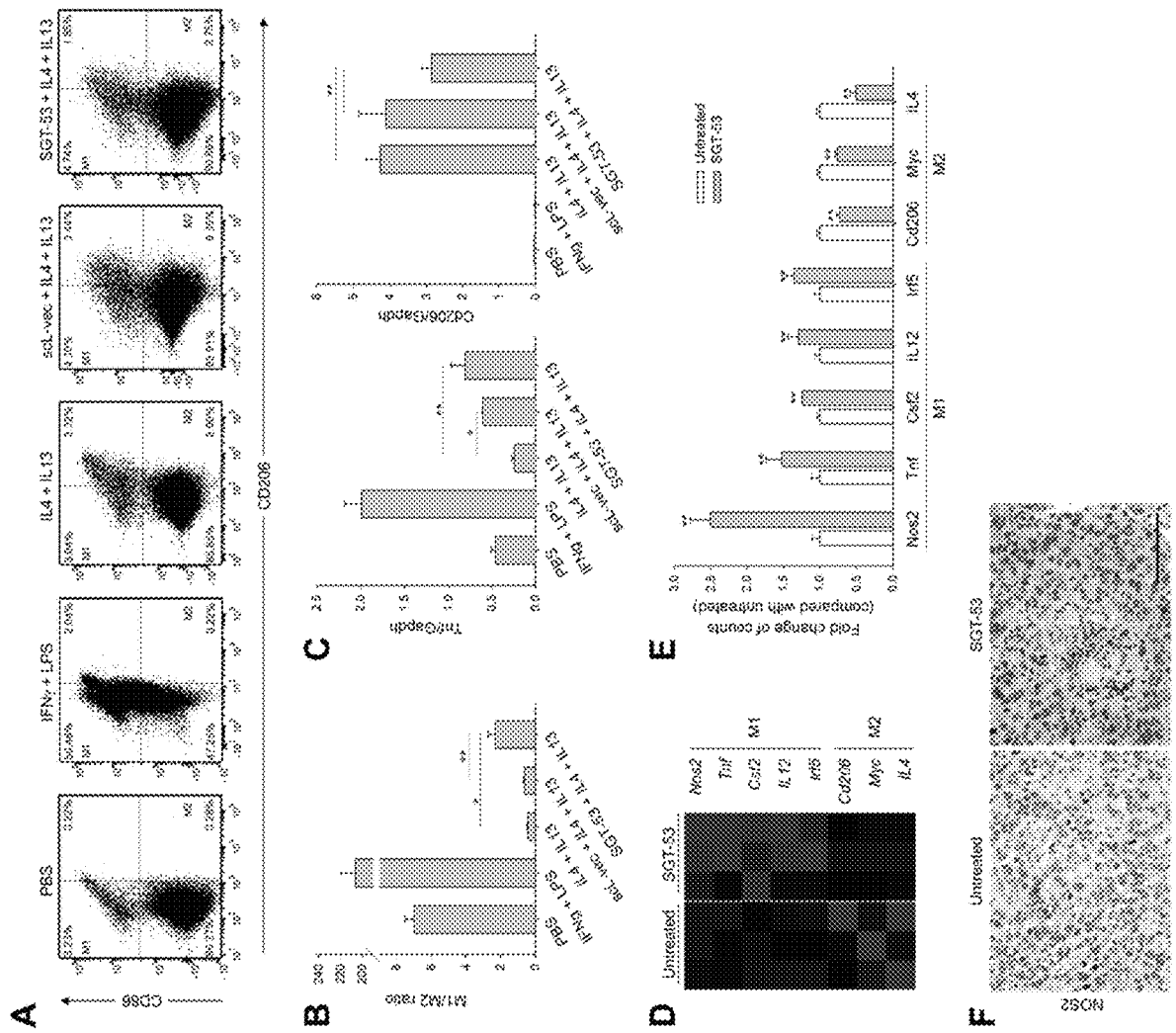
FIG. 16A-16F: SGT-53 regulates polarization of macrophages. M1 or M2 polarization of Raw 264.7 cells were induced using IFNgamma (10 ng/ml)+LPS (100 ng/ml) for M1 or IL4 (20 ng/ml)+IL13 (20 ng/ml) for M2. Prior to the incubation with IL4+IL13, Raw 264.7 cells were treated with either SGT-53 or scL-vec nanocomplex for 24 h. (A) The shift between M1/M2 phenotypes was evaluated 24 h later by flow cytometry (M1=CD86+CD206−, M2=CD86-CD206+ using CD11b+F4/80+ macrophage gate). (B) The ratio of M1/M2 macrophages was plotted. (C) Expression of genes associated with M1 and M2 polarization was assessed by quantitative RT-PCR in Raw 264.7 cells. (D) Changes in gene expression of M1- and M2-associated genes were also assessed in vivo using GL261 tumors treated with SGT-53 by NanoString assay. (E) The fold change of average counts were plotted in comparison with those in tumor from untreated mice. (F) Representative immunohistochemical staining of NOS2 and ARG1 are shown. Scale bar, 100 um. *p<0.001, **p<0.05.

Firstly, mouse macrophage Raw 264.7 cells were treated with SGT-53 and reprogrammed towards M2 phenotype by Th2 cytokines (IL4 and IL13). The cytokine treatment substantially increased M2 phenotype ($CD11b^+F4/80^+CD86^-CD206^+$, from 0.28 to 8.00%), while SGT-53 treatment clearly suppressed the reprogramming of Raw 264.7 cells toward M2 phenotype (2.75%) (FIG. 16A). Concomitantly, SGT-53 treatment also slightly increased M1 phenotype ($CD11b+F4/80^+CD86^+CD206^-$, from 3.23 to 4.74%), significantly increasing M1/M2 ratio (FIG. 16B). However, the control nanocomplex scL-vec did not have significant effect on the shift between M1/M2 phenotypes.

We also performed RT-PCR on the treated cells. Total RNAs were extracted from the cell pellet using PureLink RNA Mini Kit (Ambion) and reverse transcribed using Superscript IV VILO Master Mix (Life Technologies). PCR was performed in triplicate using TaqMan Fast Advanced Master Mix (Life Technologies) and TaqMan gene expression assays for human p53, PD-L1 and GAPDH (Life Technologies). Relative mRNA expression was analyzed using StepOne Software v2.3 via the ΔΔCt method with normalization to GAPDH mRNA. This quantitative RT-PCR analysis showed a significant upregulation of M1-related cytokine Tnf (M1 marker) and downregulation of Cd206 (M2 marker) after SGT-53 plus Th2 cytokine treatments (FIG. 16C). These data suggest that introduction of p53 under M2-polarizing condition thwarts the establishment of the M2 phenotype. Modulation of macrophage polarization by SGT-53 was further investigated in vivo. Employing NanoString assay, as described above, changes in expression of M1 and M2 genes were assessed in GL261 tumors from animals treated with SGT-53 (FIG. 16D). Similar to in vitro results, SGT-53 treatment significantly increased the average counts of M1 genes (Nos2, Tnf, Csf2, IL12, and Irf5) and significantly decreased the average counts of M2 genes (Cd206, Myc, and IL4) (FIG. 16E). Immunohistochemical analysis with NOS2 (M1 marker) and ARG1 (M2 marker) further confirmed the unexpected reduction of M2 macrophages in GL261 tumors with SGT-53 treatment compared with untreated tumors (FIG. 16F). Thus, our results show that SGT-53 alters tumor associated macrophage phenotype and may contribute to inhibition of tumor progression.

Example 13

Use of the Combination of SGT-53 with Pembrolizumab and Carbopatin for the Treatment of Breast Cancer Inflammatory breast cancer (IBC) is a rare but aggressive form of Breast Cancer (BC) accounting for only 2-4% of BC cases. Despite improvements in outcomes with multimodality aggressive therapy, IBC disproportionately accounts for about 10% of BC mortality. Prognosis is significantly worse than locally advanced non-inflammatory breast cancer with a median survival of 2.9 vs 6.4 years.

In addition to these clinical and phenotypic features, IBC has recurring molecular abnormalities that potentially offer insight into avenues for novel therapeutic strategies using targeted agents. Mutations in Tumor Suppressor Gene P53 (TP53) are the most commonly seen mutations in IBC, with 57-62% of patients harboring TP53 aberrations. These mutations are associated with decreased response to chemotherapy and worse survival outcomes. A subset of IBC tumors also have infiltration of cytotoxic CD8+ T cells, PD-L1 staining by immunohistochemistry, and PD-L1 mRNA expression. Thus, women with IBC meet the criteria for treatment with the combination of SGT-53, Pembrolizumab and Carboplatin.

After diagnosis and assessment of tumor size by CT or MR, patients with IBC are treated with the three drugs using the following schedule and dosages of the drugs:

TABLE 1

Drug Schedule and Dosing One cycle lasts 21 days. Multiple cycles are administered.

| Agent | Dose | Route | Schedule | Cycle Length | Supportive Therapies |
|---|---|---|---|---|---|
| SGT-53 | 3.6 mg | IV over 2 hours | Days 1 (±1-2 days), 8 (±1- 2 days), and 15 (±1-2 days) of each cycle | 21 days | IVF × 2 hours after administration of SGT-53 |
| Pembrolizumab | 200 mg | IV over 30 min | Day 3 (2 days post-SGT-53) of each cycle | | As needed |
| Carboplatin | AUC 5 | IV infusion | Day 3 (2 days post-SGT-53) of each 3 week cycle | | Per institutional standards, as needed |

40

SGT-53 will be prepared as follows: The cationic liposome consisting of 1,2-dioleoyl-3-trimethylammonium propane (DOTAP) and dioleolylphosphatidyl ethanolamine (DOPE), referred to as Lip, is prepared using the ethanol injection method as detailed in the specification. TfRscFv/Lip/p53 (SGT-53, scL encapsulating plasmid DNA encoding human wtp53) complex is prepared by simple mixing of Lip with TfRscFv and plasmid DNA. The ligand (TfRscFv) is mixed with the liposome by inversion or gentle stirring at 25-30 RPM for 1 minute at room temperature and at a ligand: liposome ratio in the range of about 1:0.001 to 1:500 (ug:nmole), preferably about 1:10 to about 1:50 (ug:nmole). With TfRscFv as the ligand, useful ratios of ligand to liposome typically are within the range of about 1:5 to 1:40 (ug:ug), preferably 1:30 (ug:ug). The mixture is held at room temperature for 10-15 minutes. The pSCMV-53 plasmid DNA is then mixed with the immunoliposome at room temperature and at an plasmid:lipid ratio in the range of about 1:01 to about 1:50 (ug:nmole), preferably about 1:10 to about 1:24 (ug:nmole) or the ratio of plasmid DNA to liposome is typically within the range of about 1:6 to 1:20 (ug:ug), preferably 1:10 (ug:ug). To form the final SGT-53 complex, the plasmid is mixed with the Ligand:liposome by inversion or gentle stirring at 25-30 RPM for 1 minute at room temperature. The mixture is held at room temperature for 10-15 minutes, after which sucrose or dextrose, at a final concentration of 5-10%, is added to the SGT-53 preparation. The SGT-53 can be used immediately after preparation or lyophilized to dryness and stored at −20 to 8° C. and stored prior to use. If lyophilized, SGT-53 is reconstituted by the addition of sterile, endotoxin free water. After swirling for 30 sec to 1 min to dissolve. The vial is sonicated in a bath sonicator at 37 kHz, 100% power for 1 to 10 minutes at 31-34° C. for 1 to 10 minutes. The vial is swirled gently every 30-60 sec during the sonication.

The size (number average) of the final complex prepared by this method is between about 10 to 800 nm, suitably about 20 to 400 nm, most suitably about 25 to 200 nm with a zeta potential of between about 1 and 100 mV, more suitably 10 to 60 mV and most suitably 25 to 50 mV as determined by dynamic light scattering using a Malvern Zetasizer ZS.

Example 14

Use of scL-RB94 (SGT-94) in Phase I Clinical Trial for Genitourinary Cancer

For all in vitro, pre-clinical in vivo, and even use in human clinical trials described in the examples below, the scl-RB94 (also called SGT-94) nanosized complex was prepared as described in Example 1.

In a completed Phase 1 trial that evaluated SGT-94 as single agent in patients with advanced genitourinary cancers, not only was a good safety profile for this investigational agent observed, but partial and complete patient responses (PR and CR, respectively) and disease stabilization were observed (one complete response, two partial responses & three stable diseases in the 11 evaluable patients enrolled in the trial) (Grant 16). Moreover, intravenously administered SGT-94 effectively delivered its plasmid payload to metastatic bladder tumor cells in the lungs of one of the patients enrolled in the trial. Two relatively small (0.5-1.7 cm) tumor nodules (labeled T1 and T2) were removed from the patient's lung and polymerase chain reaction (PCR) was employed to show that the RB94 DNA payload of SGT-94 was present in both metastatic tumors (FIG. 17A). In addition, we demonstrated that the RB94 protein was expressed in the tumors using western blotting (FIG. 17B).

The specificity of the tumor-targeting of the scL nanocomplex delivery system was confirmed by showing that RB94 protein produced from the investigational agent, SGT-94 was seen in both T1 and T2, but no RB94 protein was seen in adjacent normal lung tissue. These data demonstrate that in patients with NSCLC, scL-RB94 will be able to reach even relatively small nodules of NSCLC cells in the lungs and that delivery of its plasmid DNA payload to these tumor cells will result in expression of the RB94 protein, a powerful tumor suppressor that selectively induces tumor cell death through induction of apoptosis. scL-RB94 can be thought of as a "double targeted agent" in that the scL delivery vehicle targets tumors but not normal tissue and its payload is a gene encoding a tumor suppressor that is active in tumor cells while leaving normal cells unharmed.

Example 15

Systemic Treatment with scL-RB94 (SGT-94) Inhibits NSCLC Tumor Growth in Mice

Based on the promising results from the Phase I trial with SGT-94 in genitourinary cancer and the urgent need for improved treatment regimens for NSCLC, we performed experiments to assess the use of this gene therapy nanomedicine in treating NSCLC. NSCLC tumors are among those that overexpress TfR (17, 18) and so will be targeted by the scL delivery system.

Female athymic nude mice, 5-6 week old (Envigo), were inoculated subcutaneously with human NSCLC H358 cells in matrigel ($1.2 \times 10^6$ cells/site), human NSCLC H292 cells in matrigel ($2.0 \times 10^6$ cells/site), or human NSCLC H596 cells in matrigel ($5 \times 10^6$ cells/site). For the H292 study, one tumor was inoculated above the tail on each mouse. Tumors were allowed to grow until they averaged 200-400 mm3 and then were divided into treated and untreated groups with equal tumor volumes. Treated mice were systemically injected with scL-RB94 (30 μg DNA/injection/mouse) intravenous (IV) via the tail vein every $4^{th}$ day starting on day 1 for a total of 5 injections. All mice were harvested on day 19 (two days after the last treatment).

Figures 18A, 18B:
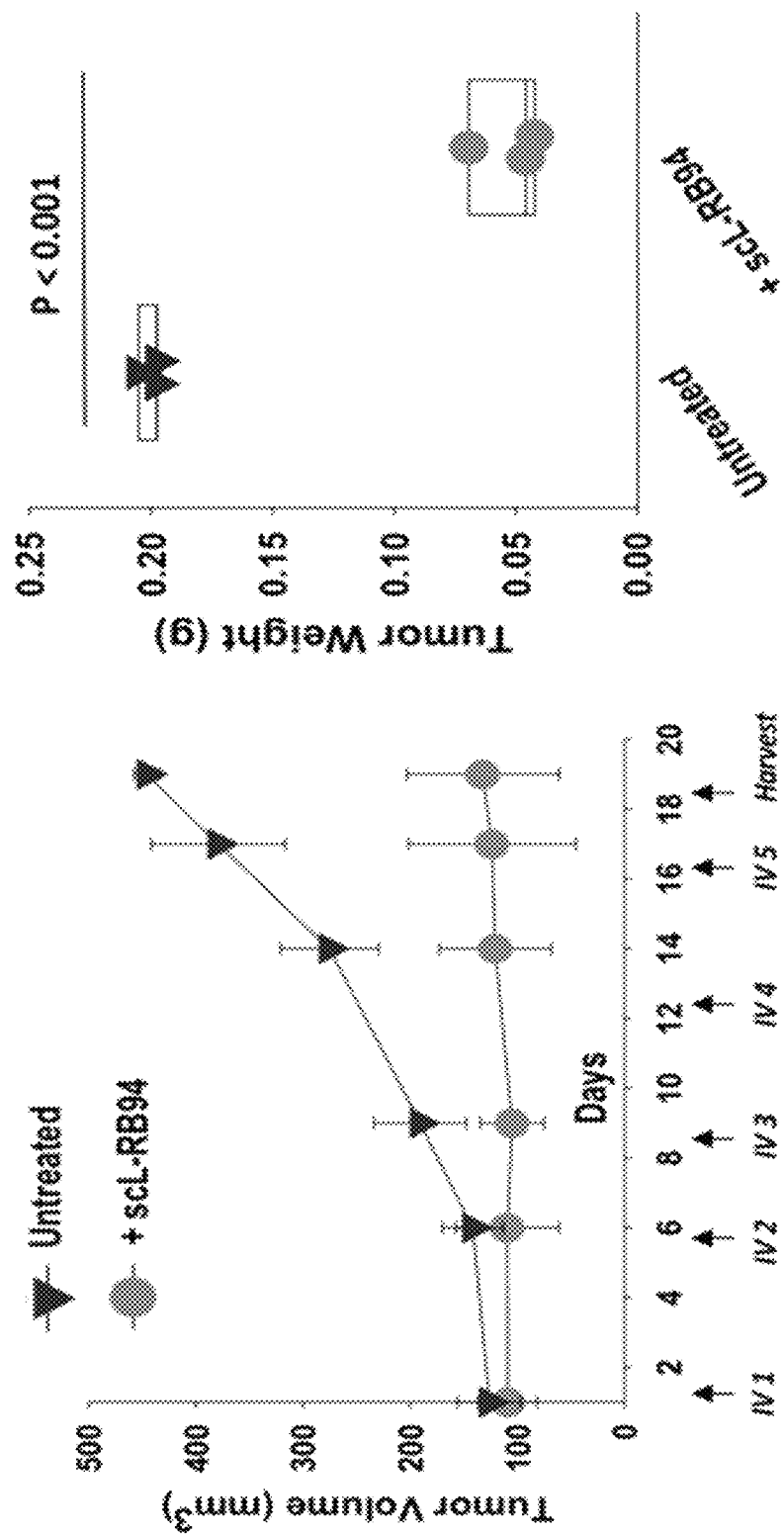
FIG. 18A-18B: scL-RB94 inhibits the growth of human H292 NSCLC tumors in athymic mice as assessed by tumor volume (FIG. 18A) or tumor weight upon harvest (FIG. 18B). Arrows in the FIG. 18A indicate timing of intravenous injections of scL-RB94 (30 ug plasmid DNA per injection).
Figures 19A, 19B:
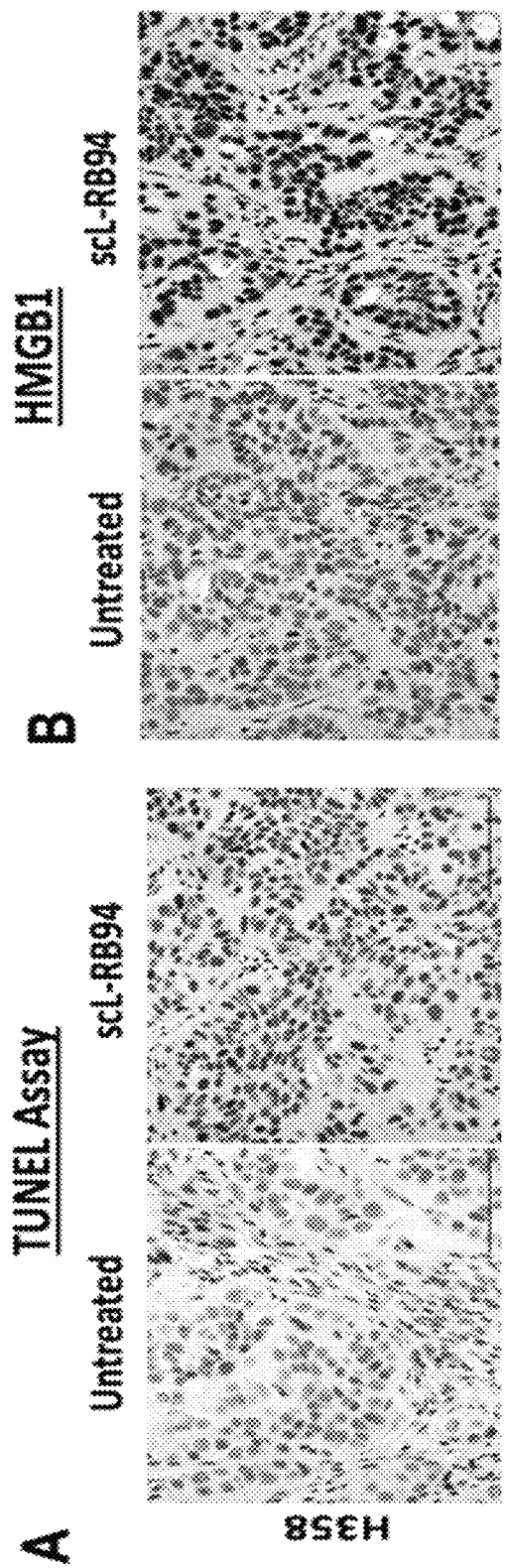
FIG. 19A-19B: scL-RB94 increases apoptosis in NSCLC tumors. Athymic mice bearing H358 NSCLC tumors were treated twice with intravenously injected scL-RB94. Tumors were sectioned and stained for TUNEL, an indicator of apoptosis (FIG. 19A). Tumor sections were also examined by immunohistochemistry for high-mobility group box 1 (HMGB 1) protein, a marker for immunogenic cell death (ICD) (FIG. 19B).

When athymic mice bearing human NSCLC tumors (H292) were treated with scL-RB94, tumor growth was markedly inhibited (FIG. 18A). The H292 tumor-bearing mice began treatment at a tumor volume of 83.9±31.8 mm$^3$ and at the time of harvest, the untreated tumor volumes were 445.3±12.15 mm$^3$ while those harvested from the mice that had received the systemic SGT-94 treatment were 132.1±71.4 mm$^3$, demonstrating significant tumor inhibition (p-value<0.001). Similarly, untreated tumors weighed 0.2000±0.0044 g, while those from the SGT-94 treated mice were significantly (p<0.001) smaller weighing 0.05237±0.0146 g (FIG. 18B). Importantly, in all animal studies, the body weight of RB94 treated mice did not decrease, indicating that RB94 has minimal side effects, if any.

Example 16 scL-RB94 Induces Programmed Cell Death (PCD) in Tumor Cells

Following two injections of scL-RB94, mice bearing H358 induced tumors demonstrated significant DNA fragmentation, as demonstrated through the TUNEL Assay, an IHC apoptotic related assay (FIG. 19A).

Mice were euthanized and tumors were harvested after completion of treatment. When tumors were harvested, they were cut in half: one half was minced and frozen for RT-QPCR analysis, and the remaining half was fixed in 10% neutral buffered formalin. After 24 h, the formalin was exchanged with 70% ethanol. The fixed tumor sections were paraffin embedded, sectioned into 5 μm slices, and stained for IHC. The TUNEL staining was performed with ApopTag peroxidase in situ apoptosis detection kit (Millipore, S7200) according to the manufacture's protocol. Tumor sections were stained for Active Caspase-3 (Cell Signaling Technology, 9661), HMGB 1, CRT, iNOS, or Arg-1. Images were taken using the Olympus DP70 on the Olympus BX61 microscope. The percentage of positive cells was counted using ImageJ, (https://imagej.nih.gov/ij/download.html). At least 8 representative images from 4 tumors were used to quantify the IHC results.

There was a significant increase in positively stained cells in the tumors from the mice systemically treated with scL-RB94 (FIG. 19A). Only 8.12±11.27% of cells were positively stained in the untreated tumors. In contrast, 70.8±3.5% of cells in the tumors from the scl-RB94 treated mice demonstrated positive staining (p-value<0.001).

However, there was no differential in the active caspase-3 staining. Based upon what is known in the literature these results are surprising. Thus, the IHC results appear to indicate that apoptosis is not the cell autonomous pathway causing the differential in tumor volume and weight exhibited in these tumors (shown above in Example 15). Additionally, unexpectedly, DNA fragmentation appears to be occurring independently of and/or prior to apoptosis and the caspase cascade.

Example 17 scL-RB94 Treatment Upregulates Immunogenic Cell Death

Apoptotic tumor cell death can sometimes be immunogenic in that the tumor cell death can stimulate an otherwise dysfunctional immune system through exposure of damage associated molecular patterns (DAMPs) in the tumor microenvironment (TME) (Grant 30, 31). This phenomenon is referred to as immunogenic cell death (ICD) or immunogenic apoptosis and is therapeutically desirable since it stimulates immune responses against the tumor. One of the molecular hallmarks of ICD is the exodus of high-mobility group box 1 protein (HMGB 1) from dying cells. When H358 NSCLC tumors from mice treated with scL-RB94 were examined for HMGB 1 release by immunohistochemistry (IHC), HMGB 1 staining was highly elevated (FIG. 19B). In the untreated tumors 32.6±13.0% of the cells were positively stained, compared to 74.4±23.0% positive staining in the tumors from the mice treated with scL-RB94 (p-value<0.001). Surprisingly, this in vivo data demonstrates that scL-RB94 clearly upregulates the presence of HMGB 1 on the cell surface, confirming that RB94 expression resulting from scL-RB94 treatment induces ICD.

Example 18 scL-RB94 Alters the Presence Infiltrating Immune Cells in the Tumor

The unexpected observation that scL-RB94 treatment triggers ICD in NSCLC tumors suggests that this nanomedicine might be useful in enhancing immunotherapy for cancer, in one embodiment lung cancer. To explore this possibility, the expression of a number of immune-relevant genes involved in innate immune responses were assessed. In innate immunity, host cells involved in eliminating tumor cells are natural killer (NK) cells that surveil for the changes in a cell's features that define "self." Dendritic cells and macrophages are participants in innate immunity that are involved in the presentation of neoantigens exposed by ICD.

NSCLC H258 and H292 xenograft tumors were induced as described in EXAMPLE 15. Athymic mice lack T cells. FACS analysis was used to determine if treatment with scL-RB94 had an effect on infiltration of NK and dendritic cells. The mice received 6 intravenous injections of scL-RB94 (30 ug of plasmid DNA per injection) prior to harvesting the tumor and analyzing via FACS. Tumors were harvested, weighed, and cells were dissociated with Miltyni Biotec's Tumor Dissociation Kit (Cat. #130-096-730). Cells from in vivo samples were stained for viability with Zombie NIR (Biolegend, Cat #423105) and then were incubated in FC Block (BD Biosciences, 553142). Cells were stained with antibodies against NK1.1 (108736, BioLegend) and Zombie NIR, CD45+, CD11c+, MHCII+(I-A/I-E+), CD86+ for dendritic cells. Cells were analyzed by LSRFortessa flow cytometer (BD Biosciences).

Figure 20B:
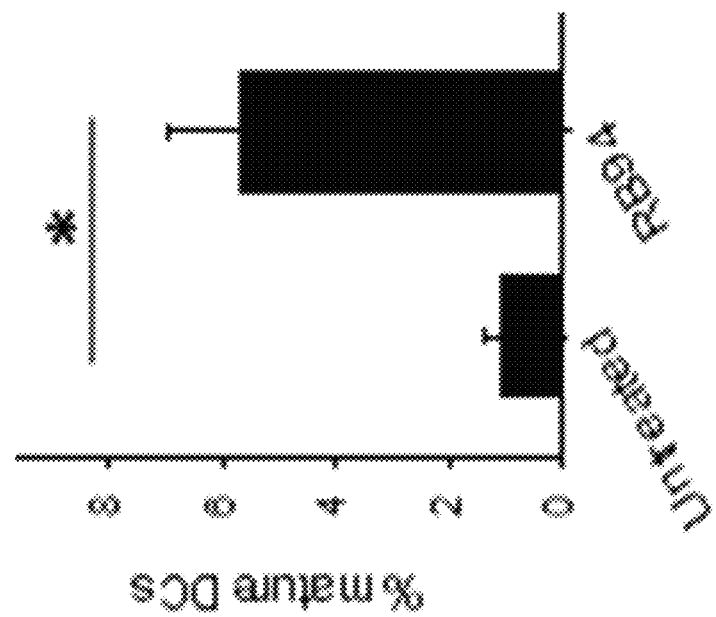
FIG. 20A-20C: Treatment with scL-RB94 increases expression of a number of immune-relevant genes involved in innate immune responses.
Figure 20A:
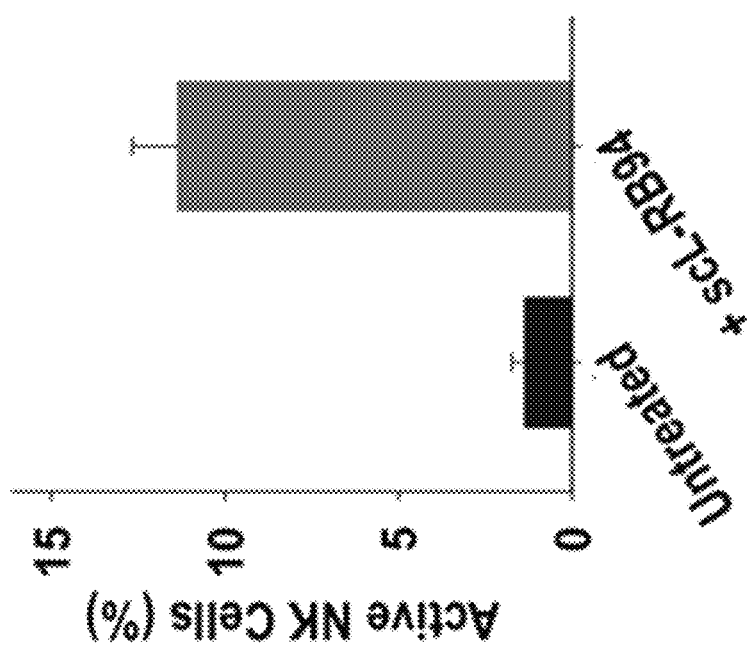
Figure 21:
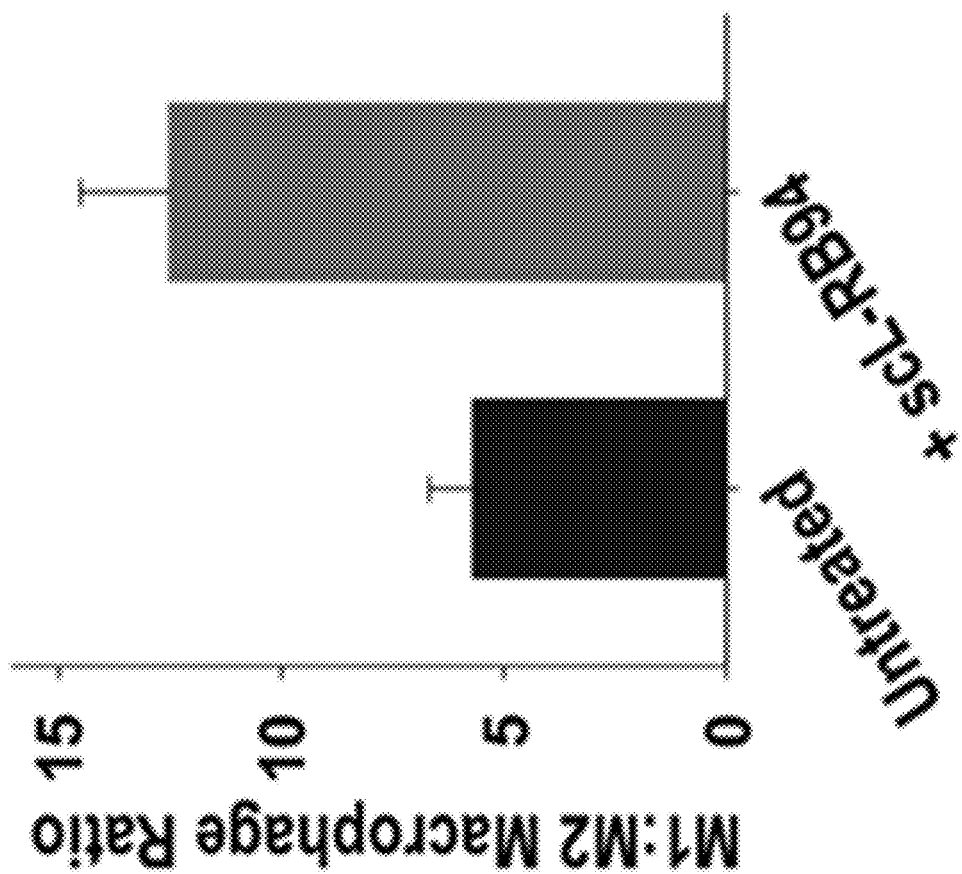
FIG. 21: scL-RB94 increases the ratio of M1 to M2 macrophages associated with H358 NSCLC tumors. Athymic mice bearing these tumors were treated with 6 doses of scL-RB94 (30 ug of plasmid DNA per injection) prior to harvesting the tumor and analyzing via FACS using markers for the M1 and M2 phenotypes of macrophages.

Treatment with scL-RB94 resulted in a significant increase in NSCLC H358 xenograft infiltration by activated mouse NK cells (FIG. 20A) and mature dendritic cells (FIG. 20B).

Figure 20C:
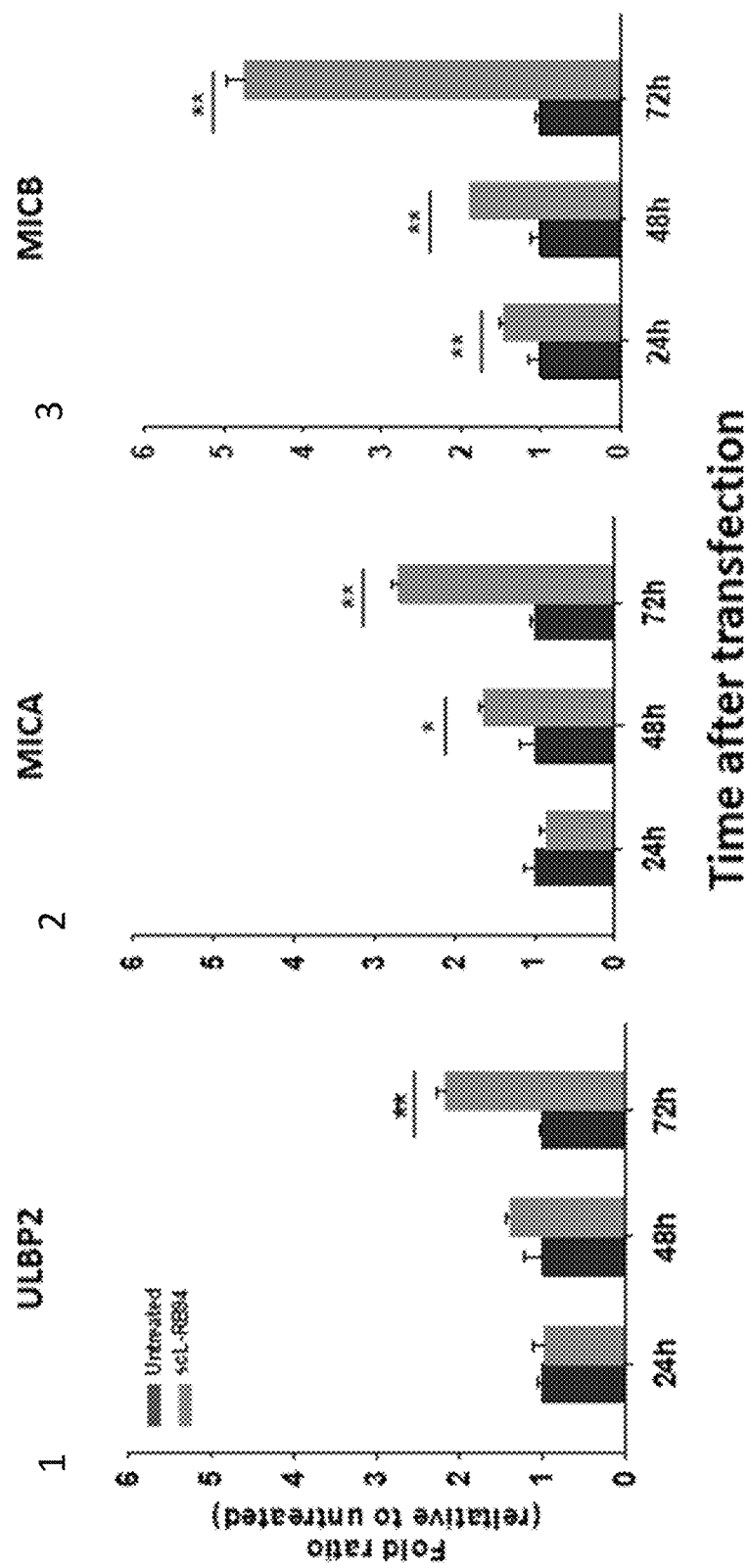

Changes in other transcription factors after in vitro treatment of H292 cells were assessed using RT PCR. RNA was extracted from cell pellets (or approximately 20 mg of tumor tissue for in vivo studies) using PureLink RNA Mini Kit (Ambion, 12183018A), according to the manufacture's protocol, 0.5 ug of extracted RNA was reverse transcribed in a 20 ul reaction volume with 5x iScript Reaction Mix and iScript Reverse Transcriptase (Bio-Rad, 1708891) following the manufacture's protocol. The RT-PCR was performed using BioRad's iTaq Universal Probes Supermix (Cat. 172-5134) and TaqMan gene expression assays (Life Technologies) for ULBP2 (Hs00607609_mH), MICA (Hs00792195__ml), MICB (Hs00792952 ml) and GAPDH (Hs02786624_gl). BioRad PrimePCR Probe Assays were used. The assay was run on the StepOnePlus RT-PCR system (Life Technologies) and the relative mRNA expression was analyzed using StepOne Software v2.3. The $\Delta\Delta C$ method was used to analyze the samples, which were normalized to the respective sample's value for GAPDH. Each sample was run at least in triplicate. These results demonstrate that scL-RB94 treatment of NSCLC cells in vitro also unexpectedly results in time-dependent upregulation in the expression of the NK cell-activation ligands (ULBP2, MICA and MICB (FIG. 20C).

Example 19 scL-RB94 Alters the Ratio of Anti-Tumoral Macrophage to Pro-Tumoral Macrophages in the Tumor Another important component of the innate immune response is the macrophage, which is able to adapt an anti-tumoral (M1) or pro-tumoral (M2) phenotype. In H358 tumors that received 6 intravenous administrations of scL-RB94, FACS analysis (as described above) revealed that levels of M1 (anti-tumoral) macrophages were the same between the treated and untreated tumors, however, the percentage of M2 macrophages decreased significantly. These results led to an unexpected, significant increase in the M1 to M2 ratio (FIG. 21). This suggests that scL-RB94 treatment results in a decrease in the presence of pro-tumor M2 macrophages. As M2 macrophages secrete cytokines and chemokines that suppress the immunogenicity of the tumor, a decrease in this phenotype of macrophage allows for the infiltration of pro-inflammatory immune cells, greatly altering the tumor microenvironment. Therefore, treatment with scL-RB94 also decreased tumor immune evasion by unexpectedly shifting the polarization of tumor-associated macrophages from tumor-promoting M2 macrophages to tumor-inhibiting M1 macrophages.

Example 20 scL-RB94 Upregulates Immune Recognition Molecules

A pathway critical to the relationship between the tumor and the host immune defense mechanisms are the antigen presentation molecules. To further elucidate if scL-RB94 increases the "visibility" of the tumor by upregulating the immune recognition molecules associated with the tumor, the major histocompatibility complex (MHC) class I pathway was analyzed in vitro.

H358 and H292 cells were transfected with scL-RB94. After 24 h, 48 h, and 72 h the cells were harvested and RT-PCR was performed to elucidate the transcription of molecules involved in the antigen presentation pathway (FIG. 22). RNA was extracted from the cell pellets using PureLink RNA Mini Kit (Ambion, 12183018A), according to the manufacture's protocol. 0.5 ug of extracted RNA was reverse transcribed in a 20 ul reaction volume with 5x iScript Reaction Mix and iScript Reverse Transcriptase (Bio-Rad, 1708891) following the manufacture's protocol. The RT-PCR was performed using BioRad's iTaq Universal Probes Supermix (Cat. 172-5134) and TaqMan gene expression assays (Life Technologies) for HLA-A (qHsaCEP0040111), TAP1 (qHsaCEP0039851), and TAP2 (qHsaCEP0040018).

In the H358 model (FIG. 22A), scL-RB94 transfection increased HLA-A transcription (relative to the untreated) over 24 h, 48 h, and 72 h by 1.19±0.01, 2.28±0.30, and 2.16±0.30-fold, respectively. Similarly, TAP1 increased by 3.86±0.20, 7.71±1.21, and 6.01±0.90-fold and TAP2 increased 1.27±0.04, 2.48±0.51, and 2.00±0.39-fold at 24 h, 48 h, and 72 h, respectively. The upregulation in the H292 cells in culture was even more significant (FIG. 22B). The transfection with scL-RB94 increased HLA-A transcription by 7.44±2.27, 17.23±0.89, 37.12±0.04-fold over 24 h, 48 h, and 72 h, respectively. Likewise, TAP1 increased by 5.35±0.94, 6.19±0.43, and 11.21±0.97-fold and TAP2 increased 2.20±0.10, 1.89±0.06, and 5.92±0.06-fold at 24 h, 48 h, and 72 h, respectively.

Therefore, here also unexpected expression of genes whose products are involved in antigen presentation (HLA-A) and antigen processing (TAP1 and TAP2) were also found to be upregulated after scL-RB94 treatment based on this RT-PCR analyses (FIG. 22).

Example 21 scL-RB94 Upregulates PD-L1

Figures 23A, 23B:
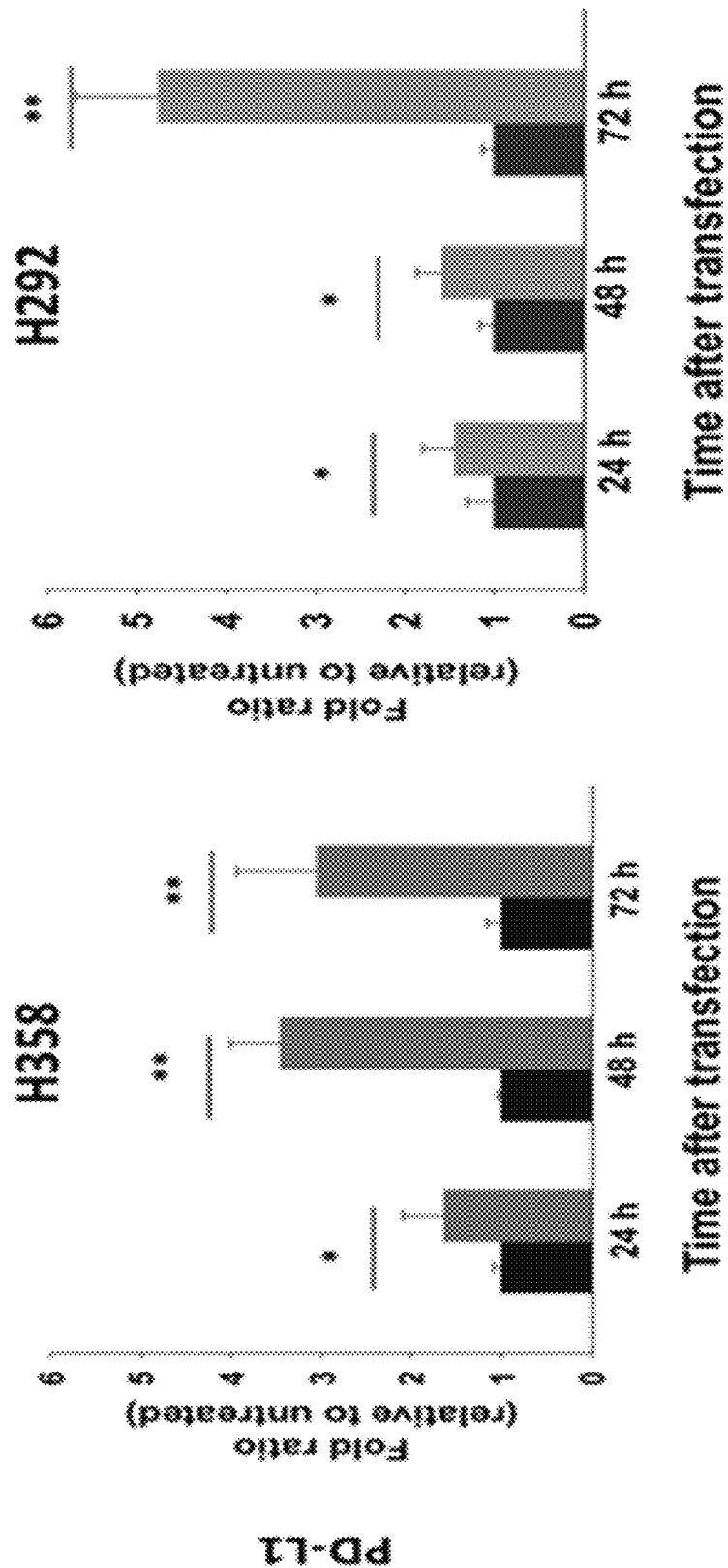
FIG. 23A-23B: Human NSCLC cell lines H358 (FIG. 23A) and H292 (FIG. 23B) were transfected with scL-RB94 and harvested at 24 h, 48 h, and 72 h. The transcription levels of PD-L1 mRNA was assessed by RT-PCR. Each sample was repeated in triplicate. *p<0.05, **p<0.001.

Another important class of molecules involved in the activation of the host cytotoxic T cells (CTL), is that of the co-stimulatory molecules. PD-L1, an inhibitory co-stimulatory molecule, is a crucial biomarker for what is currently considered to be one of the most effective immunotherapies. Increases in levels of this co-stimulatory molecule correlate to a positive response to the anti-PD 1 immunotherapy. NSCLC cells were transfected with scL-RB-94. After 24 h, 48 h, and 72 h the cells were harvested and RT-PCR was performed. RNA was extracted from the cell pellets using PureLink RNA Mini Kit (Ambion, 12183018A), according to the manufacture's protocol. 0.5 ug of extracted RNA was reverse transcribed in a 20 ul reaction volume with 5x iScript Reaction Mix and iScript Reverse Transcriptase (Bio-Rad, 1708891) following the manufacture's protocol. The RT-PCR was performed using BioRad's iTaq Universal Probes Supermix (Cat. 172-5134) and TaqMan gene expression assays (Life Technologies) for GAPDH (Hs02786624 gl) and CD274 (Hs01125301__ml). After transfection with scL-RB94, both H358 and H292 cells demonstrated a time-dependent increase in the transcription of PD-L1 (FIG. 23). In response to scL-RB94, the transcription of PD-L1 in H358 cells increased 1.62±0.19, 3.25±0.10, 3.34±0.18-fold at 24 h, 48 h, and 72 h, respectively (FIG. 23A). In H292 cells, the increase relative to the untreated cells was 1.45±0.04, 1.57±0.01, 3.99±0.36-fold at 24 h, 48 h, and 72 h, respectively (FIG. 23B). Here again there was an unexpected effect of scL-RB94 on immune stimulatory molecules.

Taken together the data presented in this application indicate that both innate and adaptive immunity against human NSCLC tumors is enhanced by administration of scL-94 with the resulting expression of RB94 in these tumors after tumor-targeted delivery of a plasmid carrying a gene encoding this protein.

Example 22

Use of the Combination of SGT-94 with Checkpoint Inhibitors and Chemotherapy for the Treatment of Cancer The unexpected observation that scL-RB94 treatment triggers ICD in NSCLC tumors suggests that this tumor suppressor nanomedicine also might be useful in enhancing immunotherapy for cancer, in one embodiment lung cancer, in a second embodiment genitourinary cancer.

The present invention provides methods for overcoming the current limitations of immune checkpoint immunotherapy to provide more effective methods of treating cancer by inducing/enhancing an immune response in humans comprising administering to the patient a ligand-targeted cationic liposome complex comprising a nucleic acid molecules encoding a tumor suppressor gene. This tumor suppressor gene can be either p53 or RB94. The complexes comprising a targeting ligand directly complexed/associated with, but not chemically conjugated to, the surface of the liposomes is prepared essentially as described above in Example 1 as follows:

The liposomes [Lipid A (DOTAP:DOPE, 1:1 molar ratio)] are prepared by the ethanol injection method modified from that described by Campbell, MJ (Biotechniques 1995 June; 18(6):1027-32). In brief, all lipids are solubilized in ethanol and mixed, injected into vortexing pure water of 50-60° C. with a Hamilton syringe. The solution is vortexed for a further 10-15 min. No further processing is required or employed. The final concentration is 1-2 mM total lipids.

The TfRscFv or any antibody or antibody fragment (including any scfv, Fab' or Mab)-immunoliposome complexes are prepared by mixing the TfRscFv with liposome composition (or any of the liposome compositions given above) at defined ratios of single chain protein to liposome and DNA in the mixed complex. The preparation of the complexes is in accordance with the following general procedure. The appropriate amount of 2 mM liposome is mixed with any water (e.g., DI water) required to give a desired volume and gently inverted 10 times to mix, or for larger volumes rotated at 20-30 RPM for 1-2 minutes. To the liposome-water mixture, the appropriate amount of TfRscFv is added to give the desired ratio and mixed by gentle inversion for about 5-10 seconds or for larger volumes rotated at 20-30 RPM for 1 minute. This mixture is kept at room temperature for 10-15 minutes (again inverted gently for 5-10 seconds after approximately 5 minutes). At the same time, the appropriate amount of DNA is mixed by inversion for 5-10 seconds, or for larger volumes rotated at 20-30 RPM for 1-2 minutes, with any water required to give a desired volume. Typically, for use in humans it is desirable to provide about 0.6 mg to about 10 mg of DNA per injection. The DNA solution is quickly added to the TfRscFv-liposome solution and the mixture is inverted for 5-10 seconds or for larger volumes rotated at 20-30 RPM for 1-2 minutes. The final mixture is kept at room temperature for 10-15 minutes, gently inverting again for 5-10 seconds after approximately 5 minutes. For use 50% sucrose or dextrose is added to a final concentration of 5-20% (V:V) and mixed by gentle inversion for 5-10 seconds, or for larger volumes rotated at 20-30 RPM for 1-2 minutes. No further manipulation (e.g. milling, extrusion) is required or takes place.

SGT-94, the nanocomplex encapsulating a plasmid DNA encoding the RB94 gene, is prepared as follows: The cationic liposome consisting of 1,2-dioleoyl-3-trimethylammonium propane (DOTAP) and dioleolylphosphatidyl ethanolamine (DOPE), referred to as Lip, is prepared using the ethanol injection method as detailed above. TfRscFv/Lip/Rb94 (SGT-94, scL encapsulating plasmid DNA encoding human RB-94 gene) complex is prepared by simple mixing of Lip with TfRscFv and plasmid DNA. The ligand (TfRscFv) is mixed with the liposome by inversion or gentle stirring at 25-30 RPM for 1 minute at room temperature and at a ligand:liposome ratio in the range of about 1:0.001 to 1:500 (ug:nmole), preferably about 1:10 to about 1:50 (ug:nmole). With TfRscFv as the ligand, useful ratios of ligand to liposome typically are within the range of about 1:5 to 1:40 (ug:ug), preferably 1:30 (ug:ug). The mixture is held at room temperature for 10-15 minutes. The pSCMV-94 plasmid DNA is then mixed with the immunoliposome at room temperature and at an plasmid:lipid ratio in the range of about 1:01 to about 1:50 (ug:nmole), preferably about 1:10 to about 1:24 (ug:nmole) or the ratio of plasmid DNA to liposome is typically within the range of about 1:6 to 1:20 (ug:ug), preferably 1:10 (ug:ug). To form the final SGT-53 complex, the plasmid is mixed with the Ligand:liposome by inversion or gentle stirring at 25-30 RPM for 1 minute at room temperature. The mixture is held at room temperature for 10-15 minutes, after which sucrose or dextrose, at a final concentration of 5-10%, is added to the SGT-53 preparation. The SGT-53 can be used immediately after preparation or lyophilized to dryness and stored at −20 to 8° C. and stored prior to use. If lyophilized, SGT-94 is reconstituted by the addition of sterile, endotoxin free water. After swirling for 30 sec to 1 min to dissolve. The vial may be used directly or is sonicated in a bath sonicator at 37 kHz, 100% power for 1 to 10 minutes at 31-34° C. for 1 to 10 minutes. The vial is swirled gently every 30-60 sec during the sonication.

The size (number average) of the final complex prepared by this method is between about 10 to 800 nm, suitably about 20 to 400 nm, most suitably about 25 to 200 nm with a zeta potential of between about 1 and 100 mV, more suitably 10 to 60 mV and most suitably 25 to 50 mV as determined by dynamic light scattering using a Malvern Zetasizer ZS. This size is small enough to efficiently pass through the capillary bed and reach the target tumor cells.

The complex, prepared as above, is used as a single agent or in combination with a checkpoint inhibitor. This checkpoint inhibitor is pembrolizumab (Keytruda) or nivolumab (Opdivo).

To treat patients with lung cancer, after diagnosis and assessment of tumor size by CT or MR, patients are treated with SGT-94 alone or in combination with the checkpoint inhibitor.

The total amount of RB94 DNA in the complex is 0.01 to 10 mg/kg/injection. A suitable amount is 0.164 mg/kg/injection which is 7-12 mg DNA/Injection, based upon the weight of the subject. A further suitable amount is 0.6 to 7.2 mg/injection independent of body weight. The prepared complex is injected either into a 250 ml 5% Dextrose bag for i.v. infusion, or injected i.v. as a bolus by intravenous (IV), intratumoral (IT), intralesional (IL), aerosol, percutaneous, oral, endoscopic, topical, intramuscular (IM), intradermal (ID), intraocular (IO), intraperitoneal (IP), transdermal (TD), intranasal (IN), intracereberal (IC), intraorgan (e.g. intrahepatic), slow release implant, or subcutaneous administration, or via administration using an osmotic or mechanical pump.

SGT-94 is administered once or twice weekly at a preferred dose of 3.6 mg DNA/infusion. Doses of 2.4 or 7.2 mg/infusion are also used. The checkpoint inhibitor is administered at the standard FDA approved dose which for pembrolizumab is 200 mg/injection. A chemotherapeutic agent can also be administered in combination with SGT-94 and the checkpoint inhibitor. Examples of such chemotherapeutic agents in the treatment of lung cancer are cisplatin (Platinol) or carboplatin (Paraplatin) plus docetaxel (Taxotere), gemcitabine (Gemzar), paclitaxel (Taxol and others), vinorelbine (Navelbine and others), or pemetrexed (Alimita). These chemotherapeutic agents are administered at the standard FDA approved doses. An example of the schedule of administration of SGT-94, pembrolizumab and carboplatin is shown in the table below.

| Agent | Dose | Route | Schedule | Cycle Length |
|---|---|---|---|---|
| SGT-94 | 3.6 mg | IV over 2 hours | Days 1 (±1-2 days), 8 (±1-2 days), and 15 (±1-2 days) of each cycle | 21 days |
| Pembrolizumab | 200 mg | IV over 30 min | Day 3 (2 days post-SGT-53) of each cycle | |
| Carboplatin | AUC 5 | IV infusion | Day 3 (2 days post-SGT-53) of each 3 week cycle | |

One cycle lasts 21 days. Multiple cycles are administered.

In a similar way a combination of SGT-94, checkpoint inhibitor and FDA approved chemotherapeutic agents (e.g. cisplatin) is used to treat genitourinary cancer. The same dose of SGT-94 and checkpoint inhibitor are used. The standard dose of the chemotherapeutic agent is used. As one example cisplatin is used to treat bladder cancer, one type of genitourinary cancer.

REFERENCES

1. Mellman I, Coukos G, Dranoff G. Cancer immunotherapy comes of age. Nature. 2011; 480(7378):480-9. Epub 2011/12/24. doi: 10.1038/nature10673. PubMed PMID: 22193102; PubMed Central PMCID: PMC3967235.
2. Kim E S, Kim J E, Patel M A, Mangraviti A, Ruzevick J, Lim M. Immune Checkpoint Modulators: An Emerging Antiglioma Armamentarium. Journal of immunology research. 2016; 2016:4683607. Epub 2016/02/18. doi: 10.1155/2016/4683607. PubMed PMID: 26881264; PubMed Central PMCID: PMC4736366.
3. Pardoll D M. The blockade of immune checkpoints in cancer immunotherapy. Nature reviews Cancer. 2012; 12(4):252-64. Epub 2012/03/23. doi: 10.1038/nrc3239. PubMed PMID: 22437870; PubMed Central PMCID: PMC4856023.
4. Zou W, Wolchok J D, Chen L. PD-L1 (B7-H1) and PD-1 pathway blockade for cancer therapy: Mechanisms, response biomarkers, and combinations. Science translational medicine. 2016; 8(328):328rv4. Epub 2016/03/05. doi: 10.1126/scitranslmed.aad7118. PubMed PMID: 26936508; PubMed Central PMCID: PMC4859220.
5. O'Donnell J S, Smyth M J, Teng M W. Acquired resistance to anti-PD1 therapy: checkmate to checkpoint blockade? Genome medicine. 2016; 8(1):111. Epub 2016/10/27. doi: 10.1186/s 13073-016-0365-1. PubMed PMID: 27782862; PubMed Central PMCID: PMC5080691.
6. Ribas A, Hu-Lieskovan S. What does PD-L1 positive or negative mean? The Journal of experimental medicine. 2016; 213(13):2835-40. Epub 2016/12/03. doi: 10.1084/jem.20161462. PubMed PMID: 27903604; PubMed Central PMCID: PMC5154949.
7. Ke X, Zhang S, Xu J, Liu G, Zhang L, Xie E, et al. Non-small-cell lung cancer-induced immunosuppression by increased human regulatory T cells via Foxp3 promoter demethylation. Cancer immunology, immunotherapy: CII. 2016; 65(5):587-99. Epub 2016/03/24. doi: 10.1007/s00262-016-1825-6. PubMed PMID: 27000869.
8. Dempke WCM, Fenchel K, Dale S P. Programmed cell death ligand-1 (PD-L1) as a biomarker for non-small cell lung cancer (NSCLC) treatment—are we barking up the wrong tree? Translational lung cancer research. 2018; 7(Suppl 3):S275-S9. Epub 2018/11/06. doi: 10.21037/tlcr.2018.04.18. PubMed PMID: 30393621; PubMed Central PMCID: PMC6193918.
9. Herbst R S, Baas P, Kim D W, Felip E, Perez-Gracia J L, Han J Y, et al. Pembrolizumab versus docetaxel for previously treated, PD-L1-positive, advanced non-small-cell lung cancer (KEYNOTE-010): a randomised controlled trial. Lancet. 2016; 387(10027):1540-50. Epub 2015/12/30. doi: 10.1016/S0140-6736(15)01281-7. PubMed PMID: 26712084.
10. Hassel J C, Heinzerling L, Aberle J, Bahr O, Eigentler T K, Grimm M O, et al. Combined immune checkpoint blockade (anti-PD-1/anti-CTLA-4): Evaluation and management of adverse drug reactions. Cancer treatment reviews. 2017; 57:36-49. Epub 2017/05/28. doi: 10.1016/j.ctrv.2017.05.003. PubMed PMID: 28550712.
11. Lechner M G, Karimi S S, Barry-Holson K, Angell T E, Murphy K A, Church C H, et al. Immunogenicity of murine solid tumor models as a defining feature of in vivo behavior and response to immunotherapy. J Immunother. 2013; 36(9):477-89. Epub 2013/10/23. doi: 10.1097/01.cji.0000436722.46675.4a. PubMed PMID: 24145359; PubMed Central PMCID: PMC3910494.

12. Ott P A, Hodi F S, Kaufman H L, Wigginton J M, Wolchok J D. Combination immunotherapy: a road map. Journal for immunotherapy of cancer. 2017; 5:16. Epub 2017/02/28. doi: 10.1186/s40425-017-0218-5. PubMed PMID: 28239469; PubMed Central PMCID: PMC5319100.
13. Mahoney K M, Rennert P D, Freeman G J. Combination cancer immunotherapy and new immunomodulatory targets. Nature reviews Drug discovery. 2015; 14(8):561-84. Epub 2015/08/01. doi: 10.1038/nrd4591. PubMed PMID: 26228759.
14. Chen D S, Mellman I. Elements of cancer immunity and the cancer-immune set point. Nature. 2017; 541(7637): 321-30. Epub 2017/01/20. doi: 10.1038/nature21349. PubMed PMID: 28102259.
15. Soussi T, Wiman K G. Shaping genetic alterations in human cancer: the p53 mutation paradigm. Cancer cell. 2007; 12(4):303-12. Epub 2007/10/16. doi: 10.1016/j.ccr.2007.10.001. PubMed PMID: 17936556.
16. El-Deiry W S. Insights into cancer therapeutic design based on p53 and TRAIL receptor signaling. Cell death and differentiation. 2001; 8(11):1066-75. Epub 2001/11/01. doi: 10.1038/sj.cdd.4400943. PubMed PMID: 11687885.
17. Mello S S, Attardi L D. Deciphering p53 signaling in tumor suppression. Current opinion in cell biology. 2017; 51:65-72. Epub 2017/12/02. doi: 10.1016/j.ceb.2017.11.005. PubMed PMID: 29195118.
18. Valente J F, Queiroz J A, Sousa F. p53 as the focus of gene therapy: past, present and future. Current drug targets. 2018. Epub 2018/01/18. doi: 10.2174/1389450119666180115165447. PubMed PMID: 29336259.
19. Yu X, Vazquez A, Levine A J, Carpizo D R. Allele-specific p53 mutant reactivation. Cancer cell. 2012; 21(5): 614-25. Epub 2012/05/26. doi: 10.1016/j.ccr.2012.03.042. PubMed PMID: 22624712; PubMed Central PMCID: PMC3366694.
20. Menendez D, Shatz M, Resnick M A. Interactions between the tumor suppressor p53 and immune responses. Current opinion in oncology. 2013; 25(1):85-92. Epub 2012/11/15. doi: 10.1097/CCO.0b013e32835b6386. PubMed PMID: 23150340.
21. Cui Y, Guo G. Immunomodulatory Function of the Tumor Suppressor p53 in Host Immune Response and the Tumor Microenvironment. International journal of molecular sciences. 2016; 17(11). Epub 2016/11/22. doi: 10.3390/ijms17111942. PubMed PMID: 27869779; PubMed Central PMCID: PMC5133937.
22. Li D, Day K V, Yu S, Shi G, Liu S, Guo M, et al. The role of adenovirus-mediated retinoblastoma 94 in the treatment of head and neck cancer. Cancer research. 2002; 62(16):4637-44. Epub 2002/08/17. PubMed PMID: 12183420.
23. Zhang X, Multani A S, Zhou J H, Shay J W, McConkey D, Dong L, et al. Adenoviral-mediated retinoblastoma 94 produces rapid telomere erosion, chromosomal crisis, and caspase-dependent apoptosis in bladder cancer and immortalized human urothelial cells but not in normal urothelial cells. Cancer research. 2003; 63(4):760-5. Epub 2003/02/20. PubMed PMID: 12591722.
24. Zeng J, See A P, Phallen J, Jackson C M, Belcaid Z, Ruzevick J, et al. Anti-PD-1 blockade and stereotactic radiation produce long-term survival in mice with intracranial gliomas. International journal of radiation oncology, biology, physics. 2013; 86(2):343-9. Epub 2013/03/07. doi: 10.1016/j.ijrobp.2012.12.025. PubMed PMID: 23462419; PubMed Central PMCID: PMC3963403.
25. Buerki R A, Chheda Z S, Okada H. Immunotherapy of Primary Brain Tumors: Facts and Hopes. Clinical cancer research: an official journal of the American Association for Cancer Research. 2018; 24(21):5198-205. Epub 2018/06/07. doi: 10.1158/1078-0432.CCR-17-2769. PubMed PMID: 29871908; PubMed Central PMCID: PMC6214775.
26. Kim S S, Rait A, Rubab F, Rao A K, Kiritsy M C, Pirollo K F, et al. The clinical potential of targeted nanomedicine: delivering to cancer stem-like cells. Molecular therapy: the journal of the American Society of Gene Therapy. 2014; 22(2):278-91. Epub 2013/10/12. doi: 10.1038/mt.2013.231. PubMed PMID: 24113515; PubMed Central PMCID: PMC3916038.
27. Kim S S, Harford J B, Moghe M, Rait A, Chang E H. Combination with SGT-53 overcomes tumor resistance to a checkpoint inhibitor. Oncoimmunology. 2018; 7(10): e1484982. Epub 2018/10/06. doi: 10.1080/2162402X.2018.1484982. PubMed PMID: 30288347; PubMed Central PMCID: PMC6169574.
28. Syn N L, Teng M W L, Mok T S K, Soo R A. De-novo and acquired resistance to immune checkpoint targeting. The Lancet Oncology. 2017; 18(12):e731-e41. Epub 2017/12/07. doi: 10.1016/S1470-2045(17)30607-1. PubMed PMID: 29208439.
29. Gameiro S R, Jammeh M L, Wattenberg M M, Tsang K Y, Ferrone S, Hodge J W. Radiation-induced immunogenic modulation of tumor enhances antigen processing and calreticulin exposure, resulting in enhanced T-cell killing. Oncotarget. 2014; 5(2):403-16. Epub 2014/02/01. doi: 10.18632/oncotarget.1719. PubMed PMID: 24480782; PubMed Central PMCID: PMC3964216.
30. Zhu K, Wang J, Zhu J, Jiang J, Shou J, Chen X. p53 induces TAP1 and enhances the transport of MHC class I peptides. Oncogene. 1999; 18(54):7740-7. Epub 2000/01/05. doi: 10.1038/sj.onc.1203235. PubMed PMID: 10618714.
31. Moore E C, Sun L, Clavijo P E, Friedman J, Harford J B, Saleh A D, et al. Nanocomplex-based TP53 gene therapy promotes anti-tumor immunity through TP53- and STING-dependent mechanisms. Oncoimmunology. 2018; 7(7):e1404216. Epub 2018/06/15. doi: 10.1080/2162402X.2017.1404216. PubMed PMID: 29900037; PubMed Central PMCID: PMC5993490.
32. Mall C, Sckisel G D, Proia D A, Mirsoian A, Grossenbacher S K, Pai C S, et al. Repeated PD-1/PD-L1 monoclonal antibody administration induces fatal xenogeneic hypersensitivity reactions in a murine model of breast cancer. Oncoimmunology. 2016; 5(2):e1075114. Epub 2016/04/09. doi: 10.1080/2162402X.2015.1075114. PubMed PMID: 27057446; PubMed Central PMCID: PMC4801432.
33. McGuire H M, Shklovskaya E, Edwards J, Trevillian P R, McCaughan G W, Bertolino P, et al. Anti-PD-1-induced high-grade hepatitis associated with corticosteroid-resistant T cells: a case report. Cancer immunology, immunotherapy: CII. 2018; 67(4):563-73. Epub 2018/01/01. doi: 10.1007/s00262-017-2107-7. PubMed PMID: 29289977; PubMed Central PMCID: PMC5860100.
34. Kudlak K, Demuro J P, Hanna A F, Brem H. Acute lung injury following the use of granulocyte-macrophage colony-stimulating factor. International journal of critical illness and injury science. 2013; 3(4):279-81. Epub 2014/01/25. doi: 10.4103/2229-5151.124168. PubMed PMID: 24459628; PubMed Central PMCID: PMC3891197.

35. Descotes J. Immunotoxicity of monoclonal antibodies. mAbs. 2009; 1(2):104-11. Epub 2010/01/12. doi: 10.4161/mabs.1.2.7909. PubMed PMID: 20061816; PubMed Central PMCID: PMC2725414.

36. El-Deiry W S. The role of p53 in chemosensitivity and radiosensitivity. Oncogene. 2003; 22(47):7486-95. Epub 2003/10/25. doi: 10.1038/sj.onc. 1206949. PubMed PMID: 14576853.

37. Kim S S, Rait A, Kim E, Pirollo K F, Nishida M, Farkas N, et al. A nanoparticle carrying the p53 gene targets tumors including cancer stem cells, sensitizes glioblastoma to chemotherapy and improves survival. ACS nano. 2014; 8(6):5494-514. Epub 2014/05/09. doi: 10.1021/nn5014484. PubMed PMID: 24811110; PubMed Central PMCID: PMC4076028.

38. Kim S S, Rait A, Kim E, Pirollo K F, Chang E H. A tumor-targeting p53 nanodelivery system limits chemoresistance to temozolomide prolonging survival in a mouse model of glioblastoma multiforme. Nanomedicine: nanotechnology, biology, and medicine. 2015; 11(2): 301-11. Epub 2014/09/23. doi: 10.1016/j.nano.2014.09.005. PubMed PMID: 25240597; PubMed Central PMCID: PMC4330129.

39. Xu L, Pirollo K F, Tang W H, Rait A, Chang E H. Transferrin-liposome-mediated systemic p53 gene therapy in combination with radiation results in regression of human head and neck cancer xenografts. Human gene therapy. 1999; 10(18):2941-52. Epub 1999/12/28. doi: 10.1089/10430349950016357. PubMed PMID: 10609655.

40. Munoz-Fontela C, Mandinova A, Aaronson S A, Lee S W. Emerging roles of p53 and other tumour-suppressor genes in immune regulation. Nature reviews Immunology. 2016; 16(12):741-50. Epub 2016/11/01. doi: 10.1038/nri.2016.99. PubMed PMID: 27667712; PubMed Central PMCID: PMC5325695.

41. Guo G, Yu M, Xiao W, Celis E, Cui Y. Local Activation of p53 in the Tumor Microenvironment Overcomes Immune Suppression and Enhances Antitumor Immunity. Cancer research. 2017; 77(9):2292-305. Epub 2017/03/11. doi: 10.1158/0008-5472.CAN-16-2832. PubMed PMID: 28280037; PubMed Central PMCID: PMC5465961.

42. Pfirschke C, Engblom C, Rickelt S, Cortez-Retamozo V, Garris C, Pucci F, et al. Immunogenic Chemotherapy Sensitizes Tumors to Checkpoint Blockade Therapy. Immunity. 2016; 44(2):343-54. Epub 2016/02/14. doi: 10.1016/j.immuni.2015.11.024. PubMed PMID: 26872698; PubMed Central PMCID: PMC4758865.

43. Kaur P, Asea A. Radiation-induced effects and the immune system in cancer. Frontiers in oncology. 2012; 2:191. Epub 2012/12/20. doi: 10.3389/fonc.2012.00191. PubMed PMID: 23251903; PubMed Central PMCID: PMC3523399.

44. Zhou H, Forveille S, Sauvat A, Yamazaki T, Senovilla L, Ma Y, et al. The oncolytic peptide LTX-315 triggers immunogenic cell death. Cell death & disease. 2016; 7:e2134. Epub 2016/03/11. doi: 10.1038/cddis.2016.47. PubMed PMID: 26962684; PubMed Central PMCID: PMC4823948.

45. Moore E C, Sun L, Clavijo P E, Friedman J, Harford J B, Saleh A D, et al. Nanocomplex-based TP53 gene therapy promotes anti-tumor immunity through TP53- and STING-dependent mechanisms. Oncoimmunology. 2018. doi: https://doi.org/10.1080/2162402X.2017.1404216

46. Wang X, Schoenhals J E, Li A, Valdecanas D R, Ye H, Zang F, et al. Suppression of Type I IFN Signaling in Tumors Mediates Resistance to Anti-PD-1 Treatment That Can Be Overcome by Radiotherapy. Cancer research. 2017; 77(4):839-50. Epub 2016/11/09. doi: 10.1158/0008-5472.CAN-15-3142. PubMed PMID: 27821490.

47. Lettau M, Paulsen M, Schmidt H, Janssen O. Insights into the molecular regulation of FasL (CD178) biology. European journal of cell biology. 2011; 90(6-7):456-66. Epub 2010/12/04. doi: 10.1016/j.ejcb.2010.10.006. PubMed PMID: 21126798.

48. Braun M W, Iwakuma T. Regulation of cytotoxic T-cell responses by p53 in cancer. Translational cancer research. 2016; 5(6):692-7. Epub 2017/09/26. doi: 10.21037/tcr.2016.11.76. PubMed PMID: 28944167; PubMed Central PMCID: PMC5607642.

49. Wang B, Niu D, Lai L, Ren E C. p53 increases MHC class I expression by upregulating the endoplasmic reticulum aminopeptidase ERAP1. Nature communications. 2013; 4:2359. Epub 2013/08/24. doi: 10.1038/ncomms3359. PubMed PMID: 23965983; PubMed Central PMCID: PMC3759077.

50. Thiery J, Abouzahr S, Dorothee G, Jalil A, Richon C, Vergnon I, et al. p53 potentiation of tumor cell susceptibility to CTL involves Fas and mitochondrial pathways. J Immunol. 2005; 174(2):871-8. Epub 2005/01/07. PubMed PMID: 15634909.

51. Owen-Schaub L B, Zhang W, Cusack J C, Angelo L S, Santee S M, Fujiwara T, et al. Wild-type human p53 and a temperature-sensitive mutant induce Fas/APO-1 expression. Molecular and cellular biology. 1995; 15(6):3032-40. Epub 1995/06/01. PubMed PMID: 7539102; PubMed Central PMCID: PMC230534.

52. Meslin F, Thiery J, Richon C, Jalil A, Chouaib S. Granzyme B-induced cell death involves induction of p53 tumor suppressor gene and its activation in tumor target cells. The Journal of biological chemistry. 2007; 282(45): 32991-9. Epub 2007/09/15. doi: 10.1074/jbc.M705290200. PubMed PMID: 17855337.

53. Ben Safta T, Ziani L, Favre L, Lamendour L, Gros G, Mami-Chouaib F, et al. Granzyme B-activated p53 interacts with Bcl-2 to promote cytotoxic lymphocyte-mediated apoptosis. J Immunol. 2015; 194(1):418-28. Epub 2014/11/19. doi: 10.4049/jimmunol.1401978. PubMed PMID: 25404359.

54. Hirayama Y, Gi M, Yamano S, Tachibana H, Okuno T, Tamada S, et al. Anti-PD-L1 treatment enhances antitumor effect of everolimus in a mouse model of renal cell carcinoma. Cancer science. 2016; 107(12):1736-44. Epub 2016/10/07. doi: 10.1111/cas. 13099. PubMed PMID: 27712020; PubMed Central PMCID: PMC5198964.

55. Harter P N, Bernatz S, Scholz A, Zeiner P S, Zinke J, Kiyose M, et al. Distribution and prognostic relevance of tumor-infiltrating lymphocytes (TILs) and PD-1/PD-L1 immune checkpoints in human brain metastases. Oncotarget. 2015; 6(38):40836-49. Epub 2015/10/31. doi: 10.18632/oncotarget.5696. PubMed PMID: 26517811; PubMed Central PMCID: PMC4747372.

56. Fridman W H, Pages F, Sautes-Fridman C, Galon J. The immune contexture in human tumours: impact on clinical outcome. Nature reviews Cancer. 2012; 12(4):298-306. Epub 2012/03/16. doi: 10.1038/nrc3245. PubMed PMID: 22419253.

57. Holmgaard R B, Zamarin D, Li Y, Gasmi B, Munn D H, Allison J P, et al. Tumor-Expressed IDO Recruits and Activates MDSCs in a Treg-Dependent Manner. Cell reports. 2015; 13(2):412-24. Epub 2015/09/29. doi: 10.1016/j.celrep.2015.08.077. PubMed PMID: 26411680; PubMed Central PMCID: PMC5013825.
58. Prendergast G C, Malachowski W P, DuHadaway J B, Muller A J. Discovery of IDO1 Inhibitors: From Bench to Bedside. Cancer research. 2017; 77(24):6795-811. Epub 2017/12/17. doi: 10.1158/0008-5472.CAN-17-2285. PubMed PMID: 29247038.
59. Zaretsky J M, Garcia-Diaz A, Shin D S, Escuin-Ordinas H, Hugo W, Hu-Lieskovan S, et al. Mutations Associated with Acquired Resistance to PD-1 Blockade in Melanoma. The New England journal of medicine. 2016; 375(9):819-29. Epub 2016/07/20. doi: 10.1056/NEJMoa1604958. PubMed PMID: 27433843; PubMed Central PMCID: PMC5007206.
60. Taube J M, Klein A, Brahmer J R, Xu H, Pan X, Kim J H, et al. Association of PD-1, PD-1 ligands, and other features of the tumor immune microenvironment with response to anti-PD-1 therapy. Clinical cancer research: an official journal of the American Association for Cancer Research. 2014; 20(19):5064-74. Epub 2014/04/10. doi: 10.1158/1078-0432.CCR-13-3271. PubMed PMID: 24714771; PubMed Central PMCID: PMC4185001.
61. Garon E B, Rizvi N A, Hui R, Leighl N, Balmanoukian A S, Eder J P, et al. Pembrolizumab for the treatment of non-small-cell lung cancer. The New England journal of medicine. 2015; 372(21):2018-28. Epub 2015/04/22. doi: 10.1056/NEJMoa1501824. PubMed PMID: 25891174.
62. Daud A I, Wolchok J D, Robert C, Hwu W J, Weber J S, Ribas A, et al. Programmed Death-Ligand 1 Expression and Response to the Anti-Programmed Death 1 Antibody Pembrolizumab in Melanoma. Journal of clinical oncology: official journal of the American Society of Clinical Oncology. 2016; 34(34):4102-9. Epub 2016/11/20. doi: 10.1200/JCO.2016.67.2477. PubMed PMID: 27863197; PubMed Central PMCID: PMC5562434.
63. Jing W, Li M, Zhang Y, Teng F, Han A, Kong L, et al. PD-1/PD-L1 blockades in non-small-cell lung cancer therapy. OncoTargets and therapy. 2016; 9:489-502. Epub 2016/02/19. doi: 10.2147/OTT.S94993. PubMed PMID: 26889087; PubMed Central PMCID: PMC4741366.
64. Gangadhar T C, Vonderheide R H. Mitigating the toxic effects of anticancer immunotherapy. Nature reviews Clinical oncology. 2014; 11(2):91-9. Epub 2014/01/22. doi: 10.1038/nrclinonc.2013.245. PubMed PMID: 24445516.
65. Senzer N, Nemunaitis J, Nemunaitis D, Bedell C, Edelman G, Barve M, et al. Phase I study of a systemically delivered p53 nanoparticle in advanced solid tumors. Molecular therapy the journal of the American Society of Gene Therapy. 2013; 21(5):1096-103. Epub 2013/04/24. doi: 10.1038/mt.2013.32. PubMed PMID: 23609015.
66. Pirollo K F, Nemunaitis J, Leung P K, Nunan R, Adams J, Chang E H. Safety and efficacy in advanced solid tumors of a targeted nanocomplex carrying the p53 gene used in combination with docetaxel: a phase 1b study. Molecular therapy: the journal of the American Society of Gene Therapy. 2016; 24(9):1697-706. Epub 2016/07/01. doi: 10.1038/mt.2016.135. PubMed PMID: 27357628; PubMed Central PMCID: PMC5113104.
67. Willingham S B, Volkmer J P, Gentles A J, Sahoo D, Dalerba P, Mitra S S, et al. The CD47-signal regulatory protein alpha (SIRPa) interaction is a therapeutic target for human solid tumors. Proceedings of the National Academy of Sciences of the United States of America. 2012; 109(17):6662-7. Epub 2012/03/28. doi: 10.1073/pnas.1121623109. PubMed PMID: 22451913; PubMed Central PMCID: PMC3340046.
68. Sica A, Larghi P, Mancino A, Rubino L, Porta C, Totaro M G, et al. Macrophage polarization in tumour progression. Seminars in cancer biology. 2008; 18(5):349-55. Epub 2008/05/10. doi: 10.1016/j.semcancer.2008.03.004. PubMed PMID: 18467122.

It is to be understood that while certain embodiments have been illustrated and described herein, the claims are not to be limited to the specific forms or arrangement of parts described and shown. In the specification, there have been disclosed illustrative embodiments and, although specific terms are employed, they are used in a generic and descriptive sense only and not for purposes of limitation. Modifications and variations of the embodiments are possible in light of the above teachings. It is therefore to be understood that the embodiments may be practiced otherwise than as specifically described.

While various embodiments have been described above, it should be understood that they have been presented only as illustrations and examples of the present technology, and not by way of limitation. It will be apparent to persons skilled in the relevant art that various changes in form and detail can be made therein without departing from the spirit and scope of the present technology. Thus, the breadth and scope of the present technology should not be limited by any of the above-described embodiments, but should be defined only in accordance with the appended claims and their equivalents. It will also be understood that each feature of each embodiment discussed herein, and of each reference cited herein, can be used in combination with the features of any other embodiment. All patents and publications discussed herein are incorporated by reference herein in their entirety.

What is claimed is:

1. A method of treating a cancer in a patient, consisting of:
   a. providing a transferrin-receptor-targeted cationic liposomal complex, comprising:
      i. a cationic liposome;
      ii. an anti-transferrin receptor single chain Fv (TfRscFv) complexed with the cationic liposome, but not chemically conjugated to the cationic liposome, and wherein the TfRscFv does not comprise a lipid tag; and
      iii. a nucleic acid encoding p53;
   b. administering intravenously only the transferrin-receptor-targeted cationic liposomal complex in combination with an immune checkpoint modulator to the patient; and
   c. delivering the nucleic acid encoding p53 via the transferrin-receptor targeted cationic liposomal complex to immune cells in the patient and the immune checkpoint modulator to immune cells in the patient;
   d. enhancing an innate anti-tumor immune response triggered by the immune cells of the patient; and
   e. enhancing an adaptive immunity response triggered by the immune cells of the patient.

2. The method of claim 1, wherein the immune checkpoint modulator is an anti-PD1 (programmed cell death-1) antibody.

3. The method of claim 1, wherein the treatment also reduces a xenogeneic hypersensitivity reaction.

4. The method of claim 1, wherein the transferrin-receptor-targeted cationic liposomal complex is administered in combination with the immune checkpoint modulator and a chemotherapeutic agent and/or radiation therapy to the patient to treat the cancer, and wherein the chemotherapeutic agent is selected from the group consisting of cisplatin, carboplatin, docetaxel, gemcitabine, paclitaxel, vinorelbine, and pemetrexed.

5. The method of claim 1, wherein the immune checkpoint modulator is an inhibitor checkpoint modulator selected from the group consisting of adenosine A2A receptor (A2AR), B7-H3, B7-H4, B-and T-lymphocyte attenuator (BTLA), cytotoxic T lymphocyte antigen 4 (CTLA-4), Indoleamine 2,3-dioxygenase (IDO), Killer cell immunoglobulin-like receptors (KIR), Lymphocyte-activation gene 3 (LAG3), programmed cell death-1 (PD-1), programmed death-ligand 1 (PD-L1), programmed death-ligand 2 (PD-L2), T-cell immunoglobulin and mucin domain 3 (TIM-3), V-domain Ig suppressor of T cell activation (VISTA) (protein), TIGIT (T cell Ig and ITIM domain), CD47, and Signal regulatory protein alpha (SIRPalpha).

6. The method of claim 1, wherein the immune checkpoint modulator is a stimulatory check point molecule selected from the group consisting of CD27, CD28, CD40, CD122, CD137, OX40, glucocorticoid-induced tumor necrosis factor receptor-related protein (GITR), and inducible costimulator of T cells (ICOS).

7. The method of claim 1, wherein the cancer is a primary or metastatic brain tumor, a breast cancer, a neuroendocrine tumor, a melanoma, a pancreatic cancer, a prostate cancer, a head and neck cancer, an ovarian cancer, a lung cancer, a bladder cancer, a kidney cancer, a liver cancer, a vaginal cancer, a urogenital cancer, a gastric cancer, a colorectal cancer, a cervical cancer, a liposarcoma, an angiosarcoma, a rhabdomyosarcoma, a choriocarcinoma, a retinoblastoma, and a multiple myeloma.

8. The method of claim 7, wherein the breast cancer is a primary or metastatic breast cancer, an inflammatory breast cancer, a Ductal Carcinoma In Situ (DCIS), invasive ductal carcinoma (IDC) including IDC Type: Tubular Carcinoma of the Breast, IDC Type: Medullary Carcinoma of the Breast, IDC Type:

Mucinous Carcinoma of the Breast, IDC Type: Papillary Carcinoma of the Breast, IDC Type: Cribriform Carcinoma of the Breast, as well as Invasive Lobular Carcinoma (ILC), Lobular Carcinoma In Situ (LCIS), Male Breast Cancer, Molecular Subtypes of Breast Cancer, Paget's Disease of the Nipple, Phyllodes Tumors of the Breast, and Metastatic Breast Cancer.

9. The method of claim 7, wherein the breast cancer is an inflammatory breast cancer.

10. The method of claim 1, wherein the patient is undergoing treatment for an immune related disease.

* * * * *